(12) United States Patent
Obrien et al.

(10) Patent No.: US 9,910,957 B2
(45) Date of Patent: Mar. 6, 2018

(54) VISUALIZATION, SHARING AND ANALYSIS OF LARGE DATA SETS

(71) Applicant: St. Petersburg State University, St. Petersburg (RU)

(72) Inventors: Stephen Obrien, Frederick, MD (US); Anton Svitin, St. Petersburg (RU); Sergey V. Malov, St. Petersburg (RU); Nikolay Cherkasov, St. Petersburg (RU); Paul G. Geerts, Turner (AU)

(73) Assignee: St. Petersburg State University, St. Petersburg (RU)

( * ) Notice: Subject to any disclaimer, the term of this patent is extended or adjusted under 35 U.S.C. 154(b) by 0 days.

(21) Appl. No.: 15/382,034

(22) Filed: Dec. 16, 2016

(65) Prior Publication Data

US 2017/0098031 A1   Apr. 6, 2017

Related U.S. Application Data

(63) Continuation of application No. 14/528,736, filed on Oct. 30, 2014, now Pat. No. 9,547,749.
(Continued)

(51) Int. Cl.
*G06F 19/18* (2011.01)
*G06F 19/26* (2011.01)
(Continued)

(52) U.S. Cl.
CPC ............ *G06F 19/26* (2013.01); *G06F 19/18* (2013.01); *G06F 19/28* (2013.01); *G06T 11/206* (2013.01); *G06T 19/003* (2013.01)

(58) Field of Classification Search
None
See application file for complete search history.

(56) References Cited

U.S. PATENT DOCUMENTS

| 7,184,041 B2 * | 2/2007 | Heng ..................... G06T 15/04 345/424 |
| 2005/0039110 A1 | 2/2005 | De La Vega et al. |

(Continued)

OTHER PUBLICATIONS

U.S. Appl. No. 14/528,736, in the U.S. Patent and Trademark Office, Office Action dated Mar. 28, 2016, 6 pages.
(Continued)

*Primary Examiner* — Said Broome
(74) *Attorney, Agent, or Firm* — Porzio, Bromberg & Newman P.C.

(57) ABSTRACT

Systems and methods for visualization, sharing and analysis of large data sets are described. Systems and methods may include receiving an input data set, wherein the input data set includes data that can be classified in classification dimensions wherein a first classification dimension is a linear ordering of data entries and a second classification dimension represents analysis criteria, traits of the data entries, or aspects of the data entries; obtaining an unabridged data table listing results for each combination of coordinates in the first classification dimension and the second classification dimension; and displaying contents of the unabridged data table as a visual array wherein two axes correspond to the coordinates and a third axis corresponds to a third classification dimension, wherein the third classification dimension represents an actual value of the respective data point for the coordinates. Methods may also assess the visual array, such as by identifying one or more regions of high density of signals.

20 Claims, 52 Drawing Sheets

Related U.S. Application Data

(60) Provisional application No. 61/897,524, filed on Oct. 30, 2013.

(51) Int. Cl.
    *G06F 19/28*     (2011.01)
    *G06T 11/20*     (2006.01)
    *G06T 19/00*     (2011.01)

(56) References Cited

U.S. PATENT DOCUMENTS

| | | |
|---|---|---|
| 2009/0125248 A1 | 5/2009 | Shams et al. |
| 2010/0281401 A1 | 11/2010 | Tebbs et al. |
| 2013/0058716 A1 | 3/2013 | Takano et al. |
| 2013/0212508 A1 | 8/2013 | Barsoum et al. |

OTHER PUBLICATIONS

U.S. Appl. No. 14/528,736, in the U.S. Patent and Trademark Office, Notice of Allowance dated Aug. 12, 2016, 7 pages.

U.S. Appl. No. 14/528,736, in the U.S. Patent and Trademark Office, Notice of Allowance dated Sep. 23, 2016, 11 pages.

International Search Report in related Application No. PCT/US2014/063173, dated Feb. 13, 2015.

Svitin et al., GWATCH: a web platform for automated gene association discovery analysis,: GigaScience, [online], Nov. 5, 2014, pp. 18-18, [retrieved on Jan. 29, 2015). Retrieved from the Internet: <URL: http://www.ncbi.nlm.nih.gov/pubmed/253>.

\* cited by examiner

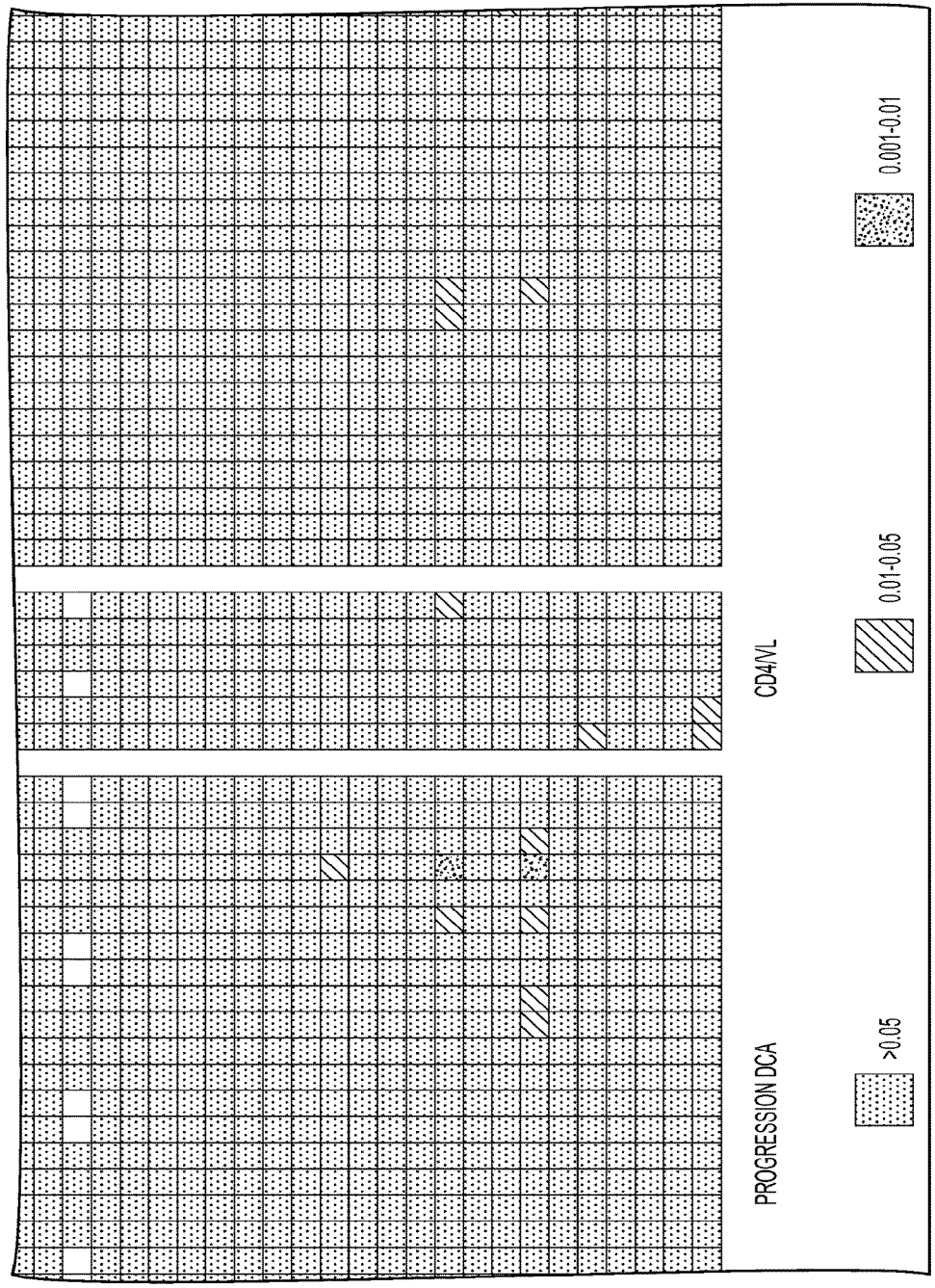

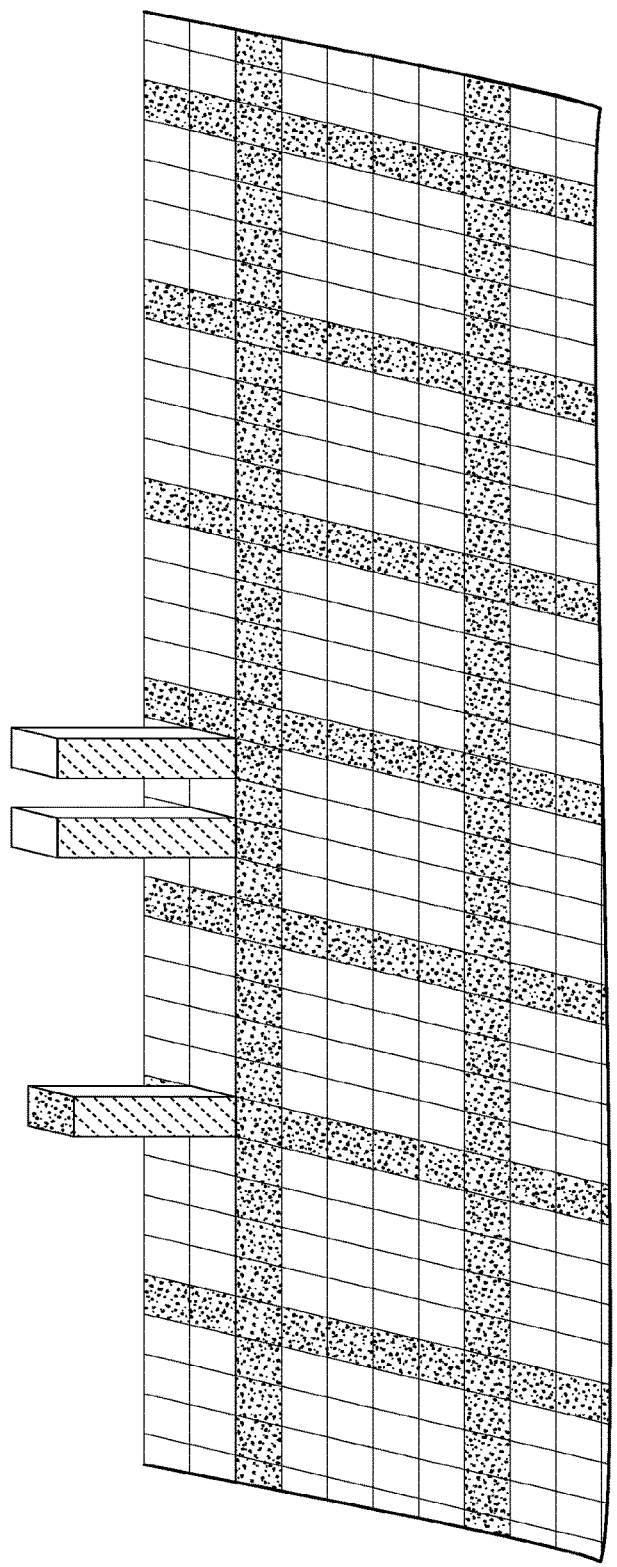

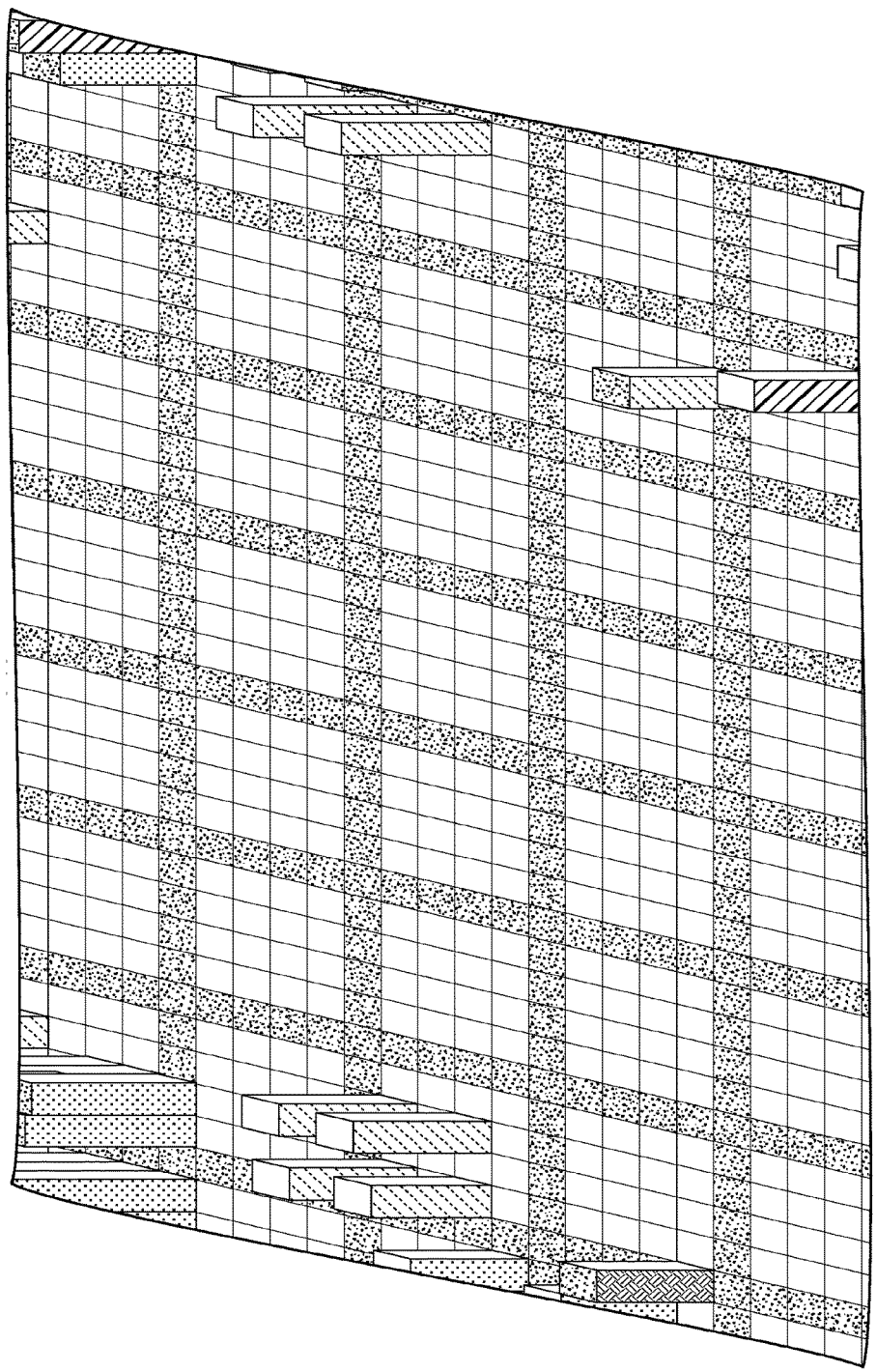

TRAX REPORT FOR rs11884476-1
| PROJECT ARG GROUP A EUROPEAN AMERICANS | | | | RACE | Freq 1 | Freq 2 |
|---|---|---|---|---|---|---|
| MARKER | SNP_A-8393199 | MAF: 0.06052 | | CAUCASIAN 917 | 0.93948 | 0.06052 |
| DB NAME | rs11884476 | | | TOTAL 917 | | |
| ALLELE 1: | C (0.93948) | ALLELE 2: | G (0.06052) | | | |
| CHROMOSOME: | 02 | COORDINATES: | 206318593 | GENE REGION: PARD3B | | |
| | CAUCASIAN |
|---|---|
| SC | 699 |
| OSN | 81 |
| HREU | 121 |
| SP | 16 |
| | 917 |
INFECTION TESTS
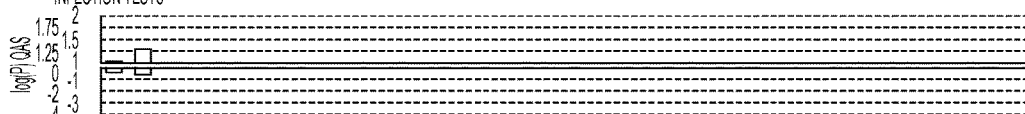
PROGRESSION DISEASE CATEGORICAL ANALYSIS (DICHOTOMOUS)
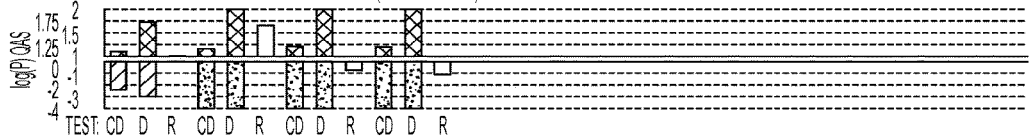
PROGRESSION DISEASE CATEGORICAL ANALYSIS (MULTIPOINT)
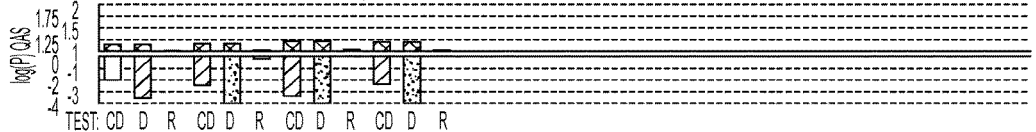
FIG. 8A TRAX REPORT FOR rs11884476-1
PROGRESSION SURVIVAL PROPORTIONAL HAZARD ANALYSIS (— — —1/1, - - - - 1/2, ——— 2/2)
CD4<200
FOR EUROPEAN AMERICAN
N = 636
QAS = 0.678448
P = 0.053206094
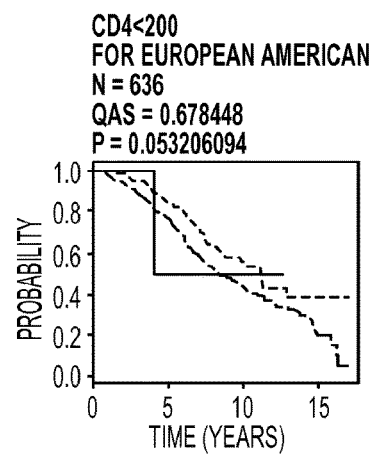
CD4<200
FOR GAYS
N = 470
QAS = 0.621373
P=0.02469109
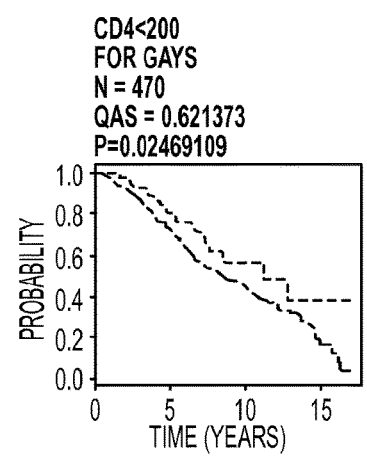
AIDS-93
FOR EUROPEAN AMERICAN
N = 636
QAS = 0.587542
P = 0.001405878
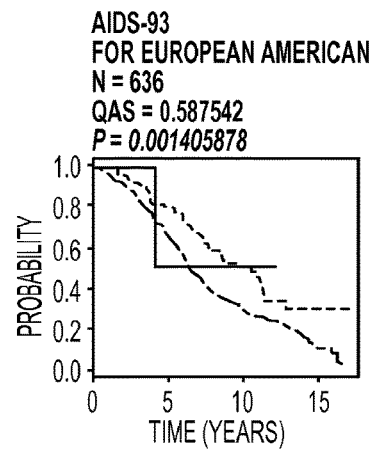
AIDS-93
FOR GAYS
N = 470
QAS = 0.571219
P = 0.002438975
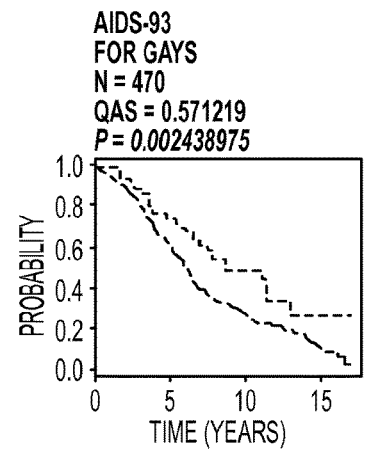
FIG. 9A TRAX REPORT FOR rs11884476-1
PROGRESSION SURVIVAL PROPORTIONAL HAZARD ANALYSIS (— — — 1/1, — — — — 1/2, ——— 2/2)
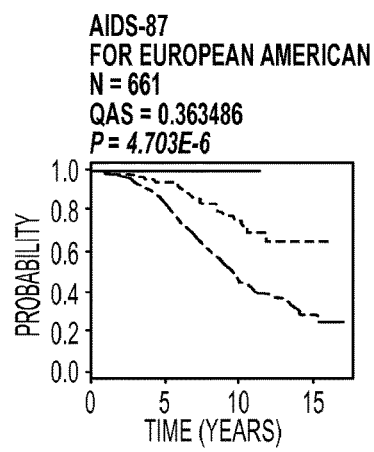
AIDS-87
FOR EUROPEAN AMERICAN
N = 661
QAS = 0.363486
P = 4.703E-6
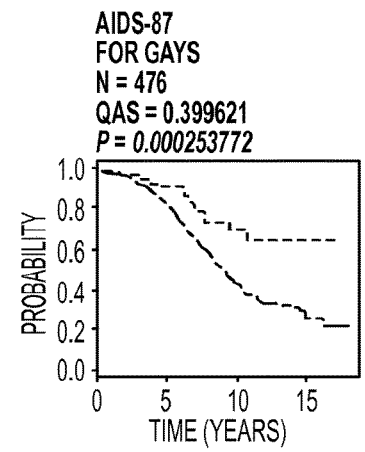
AIDS-87
FOR GAYS
N = 476
QAS = 0.399621
P = 0.000253772
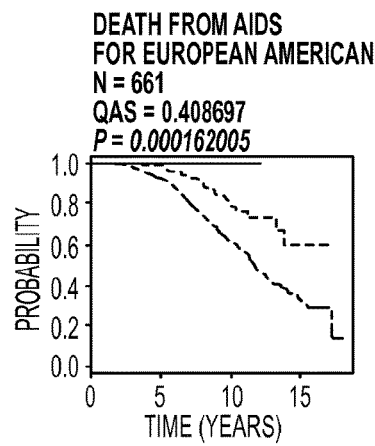
DEATH FROM AIDS
FOR EUROPEAN AMERICAN
N = 661
QAS = 0.408697
P = 0.000162005
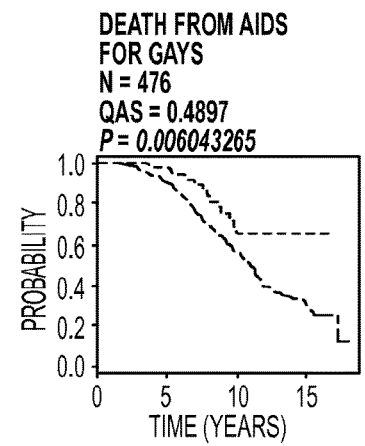
DEATH FROM AIDS
FOR GAYS
N = 476
QAS = 0.4897
P = 0.006043265
FIG. 9B

VISUALIZATION, SHARING AND ANALYSIS OF LARGE DATA SETS

CROSS-REFERENCE TO RELATED APPLICATIONS

The present invention is a continuation of U.S. patent application Ser. No. 14/528,736, filed Oct. 30, 2014, now U.S. Pat. No. 9,547,749, which claims priority to U.S. Provisional Patent Application No. 61/897,524, filed Oct. 30, 2013, the contents of which are incorporated by reference herein in their entirety.

FIELD OF THE INVENTION

The present invention relates to systems and methods for visualization, sharing and analysis of large data sets, and, more specifically, to systems and methods for data that can be classified in two dimensions for grouping into non-overlapping subsets.

BACKGROUND OF THE INVENTION

Many large data sets are difficult to work with and a challenge to analyze successfully. In particular, it is often difficult to quickly determine relevant data or associations of interest over a large data set. This problem arises in a number of fields.

For example, as genome-wide association studies (GWAS) plus whole genome sequence (WGS) analyses for complex human disease determinants are expanding, it is increasingly necessary to develop strategies to facilitate large data sharing, rapid replication and validation of potential disease-gene associations. This is especially true for signals that straddle the threshold for genome-wide significance due to small effect size, lack of statistical power in the study population, or a combination of these.

Annotations of human genome variation have identified some 60 million single nucleotide polymorphisms (SNPs), which offer the promise of connecting nucleotide and structural variation to hereditary traits. Genotyping arrays that resolve millions of common SNPs have enabled over 2000 GWAS to discover principal genetic determinants of complex multifactorial human diseases. Today, whole genome sequence association has extended the prospects for personalized genomic medicine, capturing rare variants, copy number variation, indels, epistatic and epigenetic interactions in hopes of achieving individualized genomic assessment, diagnostics, and therapy of complex maladies by interpreting one's genomic heritage.

GWAS studies to date have produced conflicting signals because many SNP associations fail to replicate in independent studies. Further, GWAS frequently fail to implicate previously-validated gene regions described in candidate gene associations for the same disease, and in most cases offer less than 10% of the explanatory variance for the disease etiology. In addition, discovered gene variants are frequently nested in noncoding desert regions of the genome that are difficult to interpret. At least part of these weaknesses derive from discounting SNP association "hits" that fail to achieve "genome-wide significance", a widely accepted, albeit conservative, statistical threshold set to discard the plethora of seemingly false positive statistical associations (Type I errors) that derive from the large number of SNPs interrogated.

A challenge to genetic epidemiology involves disentangling the true functional associations that fall below the genome-wide significance threshold from the myriad of statistical artifacts that also occur. No one has developed a real solution to this conundrum though some approaches have been offered. Many researchers agree that more widely practiced open access data sharing of unabridged GWAS data would offer the opportunity for multiple plausible approaches to bear on this question. However, for many cohorts, especially those developed before the advent of the genomics era, participants were not consented for open access of genome-wide data. Since patient anonymization is virtually impossible with genetic epidemiological data, the prospects of sharing patients' genotype and clinical data may conflict with ethical concerns over protecting the individual privacy of study subjects.

Needs exist for improved systems and methods for visualization, sharing and analysis of large data sets.

SUMMARY OF THE INVENTION

Certain embodiments may provide systems and methods for visualization, sharing, and/or analysis of large data sets. Certain embodiments may automate and facilitate genetic epidemiological discovery. This may be accomplished by:

1) Automated Analysis: Rapid gene association search and discovery analysis of large genome-wide datasets;

2) Display: Expanded visual display of gene associations for genome-wide variants (SNPs, indels, CNVs) including Manhattan plots, 2D and 3D snapshots of any gene region, and a dynamic genome browser illustrating gene association chromosomal regions;

3) Replication: Real time validation/replication of candidate or putative genes suggested from other sources, limiting GWAS statistical penalties related to Bonferroni multiple-testing correction; and 4) Release: Open data release and sharing by eliminating privacy constraints (IRB, Informed consent, HIPAA etc.) on unabridged results, which allows for open access comparative and meta-analysis.

In certain embodiments, systems and methods may be provided for visualization, replication, sharing or analysis of large data sets. Systems and methods may include receiving an input data set, wherein the input data set comprises data that can be classified in classification dimensions wherein a first classification dimension is a linear ordering of data entries and a second classification dimension represents analysis criteria, traits of the data entries, or aspects of the data entries; obtaining an unabridged data table listing results for each combination of coordinates in the first classification dimension and the second classification dimension; and displaying contents of the unabridged data table as a visual array wherein two axes correspond to the coordinates and a third axis corresponds to a third dimension, wherein the third dimension represents an actual value of the respective data point for the coordinates. Classification dimensions may define a plane. Additional dimensions may represent dimensions other than those defining the plane.

In certain embodiments, the visual array may include a fourth dimension that represents an additional component of the data point value. The fourth classification dimension may be represented by color or shape of the bars in the three-dimensional visual array.

In certain embodiments, the visual array may be a three-dimensional moving video mode above a surface wherein two axes in the horizontal plane represent the first classification dimension and the second classification dimension, while height of blocks rising from that plane represent the third dimension.

The input data set may be ready for output (i.e. can be classified in two dimensions as it is), and further comprising optional reformatting of the input data set to create the unabridged data table. Certain embodiments may also include analyzing the input data set or converting the input data set to obtain the unabridged data table.

In certain embodiments, the input data set may be the result of a genome-wide association studies (GWAS) or whole genome sequence (WGS) association study or its analysis. A first axis of the visual array may represent SNPs linearly ordered according to their genomic positions, a second axis may represent different association tests performed, height of blocks rising above the surface represents reversed sign decimal logarithm of p-value (−log p-value), and color represents quantitative association statistics (QAS). The quantitative association statistics may represent direction and strength of associations for association tests and may be selected from the group consisting of: odds ratio, relative hazard, ez2-transformed correlation coefficient, and combinations thereof. In certain embodiments, an output contains one or more of the following features: data table listing all SNPs, comprising names and chromosome coordinates, with p-values and QASs for each test; Manhattan plots showing p-values for all genotyped SNPs for any single test, computed for all tests; three-dimensional moving video mode allowing navigation above the chromosome surface and viewing more detailed association statistics and SNP information; two-dimensional snapshot of a selected genomic region in the form of a heat plot indexed by the p-values; three-dimensional snapshot of a selected genomic region in the form of a static image of a three-dimensional moving video mode; polarized three-dimensional snapshot of a selected genomic region where values of QAS are inverted according to the value of linkage disequilibrium (LD) between minor allele of the index SNP and those of other neighboring SNPs; summary of all test results for a single SNP; analytical report of all tests performed for a single SNP; and list of SNP-test combinations ranked according to p-values, QASs or density of significant p-values across closely linked SNPs and related tests for a disease stage.

Certain embodiments may include receiving a search query regarding the visual array to locate any single region of interest by SNP rs-number, gene name, chromosome coordinates or the threshold for −log p-value within the currently selected chromosome or throughout the whole genome and displaying this region of interest. The analysis may utilize genomic data in the form of patients' genotypes and clinical (phenotypic) data selected from the group consisting of, but not limited to: categorical clinical data, right-censored survival clinical data, and combinations thereof. If the primary data (genotypes and clinical/phenotypic data) are received, rather than processed data (p-values and QAS), the analysis of these primary data may include tests selected from the group consisting of, but not limited to: categorical tests, proportional hazards survival tests, categorical tests for survival data, Hardy-Weinberg equilibrium tests, and combinations thereof.

To better recognize signals in the dataset of study and distinguish them from the noise, additional analysis may be performed that may include assessment of the shape of a three-dimensional surface landscape in the visual array. The assessment may include identification of regions of high or low density of statistical signals.

Certain embodiments may include performing meta-analyses of the visual array in a dynamic browser displaying association results.

Certain embodiments may include anonymization of a genomic data set to produce the input data set. Embodiments may also include isolating and sampling DNA to produce the genomic data set.

Certain embodiments may include systems and methods for visualization, replication, sharing and analysis of large data sets. Systems and methods may include accessing an input data set, wherein the data set (or the result of its analysis) comprises data that can be classified in two dimensions wherein a first dimension is a linear ordering of data entries and a second dimension represents analysis criteria, traits of the data entries, or aspects of the data entries; if needed, analyzing the data set or converting it to obtain an unabridged data table, wherein the data table lists results for each combination of the coordinates in the two dimensions (classification dimensions); and displaying contents of the unabridged data table as a visual array where first two axes correspond to the coordinates in the two classification dimensions and the third one corresponds to the actual value (result) of the respective data point for these coordinates; optionally, the fourth "dimension" (e.g. color or shape) can be introduced to represent additional component of the data point value.

In certain embodiments, the visual array may be a three-dimensional moving video mode above a surface wherein two axes in the horizontal plane represent classification dimensions, while height, and optionally color, of blocks rising from that plane represent value for the combinations of coordinates in classification dimensions. The input data set may be ready for output (can itself be classified in two dimensions) and the unabridged data table can be obtained by the optional reformatting of this data set. Alternatively, the input data set may first need to be analyzed to obtain the unabridged data table that can be output. The input data set may be the result of the GWAS or WGS association study or its analysis. A long axis of the visual array may represent SNPs linearly ordered according to their genomic positions. A short axis may represent different association tests performed. Height of blocks rising above the surface may represent reversed sign decimal logarithm of p-value (−log p-value) and color may represent quantitative association statistics (QAS). The QAS may represent and/or explain direction and strength of associations for association tests and may be selected from the group consisting of, but not limited to, the following: odds ratio, relative hazard, ez2-transformed correlation coefficient, and combinations thereof. The output may contain any of the following features or their combinations: data table listing all SNPs (names and chromosome coordinates) with p-values and QASs for each test; Manhattan plots showing p-values for all genotyped SNPs for any single test, computed for all tests; three-dimensional dynamic HIGHWAY browser as described herein, allowing navigation above the chromosome surface and viewing more detailed association statistics (p-value, QAS) as well as SNP information (rs-number, coordinates, minor allele frequency—MAF, etc.) by placing the mouse pointer atop the bar for any SNP-test combination or by any other way; two-dimensional snapshot (2D-SNAPSHOT) of a selected genomic region in the form of a heat plot indexed by the p-values; three-dimensional snapshot (3D-SNAPSHOT) of a selected genomic region in the form of a visual array as described herein, only non-dynamic, that may be labeled with SNP rs-number, chromosome coordinates and minor allele frequencies; polarized three-dimensional snapshot of a selected genomic region which is identical to the 3D-SNAPSHOT, except that values of QAS are inverted according to the value of linkage disequilibrium (LD) between minor allele of the index SNP and those of other neighboring SNPs; summary of all test results for a single SNP (TRAX PAGE); detailed analytical report of all tests performed for a single SNP (TRAX PAGE) including tables, bar graphs, survival curves and additional parameters for each test; and list of SNP-test combinations ranked according to p-values, QASs or density of significant p-values across closely linked SNPs and related tests for a disease stage, providing an association discovery tool. Certain embodiments may include receiving a search query regarding the visual array to locate any single region of interest by SNP rs-number, gene name, chromosome coordinates or the threshold for −log p-value within the currently selected chromosome or throughout the whole genome and displaying this region of interest. The analysis may utilize genomic data in the form of patients' genotypes and clinical (phenotypic) data selected from, but not limited to, categorical clinical data, right-censored survival clinical data, and combinations thereof. If the primary data (genotypes and clinical/phenotypic data) are received, rather than processed data (p-values and QAS), the analysis of these primary data may include tests selected from the group consisting of, but not limited to, the following: categorical tests, proportional hazards survival tests, categorical tests for survival data, Hardy-Weinberg equilibrium tests, and combinations thereof. To better recognize signals in the dataset of study and distinguish them from the noise, additional analysis may be performed that can include assessment of the shape of three-dimensional surface landscape in the visual array through various methods including identification of the regions of high or low density of statistical signals.

Systems and methods for visualization, sharing and analysis of large data sets may include: accessing an input data set, wherein the data set (or the result of its analysis) comprises data that can be classified in two dimensions wherein a first dimension is a linear ordering of data entries and a second dimension represents analysis criteria, traits of the data entries, or aspects of the data entries; if needed, analyzing the data set or converting it to obtain an unabridged data table, wherein the data table lists results for each combination of the coordinates in the two dimensions (classification dimensions); and displaying contents of the unabridged data table as a visual array where first two axes correspond to the coordinates in the two classification dimensions and the third one corresponds to the actual value (result) of the respective data point for these coordinates; optionally, the fourth "dimension" (e.g. color or shape) can be introduced to represent additional component of the data point value.

Systems and methods for visualization, sharing and analysis of large data sets may include optionally anonymization of a genomic data set to produce a primary data set; accessing the primary data set; performing statistical tests on the primary data set and arranging obtained derivative data set (analysis results) in a first dimension and a second dimension wherein a first dimension is a linear ordering of data entries; displaying contents of the derivative data set as a visual array; sharing the derivative dataset as visual array, data tables, other visual displays, etc.; and performing meta-analyses of the visual array in a dynamic browser displaying association results. Certain embodiments may include isolating and sampling DNA to produce the genomic data set. A large data set may be a genome-wide association studies (GWAS) or a whole genome sequence (WGS) analysis.

Certain embodiments may include systems and/or methods of displaying large data sets. The systems and/or methods may include receiving an input data set, wherein the input data set comprises data that can be classified in two classification dimensions; displaying the input data set in a graph that have three or more output dimensions; and allowing a user to navigate above a plane of two output dimensions from the graph.

In certain embodiments, the three or more output dimensions may be four output dimensions. The navigation may be a three-dimensional moving video mode. The plane may be a representation of a chromosome, wherein the user may view association statistics and SNP information. A baseline transversal axis of the graph may be a list of tests, and a longitudinal axis of the graph may list ordered SNPs to create a surface. A vertical axis rising out of the surface may represent −log p-values, and color may reflect quantitative association statistics. A large data set may be a genome-wide association studies (GWAS) or a whole genome sequence (WGS) analysis.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

Figure 5B:
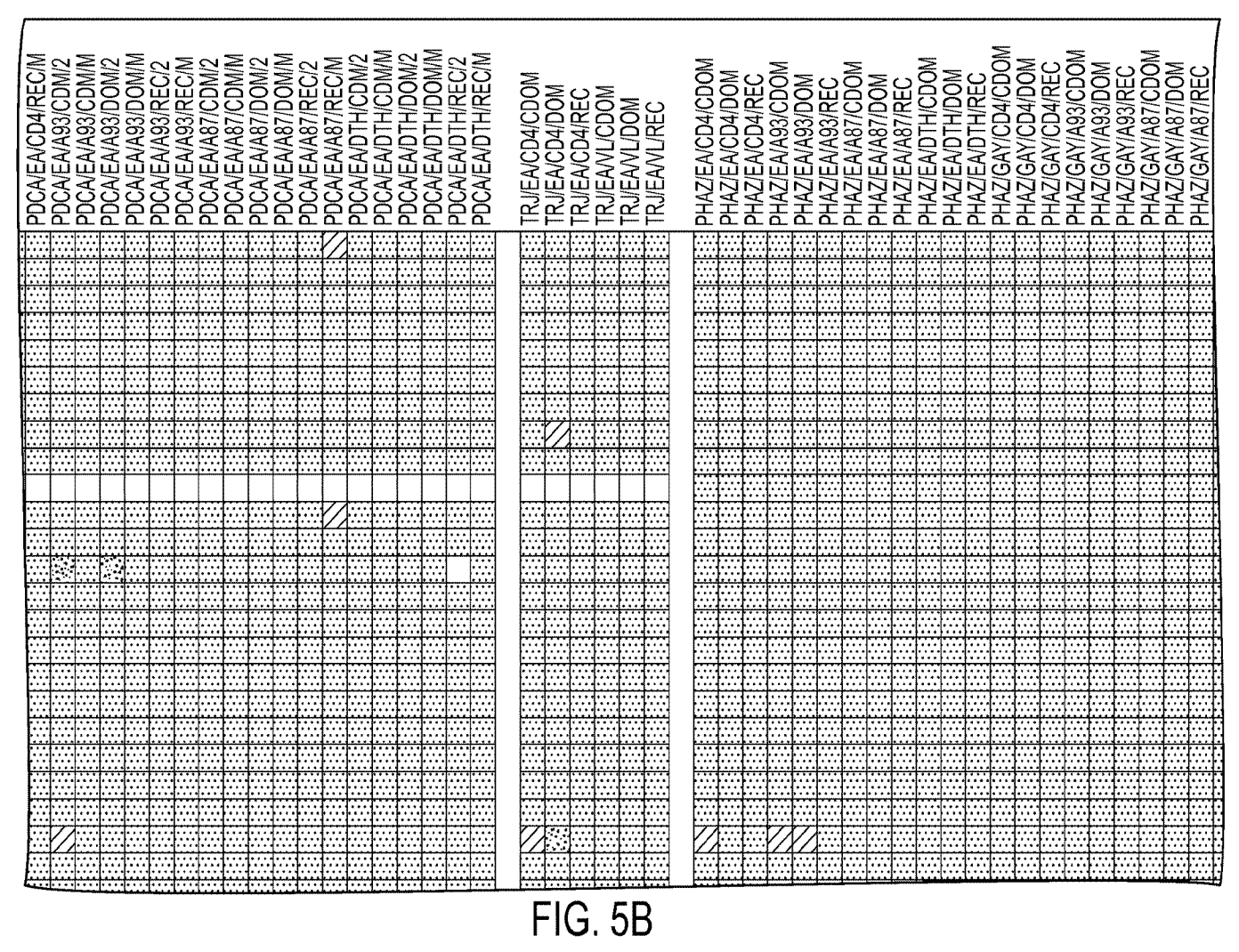
Figure 5C:
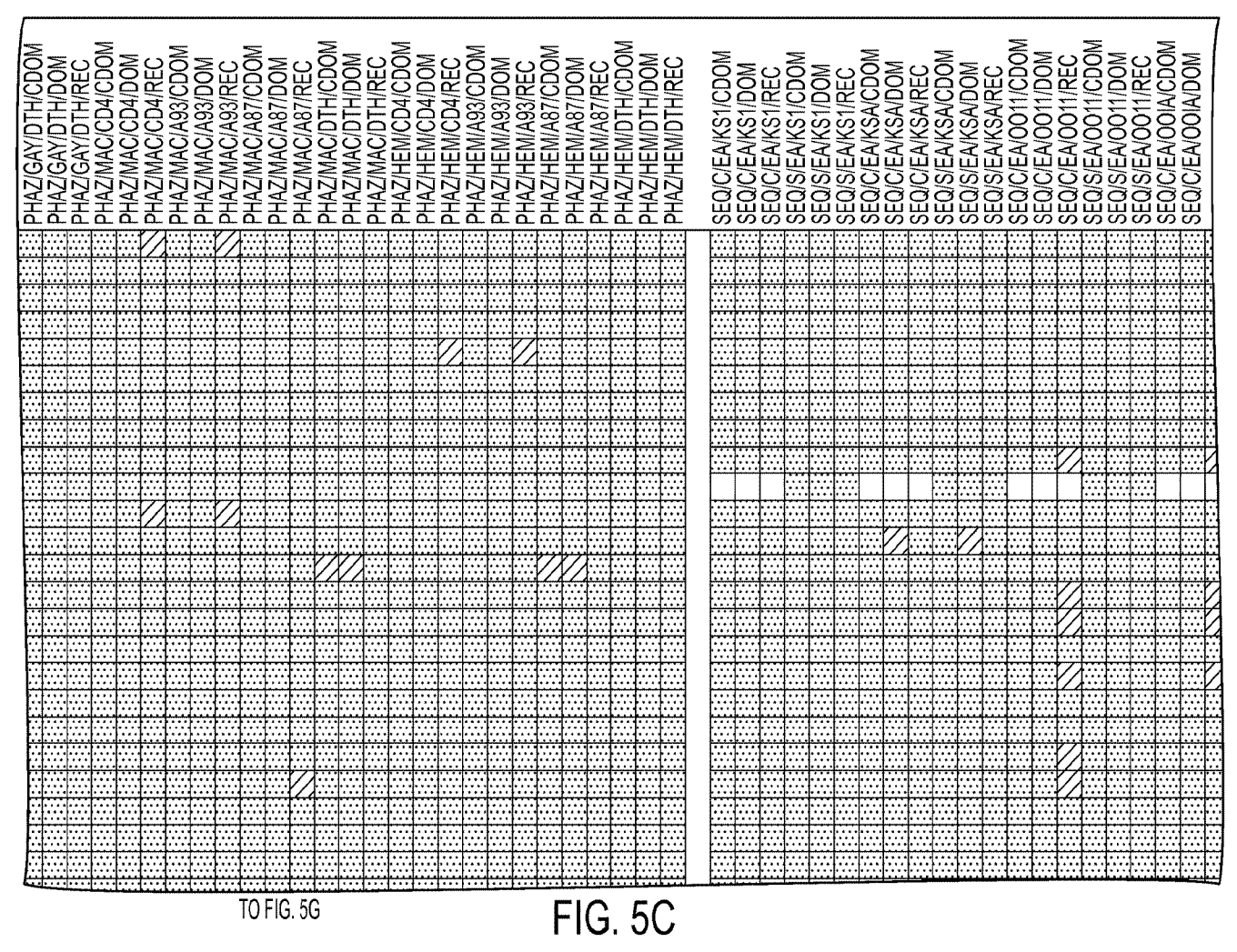

FIGS. 5A-5L shows an exemplary 2D-SNAPSHOT heat plot of associated gene data for selected region illustrating significant p-values (color intensity) for association of linked SNP alleles.

FIGS. 8A-8B shows an exemplary TRAX PAGE, presenting a summary of all test results for a single SNP for a study group (e.g., p-values and QASs for HIV infection, AIDS progression using categorical and survival tests, AIDS sequelae, and HAART outcomes can be viewed and compared).

FIGS. 9A-9B shows an exemplary section of a detailed TRAX REPORT of derived statistics for all the tests accomplished for a single SNP illustrating an example of the appearance of the production of survival curves.

DETAILED DESCRIPTION OF THE PREFERRED EMBODIMENTS

Figure 1:
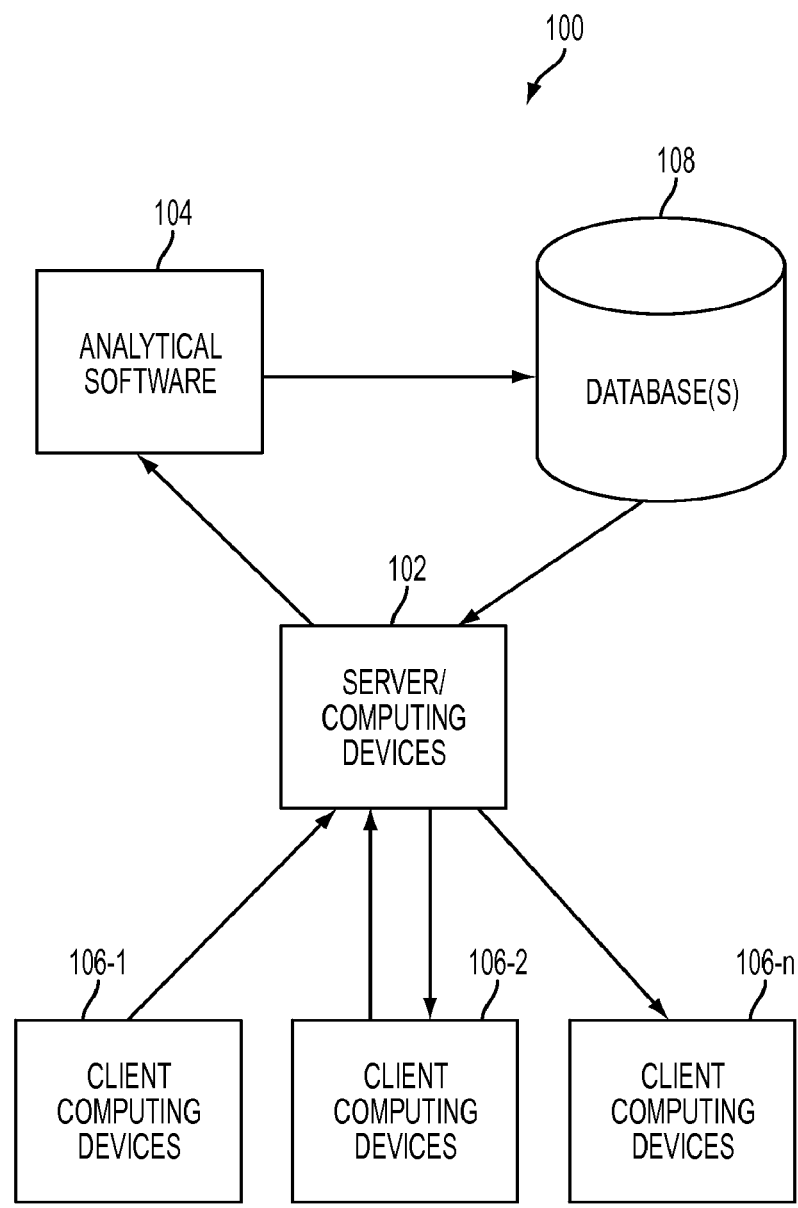
FIG. 1 shows an exemplary system for gene discovery and data sharing in disease association analyses across the genome.

Systems and methods are described for using various tools and procedures for visualization, sharing and analysis of large data sets. In certain embodiments, the tools and procedures may be used in conjunction with genome studies. The examples described herein relate to human genome studies for illustrative purposes only. The systems and methods described herein may be used for many different industries and purposes, including human, animal, plant, bacteria and other genome studies and/or other industries completely. In particular, the systems and methods may be used for any industry or purpose where large data analysis and sharing is needed. For multi-step processes or methods, steps may be performed by one or more different parties, servers, processors, etc.

Large datasets may be any data sets. In certain embodiments, large data sets may be genome-wide association studies (GWAS) and/or whole genome sequence (WGS) analyses. In certain embodiments, large data sets may be any data set with more than approximately 100 data points, more than approximately 1,000 data points, more than approximately 10,000 data points, more than approximately 100,000 data points, more than 1,000,000 data points, more than approximately 10,000,000 data points, more than 100,000,000 data points, etc. Data points may be ordered to create an axis of a display. The display may be sequential or another type of order. The display may have one axis corresponding to the number, name, location, etc. of the data points. This axis may be one of a plurality of classification dimensions for the data set. The display may be a moving graph in two or more dimensions. The movement may be along this axis corresponding to the number, name, location, etc. of the data points.

Embodiments described herein may be applicable to visualization, analysis and sharing of any data that can be classified in two dimensions, one of which may serve as a reference for linear ordering of data entries, while another may represent different analysis criteria, different traits or aspects of data and thus allow grouping of these data into several non-overlapping subsets. In an extreme case, the second dimension can consist of a single unit, thus grouping all data together. If the input data can be classified in this two-dimensional setting, they then can be output and visualized using the approach described herein. In certain embodiments, they may be output and visualized as a dynamic three-dimensional graphical view shown in an exemplary visualization system where first two axes correspond to two classification dimensions and a third axis may be an actual value of the respective data point (e.g. p-value or some other quantitative or qualitative result) corresponding to the combination of the values of two classification parameters. Optionally, a fourth "dimension" (e.g. color or shape) can be introduced to represent an additional component of the data point value. In addition to visual inspection, automatic assessment of the shape and structure of this three-dimensional representation can be used for analysis of the data. This can be done by looking for regions of high and/or low density of statistical signals through the study of three-dimensional surface "landscape" produced in a graphical representation, which is demonstrated in an exemplary realization herein as a density feature. This analysis approach can be helpful to improve over existing techniques for recognition of true signals and distinguishing them from noise.

Certain embodiments may provide for meta-analysis. Meta-analysis may be statistical methods for contrasting and combining results from different studies to identify patterns among study results, sources of disagreement among those results, or other interesting relationships.

To clarify and illustrate the two-dimensional classification of input data and three-dimensional output format, an exemplary approach described herein relates to the analysis of the data from GWAS and WGS association studies. In this case, the first dimension, which allows linear ordering of data entries, may be the genomic position of the SNP, with the SNPs being naturally ordered along the chromosome. The second dimension in this case may be different association tests performed (for different stages of disease, patient subgroups, genetic models and so on) that allows grouping data in several subsets where each subgroup is the collection of results for all SNPs for the same one test. This may allow for representation of input data with SNPs on one axis, tests on another axis and the results (reverse sign decimal logarithm of p-value) of the given test for the given SNP on the third axis. An additional "dimension", such as color, may also be used to represent quantitative association statistics (QAS, see below). Therefore, a three-dimensional dynamic output may be provided.

In the described exemplary embodiment the data that are output in the above format are not the primary data (genotypes and phenotypic/clinical data of patients/study participants), but rather the derivative results of analysis (p-values and QAS), represented in the dynamic 3D visualization by height of the bars and their color, respectively). Such output of the test/analysis results and not the original (primary or "raw") data is not required by the described invention in general, but can be beneficial since it can facilitate data sharing in two aspects (but not limited by these examples): 1) in cases where open release of original (primary) data can be complicated due to privacy, confidentiality, commercial secret, copyright, ethical or other concerns, release of derivative test/analysis results may still allow for data sharing, thus overcoming these obstacles; and/or 2) in cases where release of original (raw) data can be complicated due to the large size of the data, derivative test/analysis results may be smaller due to their summary nature, which may allow for effective data sharing. In addition to the advantages described above, representation of data in this format may also be easier to understand and comprehend, and allow for a more intuitive organization of the data providing grounds for adequate cataloguing and thus effective storage and retrieval of the information.

As stated above, this representation, visualization, analysis and data sharing approach may be applicable to any data that can be laid out in two dimensions with results forming the third dimension. This can be especially important and relevant, among other things, for large datasets, such as large-scale biological data. One area for application may be analysis of data that correlates with the genomic position. Apart from the realization described below for the human GWAS and WGS association studies data analysis, the following applications and/or realizations can be envisioned without limiting the scope of the invention:

representation, visualization, analysis, cataloguing, replicating and/or sharing of data from the studies of human transcriptome, such as (but not limited to) RNA-seq studies for association with phenotypic traits, disease predisposition, clinical symptoms etc.;

representation, visualization, analysis, cataloguing, replicating and/or sharing of data from the studies of human proteome, such as (but not limited to) proteomic studies for association with phenotypic traits, disease predisposition, clinical symptoms etc.;

representation, visualization, analysis, cataloguing, replicating and/or sharing of data from the studies of human epigenome, such as (but not limited to) methylome studies for association with phenotypic traits, disease predisposition, clinical symptoms etc.;

representation, visualization, analysis, cataloguing, replicating and/or sharing of data from the studies of human metabolome, such as (but not limited to) small-molecule metabolite studies for association with phenotypic traits, disease predisposition, clinical symptoms etc.;

representation, visualization, analysis, cataloguing, replicating and/or sharing of data from the studies involving personalized human genome and/or transcriptome and/or proteome and/or methylome and/or metabolome assessment and interpretation, such as (but not limited to) assessment of individual genome composition by whole genome sequencing for diagnostic purposes and/or for following estimation of personal health risks in relation to lifestyle, employment, health and life insurance etc. by comparison of obtained personal genomic data with known genetic associations and/or genomic risk factors;

any of the above applications performed in non-human species, such as (but not limited to) GWAS or WGS association studies in mice, rats, cats, dogs, chickens, cows, horses and others, studies for association of genome and/or transcriptome and/or proteome and/or metabolome with infectivity, pathogenicity and immunogenicity in viruses and bacteria, including vaccine studies;

representation, visualization, analysis, cataloguing, replicating and/or sharing of data from pharmacogenomics and pharmacogenetics studies and clinical trial studies in humans and non-human species, such as (but not limited to) studies of the patients' response to the medication in relation to their genetic background;

representation, visualization, analysis, cataloguing, replicating and/or sharing of data from the high-throughput discovery of the biological drugs (e.g., therapeutic monoclonal antibodies) which relate properties of the molecules to their nucleotide and/or amino acid sequence, such as (but not limited to) studies where data can be plotted as genomic position versus various tests for different properties of the molecule, such as affinity for different targets, thermal stability, biological activity, toxicity etc.;

representation, visualization, analysis, cataloguing, replicating and/or sharing of data from the high-throughput discovery of the small-molecule drugs which relate properties of the molecules to their chemical structure and/or concentration, such as (but not limited to) studies where data can be plotted as chemical structure versus various tests for different properties of the molecule (such as affinity, biological activity, toxicity etc.) and/or for different concentrations;

representation, visualization, analysis, cataloguing, replicating and/or sharing of data from the studies of the genetic polymorphism, such as (but not limited to) data from the studies of the genetic polymorphism between vaccine batches and/or natural isolates of the pathogen, plotted as genomic position versus abundance of each of the four nucleotides in the given genomic position.

In relation to the realization described herein, potential purposes, applications and advantages may include one or more of the following:

automated gene association detection in large association studies for complex human diseases;

assessment of candidate genes that are suggested by functional studies for a disease by inspecting SNPs or variants in candidate gene chromosomal regions. This inspection may abrogate significant statistical multiple-testing penalties of GWAS or WGS analyses because it is hypothesis driven;

real-time independent replication of GWAS and WGS association hits from other cohorts run for the same disease;

providing an analysis platform for interpretation of multiple cohort studies together, the principal of a meta-analysis;

providing a new approach for open access/unabridged data release of gene association studies results without violating privacy, IRB (institutional review board) regulations, HIPAA (The Health Insurance Portability and Accountability Act of 1996) provisions or informed consent constraints. Although the released results are dependent on private clinical and genetic personal data, these data are not released, and the released results are the derivative ones (p-values, QAS, detailed survival curves, bar plots and tables in TRAX PAGE and TRAX REPORTS);

applicable to GWAS, to whole genome sequence association studies, and personalized genome sequence analysis and diagnostics.

The following is an exemplary use of certain embodiments for genome analysis. An exemplary data release platform may display unabridged genetic association data results without compromising privacy or informed consent constrictions, allowing for rapid discovery and replication opportunities. An exemplary dataset that is released via the described embodiment is a result of a survey for HIV-AIDS resistance genes screened in a large multicenter cohort genome-wide association study.

An exemplary web-based, server-based or hardware-based analytical package may address issues with previous approaches to genome studies with an organized open release of unabridged SNP-test association results from GWAS and whole genome sequencing (WGS) association studies. As illustrated herein for an exemplary embodiment, a Genome-Wide Association Track Chromosome Highway (GWATCH) may be a dynamic genome browser that displays primary analysis results—p-values and QAS—from multiple association tests performed for one or more cohorts in a GWAS or WGS association study as a visual array ordered by SNP chromosomal position.

As a first step in analysis, GWATCH may allow scrolling across any chromosomal region to view results (p-values and QAS) of several thousand disease-SNP association tests in any chromosome region housing a gene of interest. The imagery provides a dynamic traverse along a human chromosome producing a "bird's eye" view of the strong SNP associations that rise above the chromosome highway surface. The idea is to visualize association results across a gene region (e. g. one that may include a highly significant SNP association) for all the tests performed (on the same or different cohorts) and for all the neighboring, potentially proxy SNPs (i.e., SNPs which track the neighboring causal, disease-affecting SNP due to the linkage disequilibrium, LD) for the same tests. The view may allow visual inspection of related associations for non-independent tests, and non-independent SNP genotypes (e.g., analysis of tests for the same disease stage and/or for the group of nearby SNPs).

Typical input of a GWAS analysis may include a large unabridged Data-Table listing p-values and QASs across multiple SNP association tests performed for a list of a million or more ordered SNPs. GWATCH may display the Data-Table, Manhattan plots for each test (FIG. 3), a dynamic chromosome browser that indicates significant p-values and QASs from the Data-Table (FIG. 4) or produces analytical result reports for any SNP (TRAX PAGE and TRAX REPORT in Table 1 and FIGS. 8A-8B and FIGS. 9A-9B).

Described herein as an exemplary use, is an application of GWATCH using a GWAS carried out with study participants enrolled in eight prospective HIV-AIDS cohorts, searching for AIDS Restriction Genes—ARG. In this case, a GWAS meta-analysis was performed on 5922 patients with distinctive clinical outcomes genotyped using an Affymetrix 6.0 genotyping array (700,022 SNPs after quality control—QC—filters) and parsed into three population groups (Table 2):

Group A) A select group of 1527 European American individuals;

Group B) A total of 4462 European American individuals that includes Group A;

Group C) An independent group of 1460 African American individuals.

Based upon available clinical information, 123 genome wide association (GWA) experimental tests were performed on Group A, 144 GWA tests on Group B, and 60 GWA tests on Group C (Table 3). The GWA tests include allele and genotype associations for HIV acquisition/infection, AIDS progression (including categorical and survival analyses), AIDS defining conditions and Highly Active Antiretroviral Therapy (HAART) outcomes. The unabridged dataset displayed in GWATCH-ARG, however, is far richer than those analyzed in the previous studies. GWATCH-ARG presents complete results for 700,022 SNPs for 327 tests (Table 3) for 5922 study participants listed in Table 2.

For the three ARG analysis groups A-C (Table 2), GWATCH-ARG presents several distinctive display features that allow detailed inspection of the composite GWAS results for individual SNPs and for groups of linked SNPs across all human chromosomal regions (Table 1).

1.) The principal data set is a large DATA TABLE listing all SNPs (names and chromosome coordinates) with QASs and p-values for each test described in Table 3.

Figure 3:
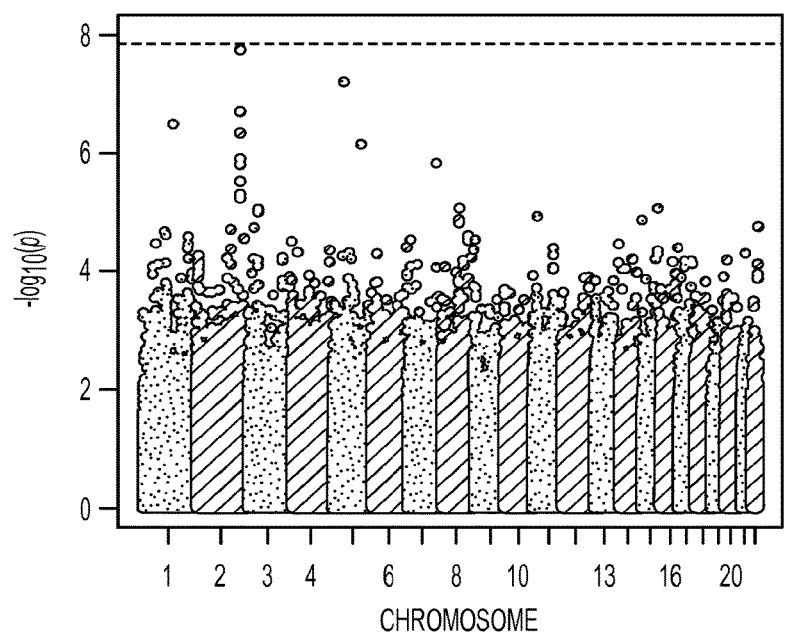
FIG. 3 shows exemplary MANHATTAN plot for selected association test illustrating p-values of association for all genotyped SNPs.
Figure 4:
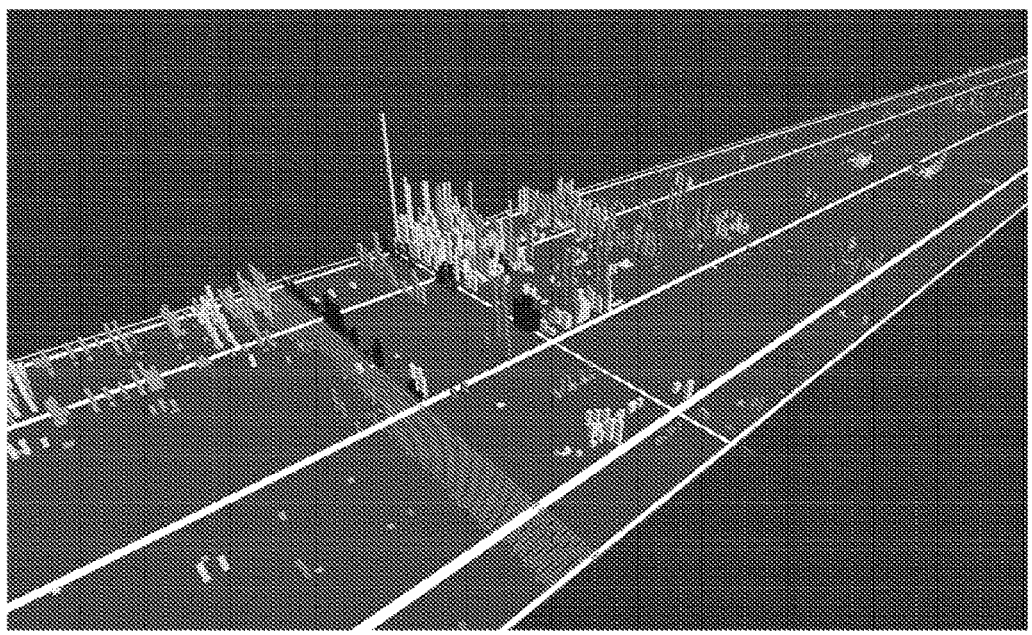
FIG. 4 shows an exemplary HIGHWAY browser view, a dynamic 3D chromosome view of associated gene data for selected region illustrating significant p-values (block height), quantitative association statistics (QAS)-based direction (color: green for QAS<1.0, red for QAS>1.0) and QAS-based strength (color intensity) of association for linked SNPs alleles.
Figure 5A:
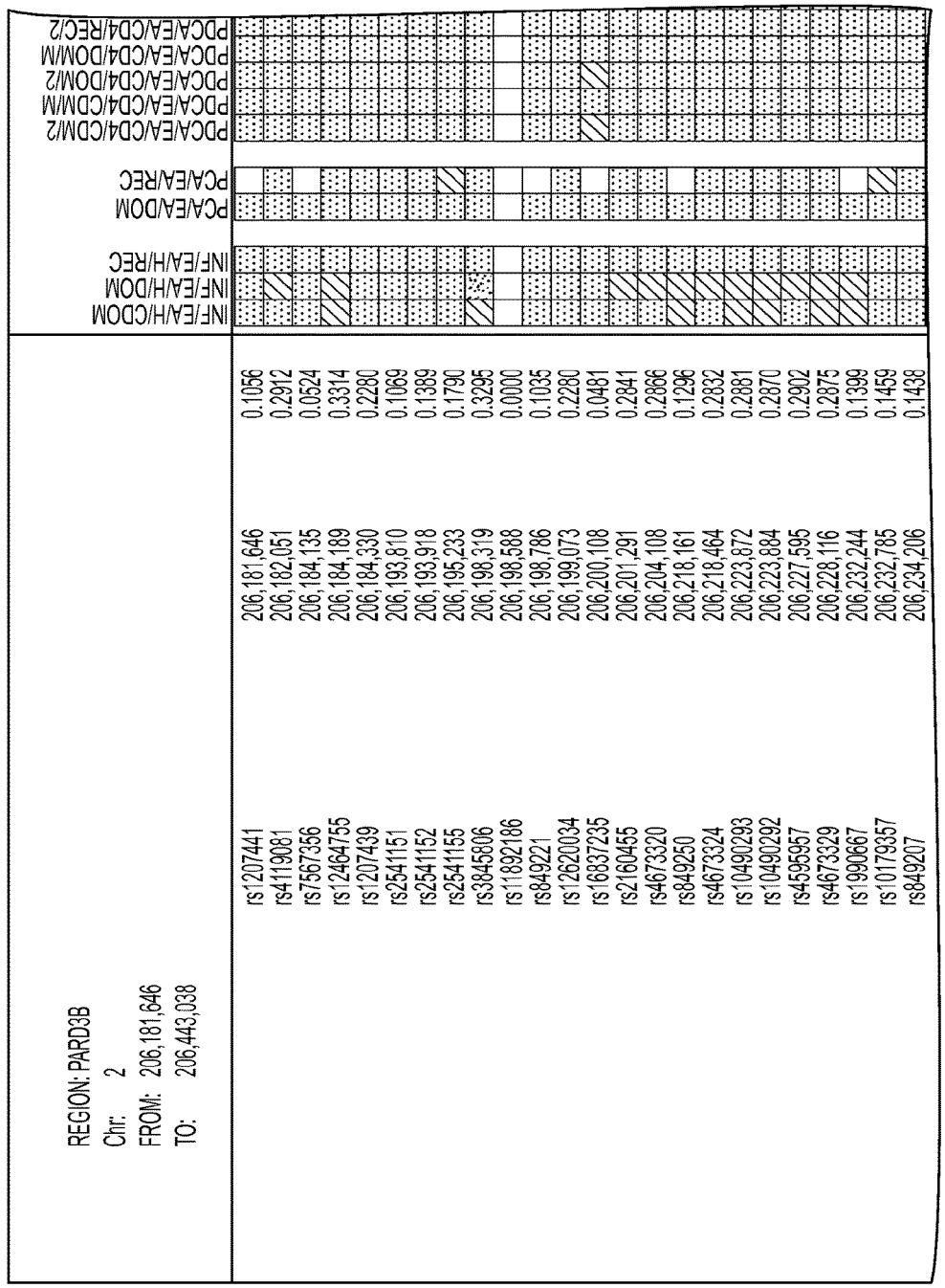
Figure 5D:
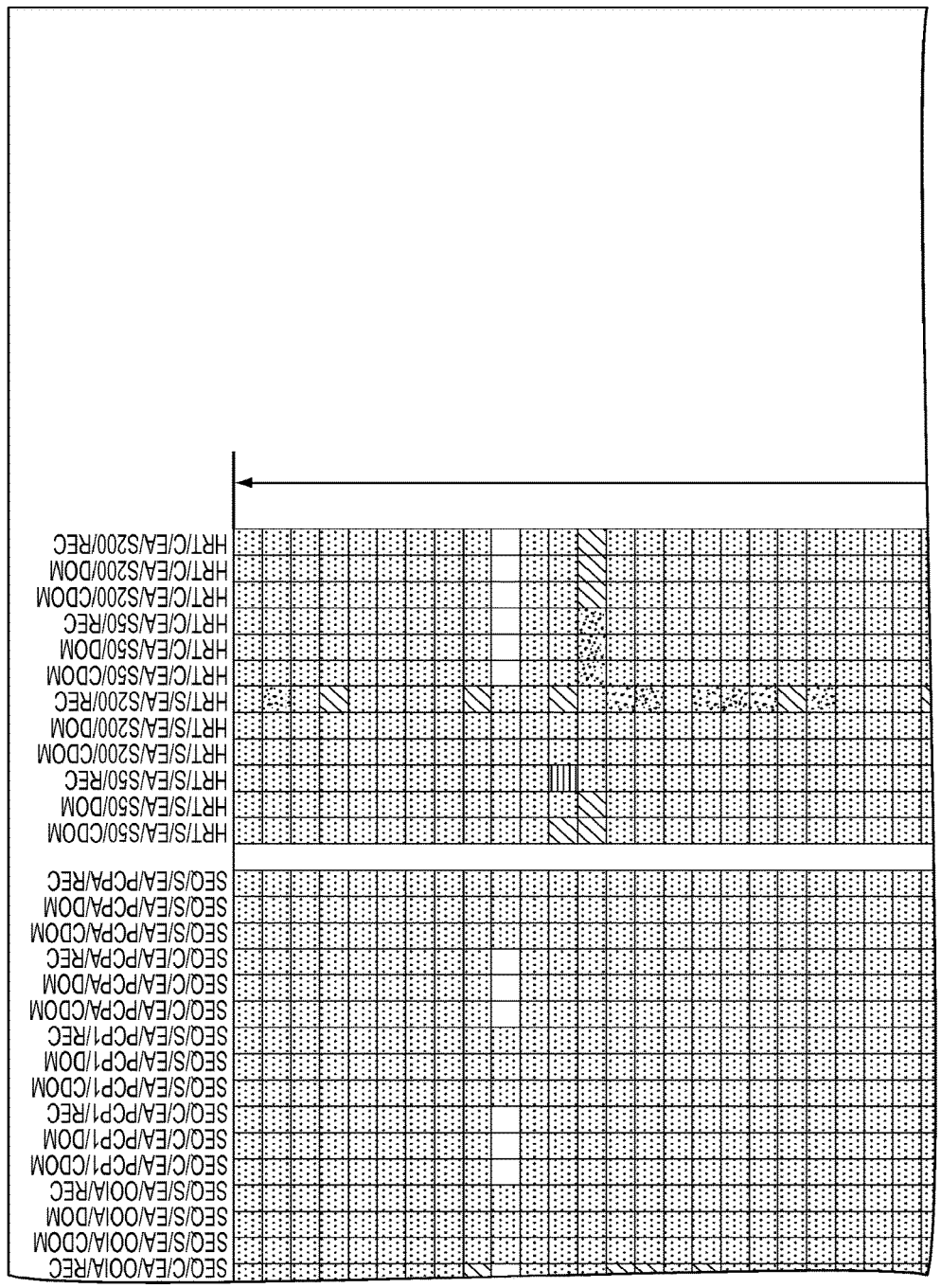
Figure 5E:
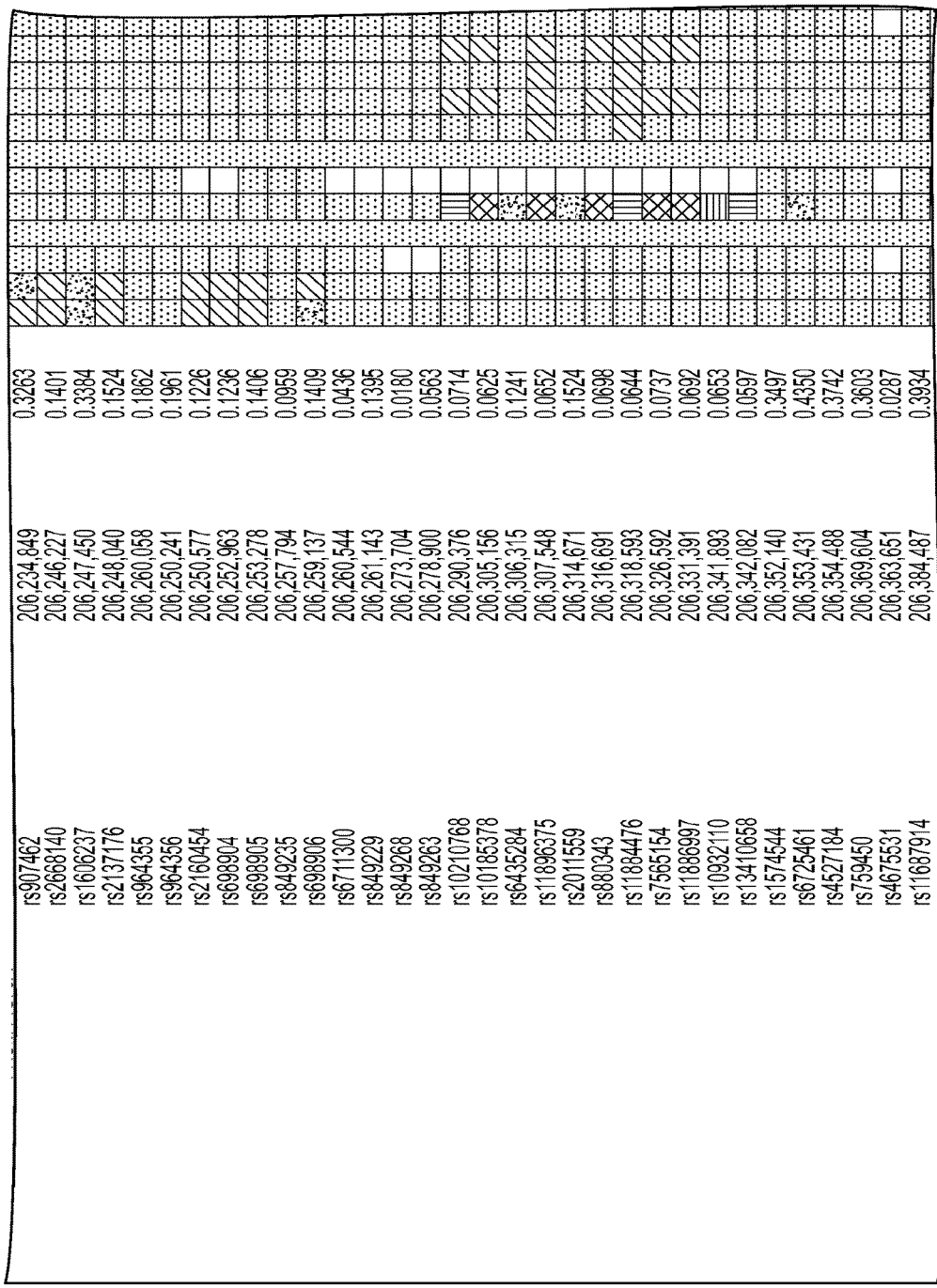
Figure 5F:
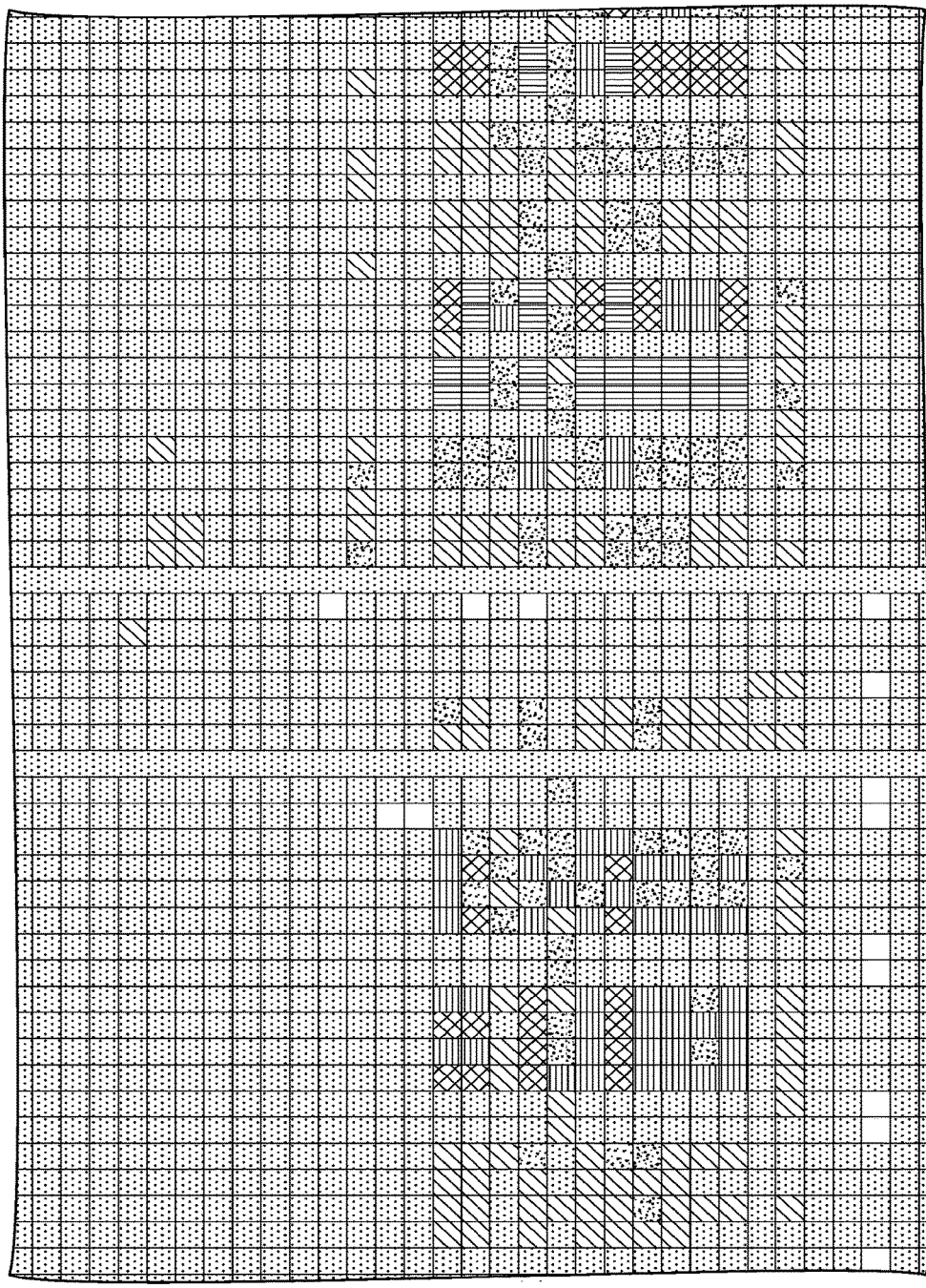
Figure 5G:
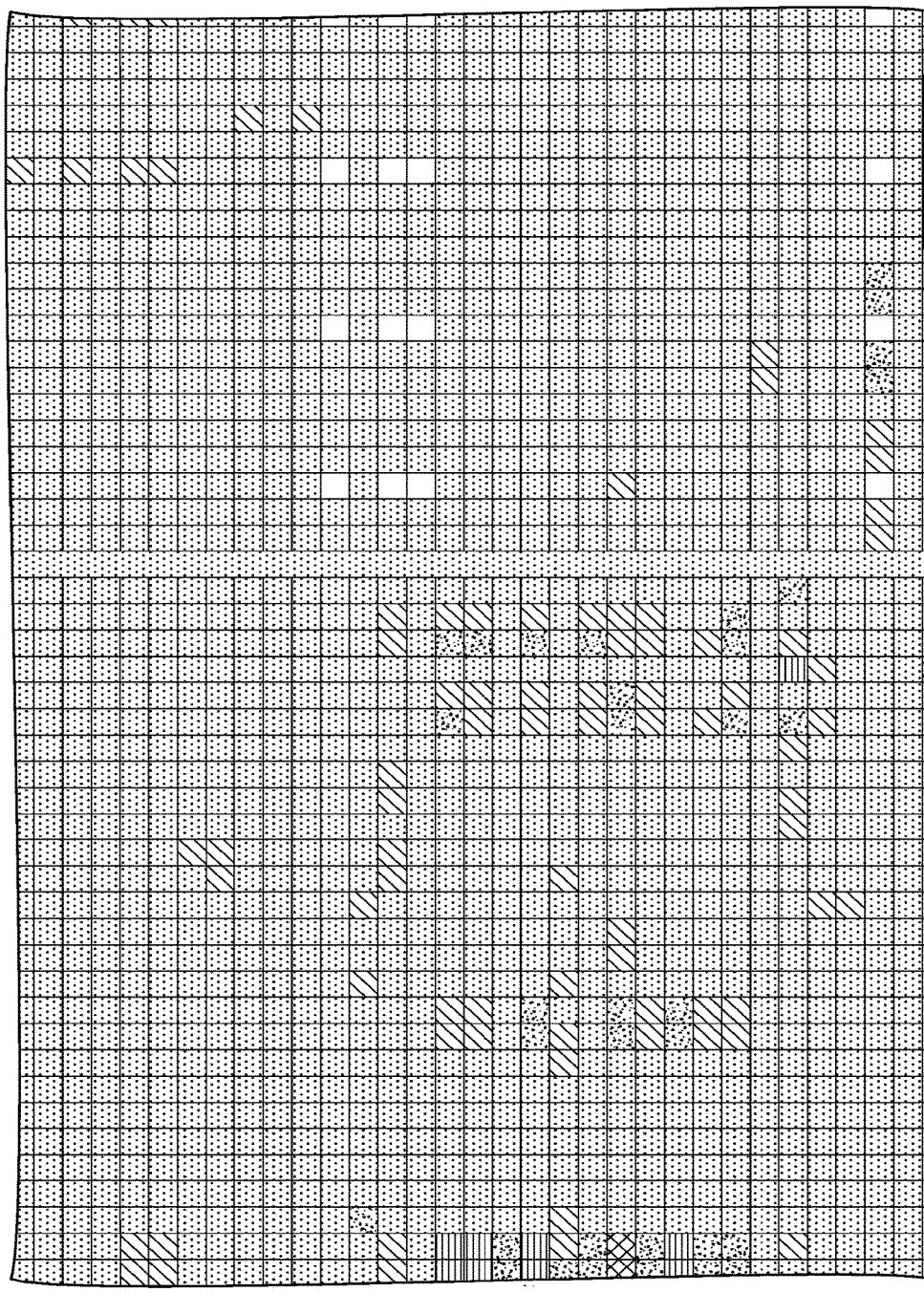
Figure 5H:
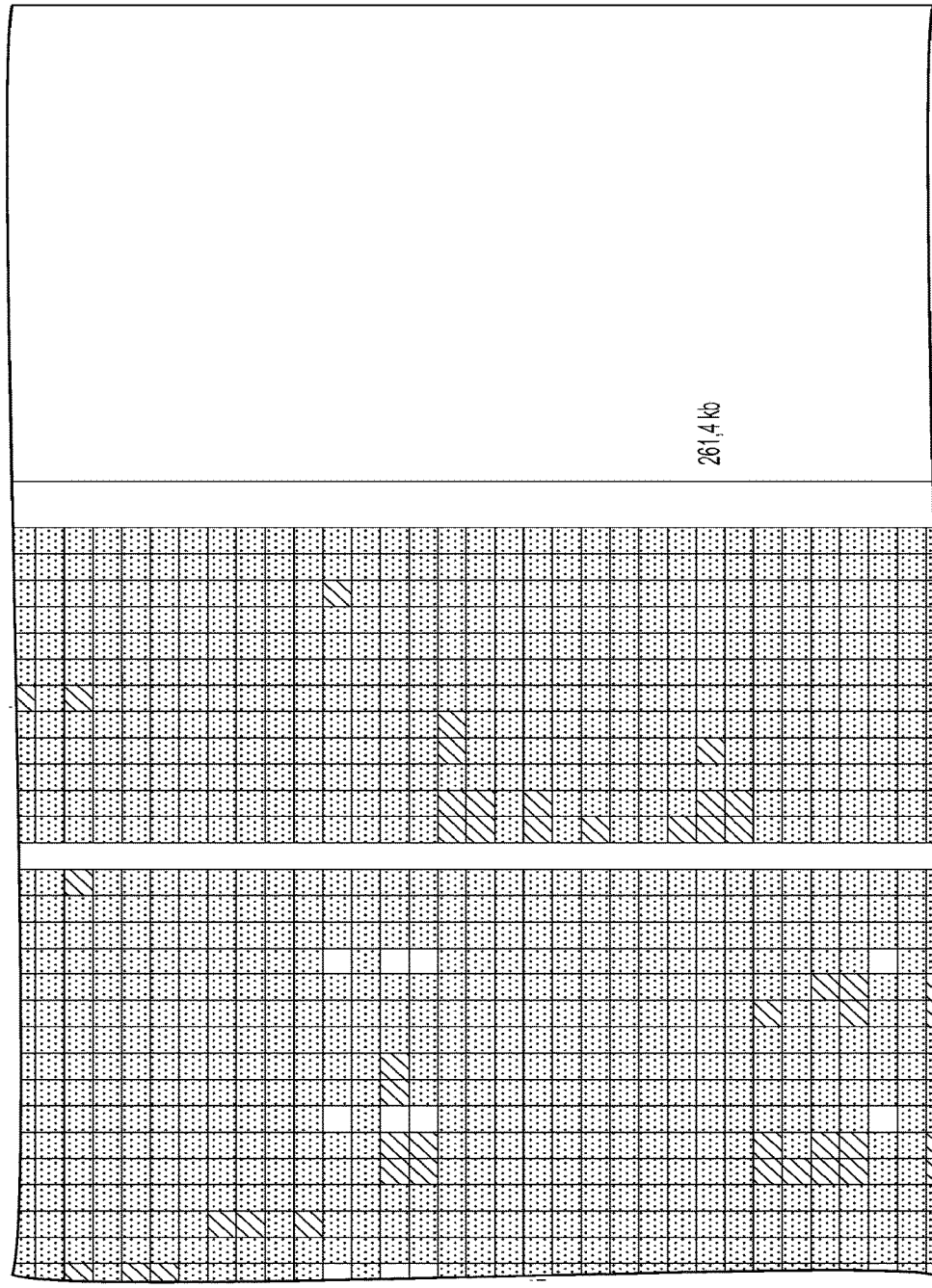
Figure 5I:
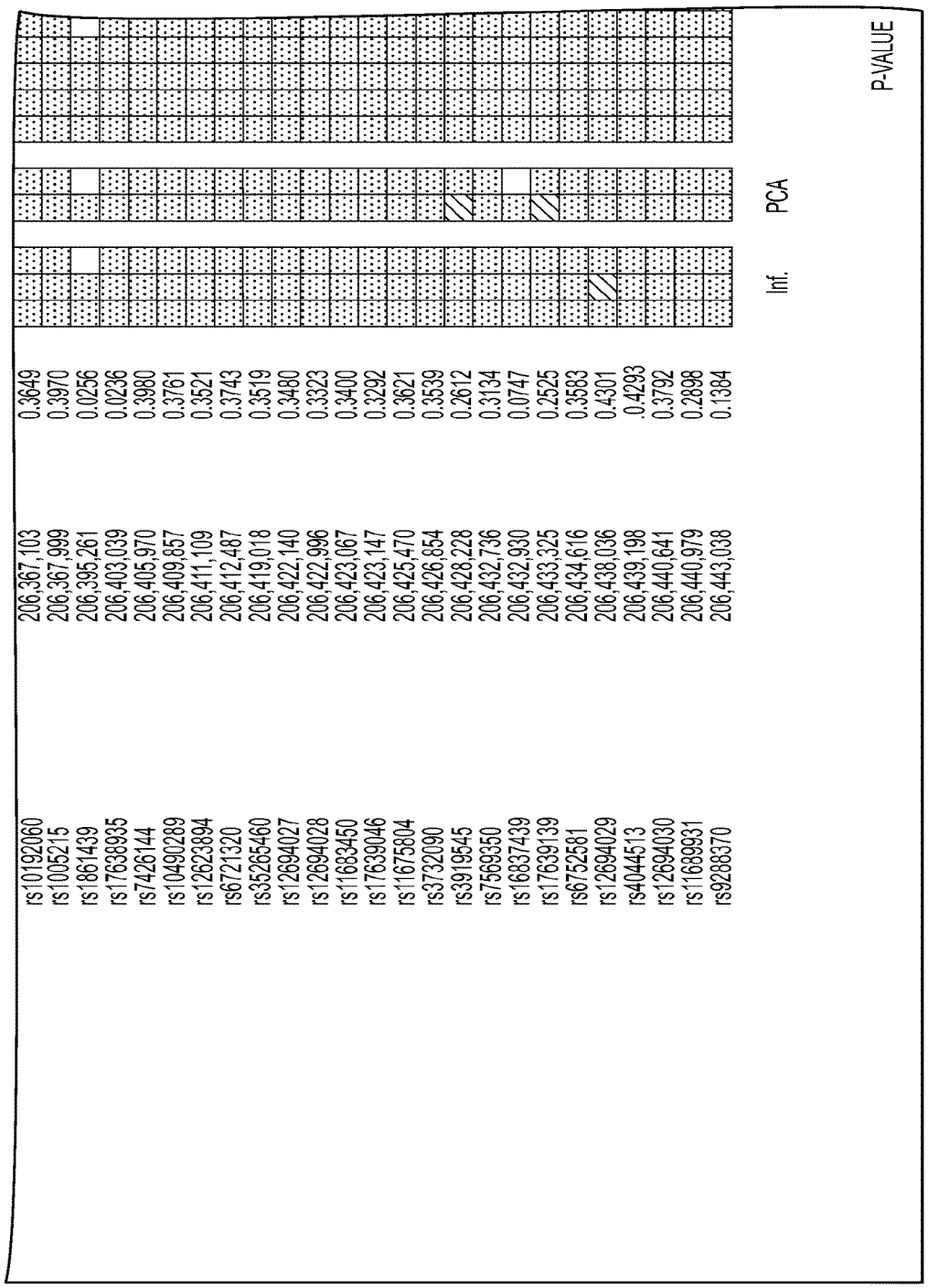
Figure 5K:
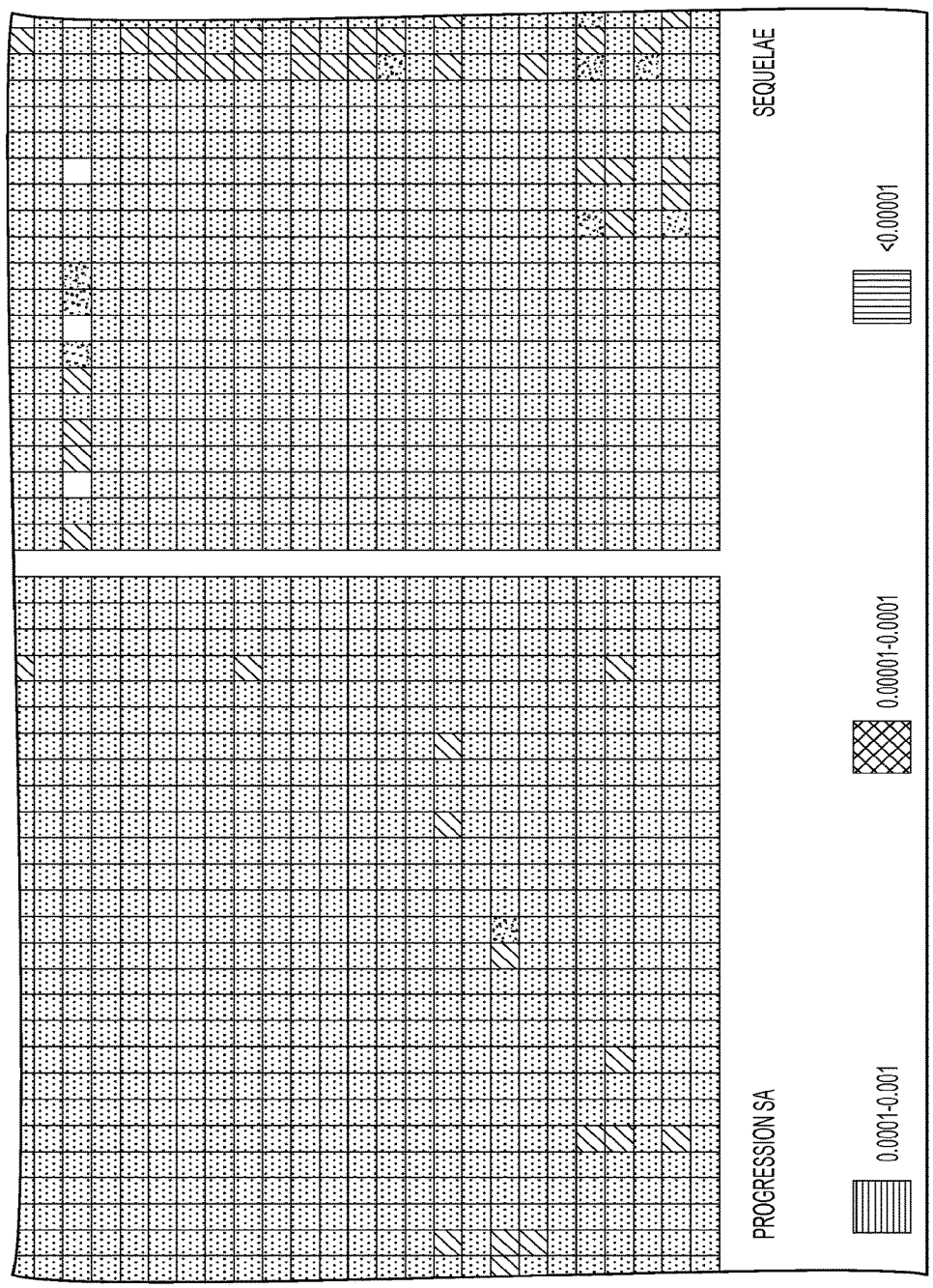
Figure 5L:
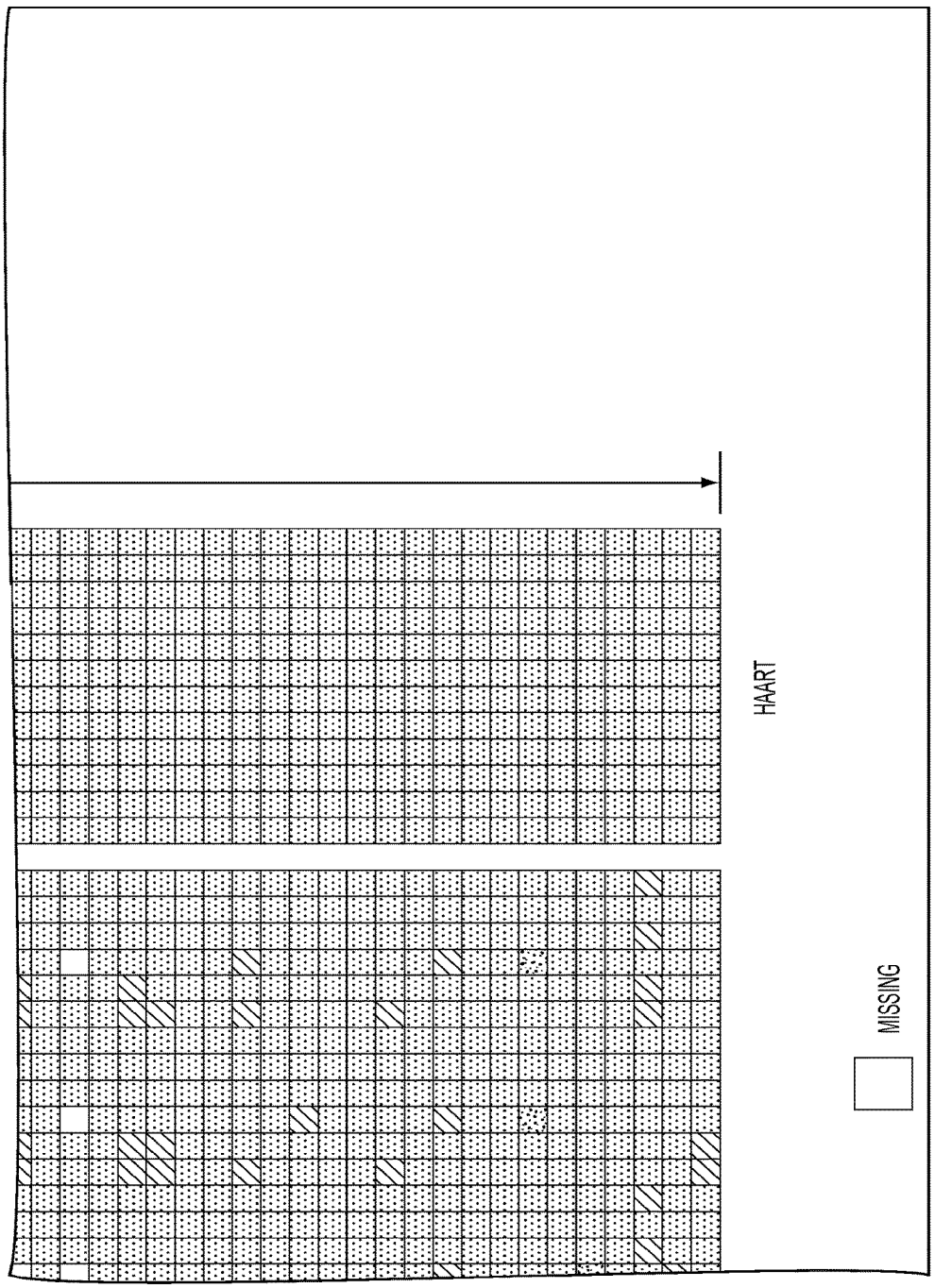

2.) MANHATTAN plots are computed as well to compare all genotyped SNPs for any single test (FIG. 3).

3.) The HIGHWAY feature is a dynamic human chromosome browser that scrolls in a 3-dimensional moving video mode above a "chromosomal surface" whereby the baseline transversal axis is a list of tests (e.g., 123 ARG association tests for Group A in Table 3) and the longitudinal axis lists the SNPs ordered along each of the 22 human autosomes. Embodiments of the longitudinal axis units can be distance along the chromosome in number of SNPs, nucleotide base pairs, centimorgans or in recombinant frequency.

Blocks rising out of the surface reflect −log p-values (for $p<10^{-4}$, $10^{-3}$ or $10^{-2}$ depending on the user-controlled settings, to remove noise of non-significant results), while the color intensity reflects the QAS. Certain colors, such as red, of the bar may indicate disease susceptible (QAS>1.0) SNP-allele association outcomes, and other colors, such as green, may indicate SNP-allele association suggesting resistance to disease (QAS<1.0). The browser allows the user to navigate above the chromosome surface and view more detailed association statistics (p-value, QAS) as well as SNP information (rs-number, coordinates, MAF etc.) by placing the mouse pointer atop the bar for any SNP-test combination. A user can search and locate any single region of interest by SNP rs-number, gene name, chromosome coordinates or the threshold for −log p-value. This search can be performed within the currently selected chromosome or whole genome-wise. Therefore, a region identified as a potential hit in any other study, whether it includes the same SNPs or not, can be targeted and inspected for neighboring or related associations in the region.

For any region of interest the user may be able to access additional information and insight as follows:

4.) GWATCH can produce a 2-Dimensional Snapshot (2D-SNAPSHOT), an ordered list of SNPs (e.g., ~80 SNPs at 4 kb average density) and test results (e.g. 123 tests for Group A, Table 2) equaling ~10,000 SNP-test combinations. The 2D-SNAPSHOT of a selected genomic region may be a heat plot indexed by the p-values from p>0.05 (such as light grey) to deep richer colors for decreasing p-values, assuring that significant region clusters are more densely colorful (FIGS. 5A-5L). The human brain, trained to understand genetic analysis can grasp the visuals provided in certain embodiments herein almost instantly.

Figure 6A:
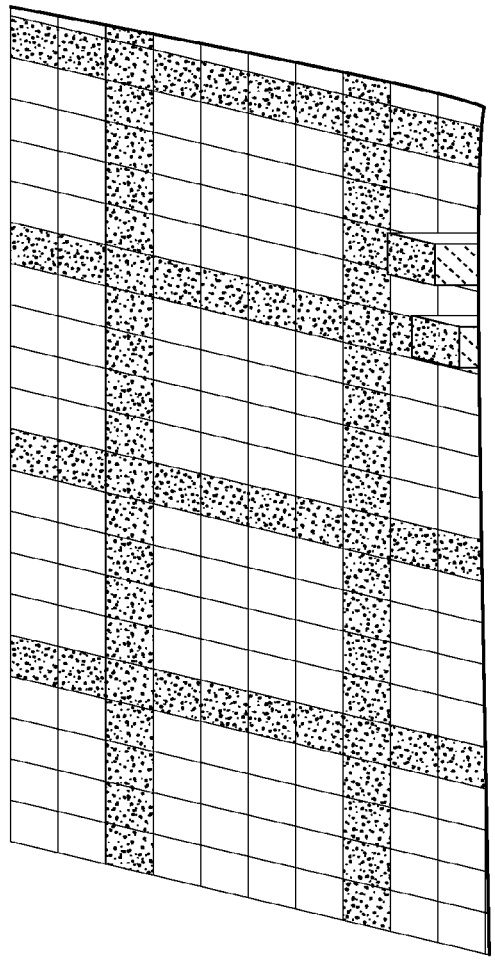
FIGS. 6A-6P shows an exemplary 3D-SNAPSHOT of selected region illustrating significant p-values (block height), QAS-based direction (color: green for QAS<1.0, red for QAS>1.0) and QAS-based strength (color intensity) of association for linked SNP alleles.
Figure 6C:
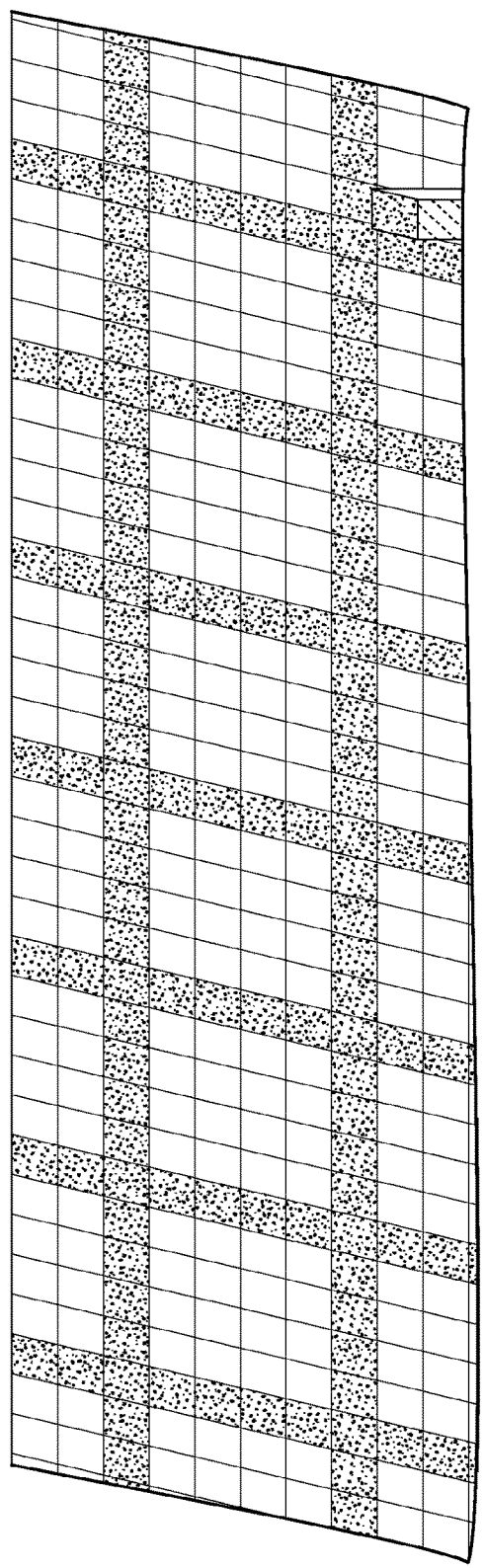
Figure 6D:
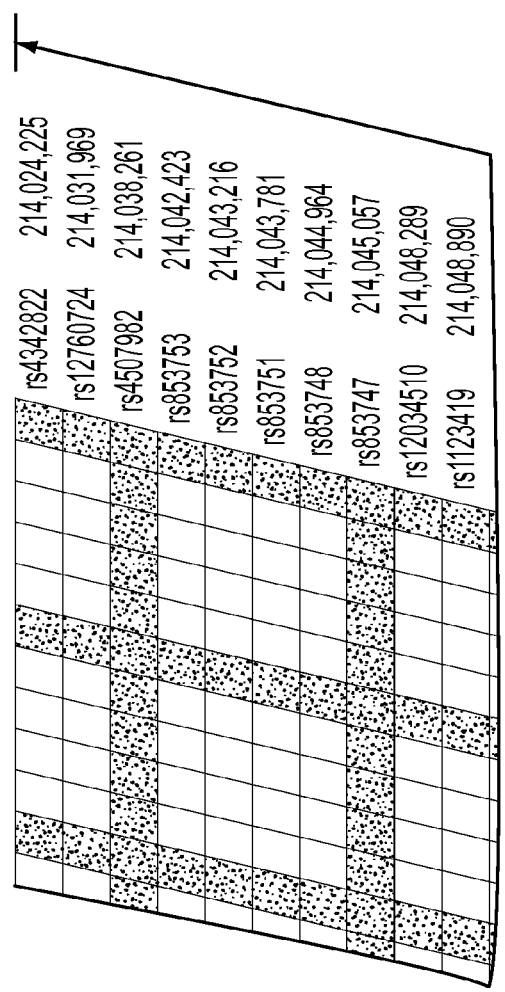
Figure 6E:
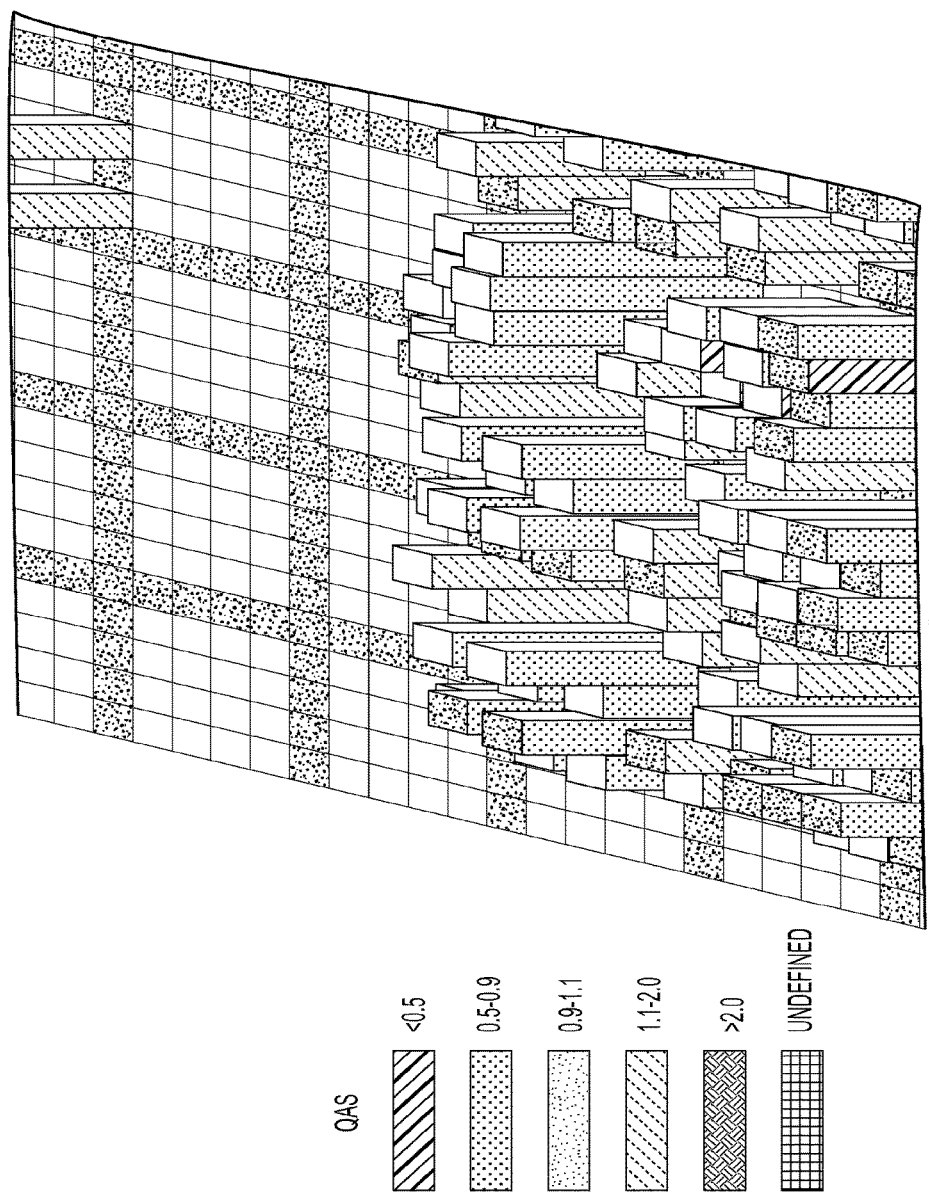
Figure 6F:
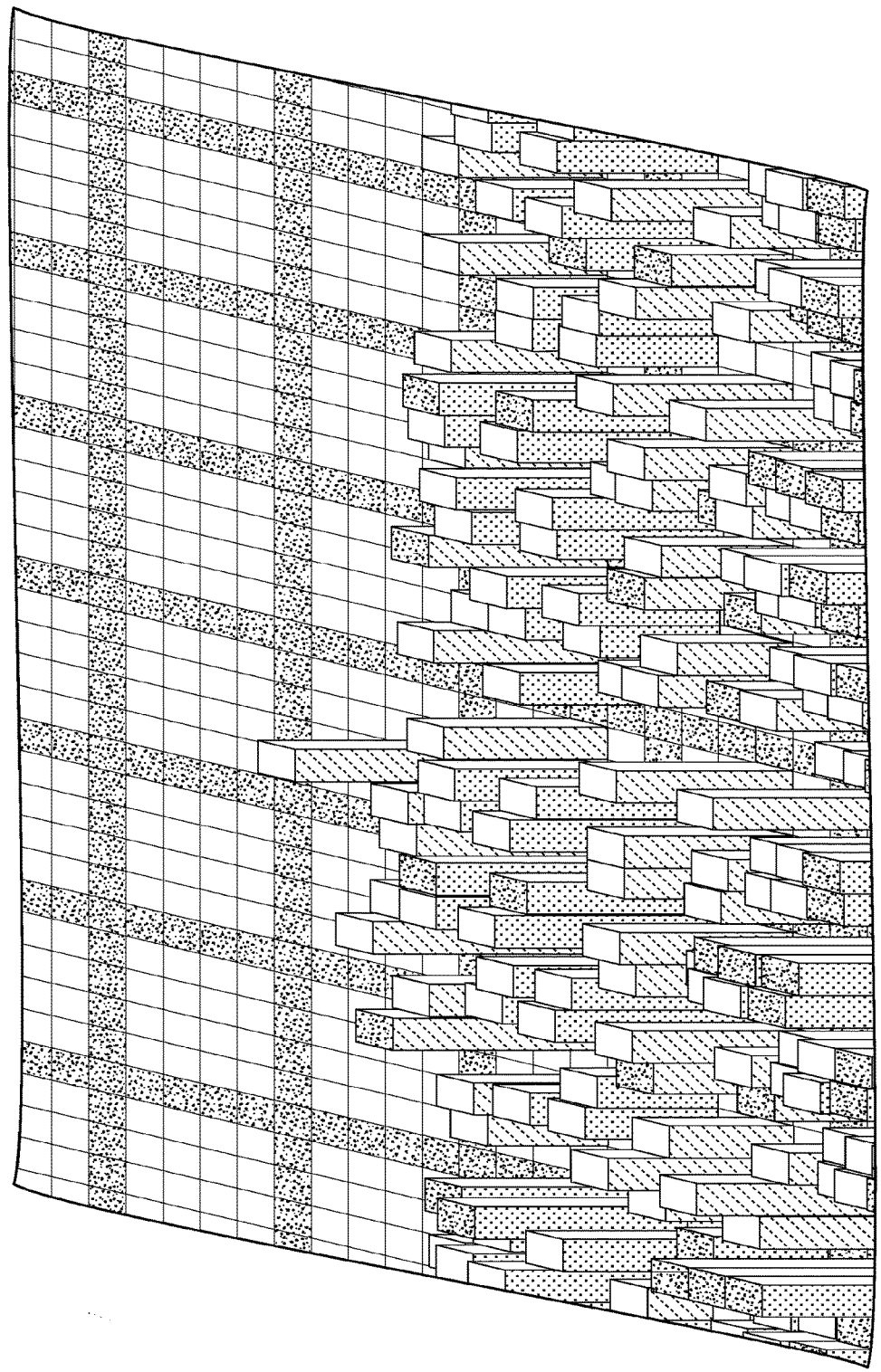
Figure 6G:
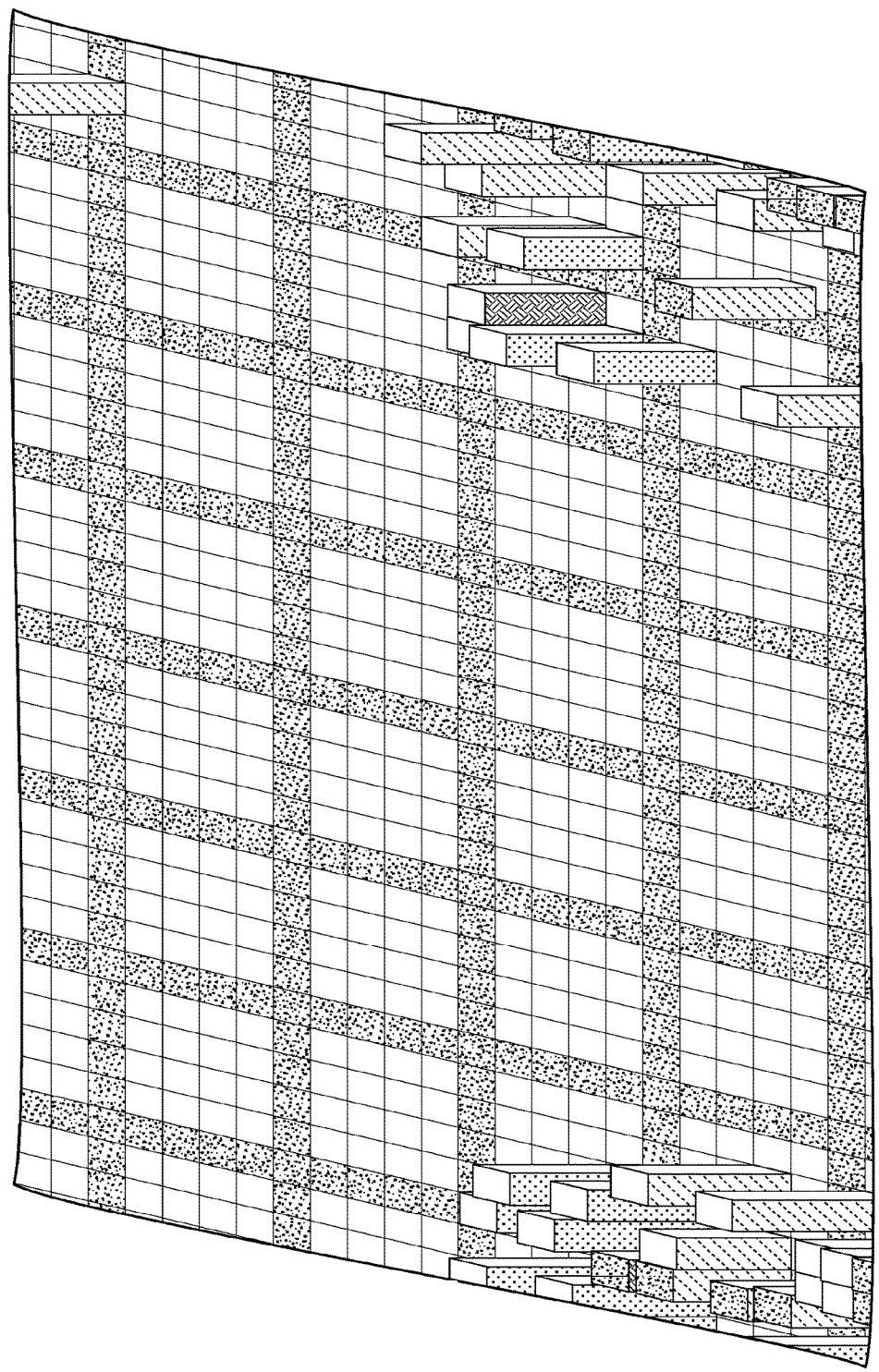
Figure 6H:
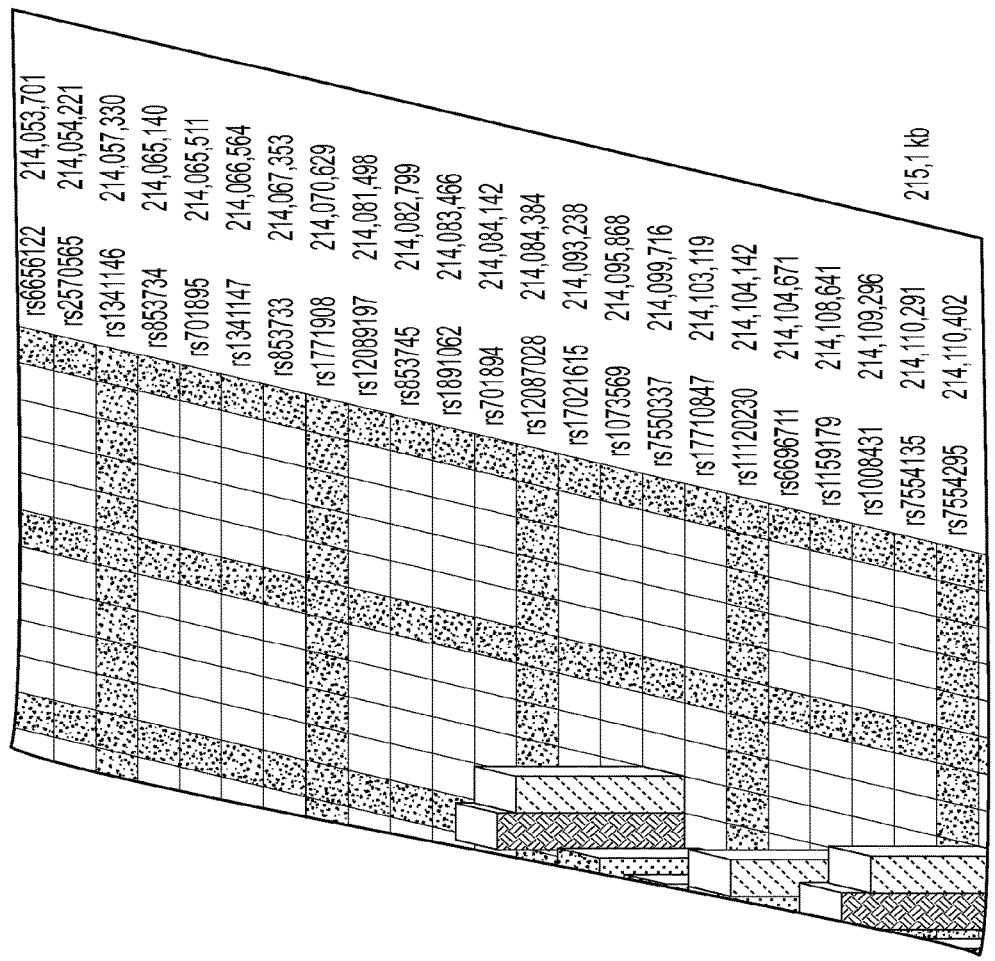
Figure 6I:
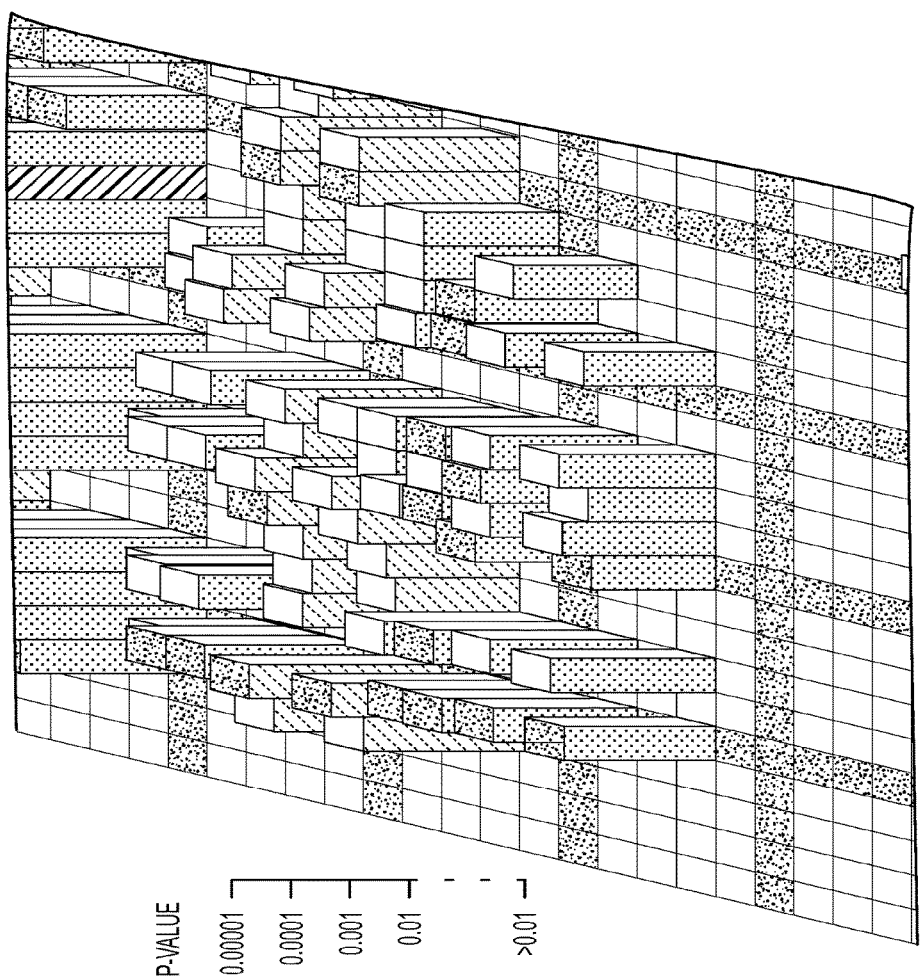
Figure 6J:
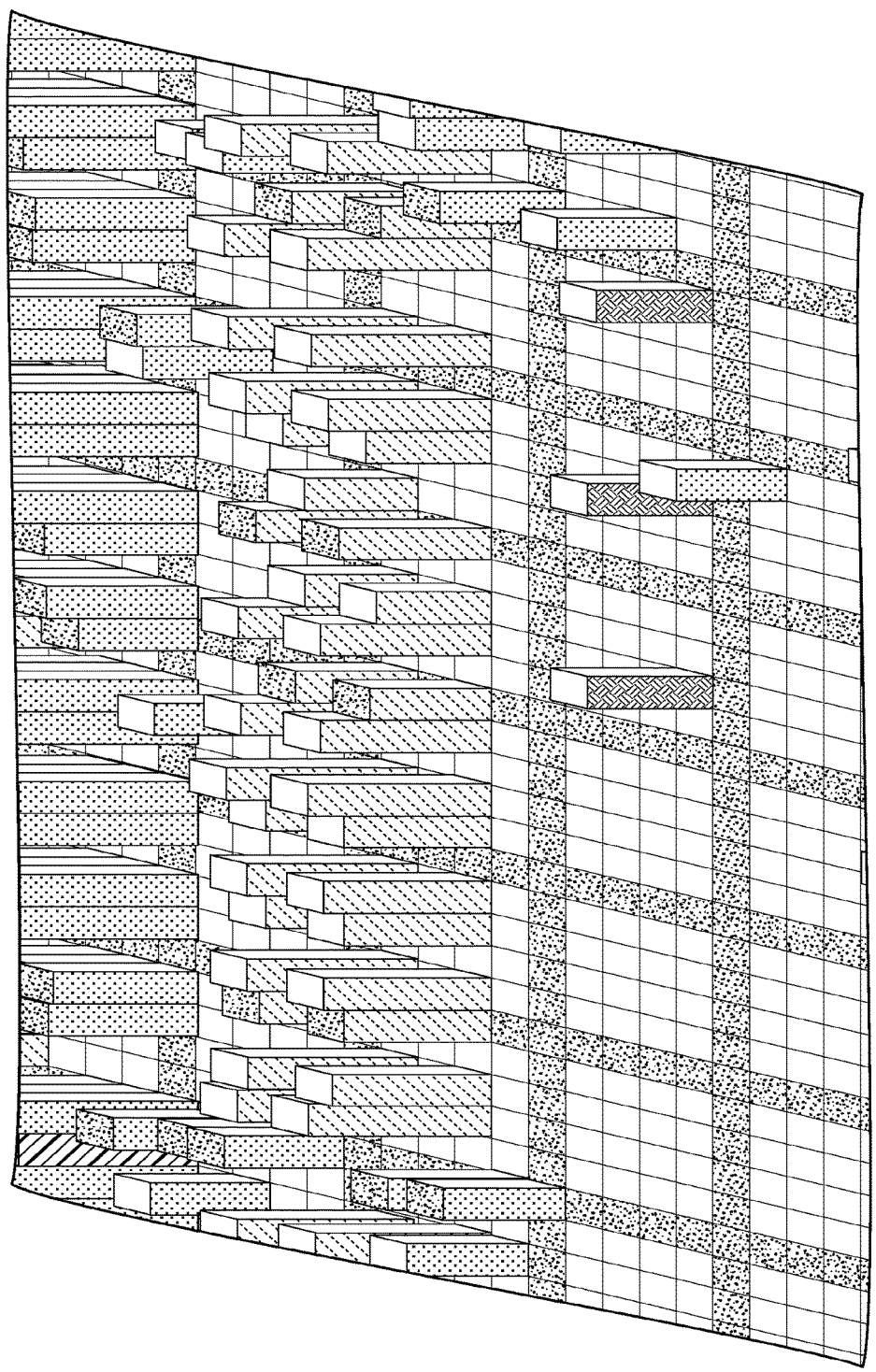
Figure 6L:
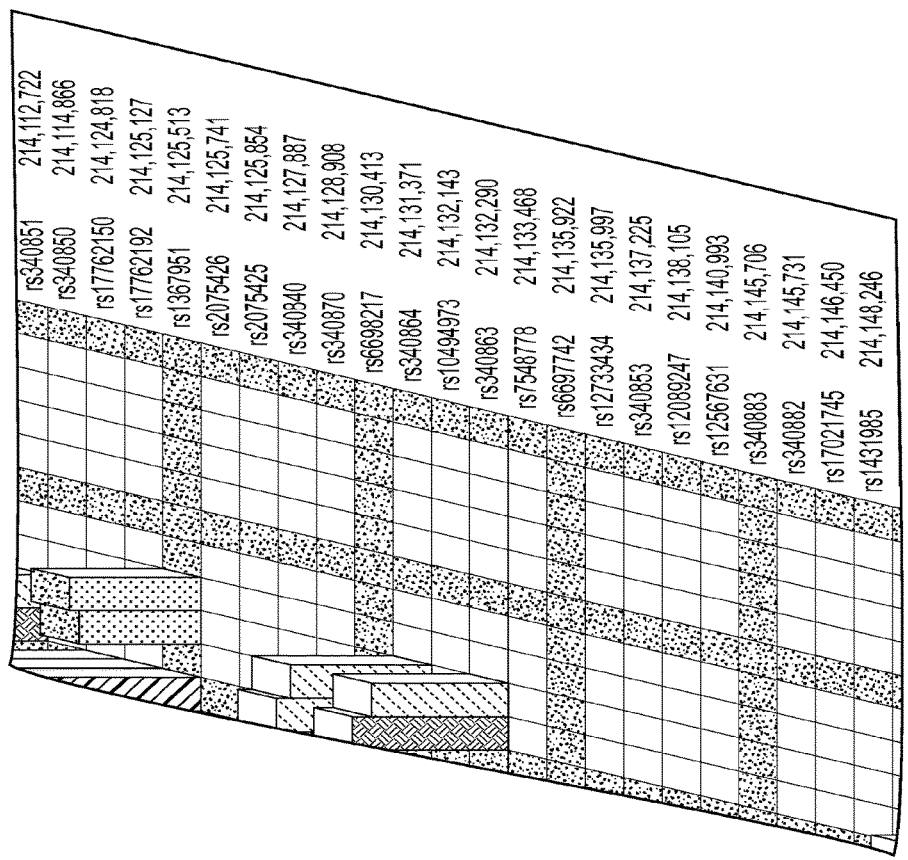
Figure 6M:
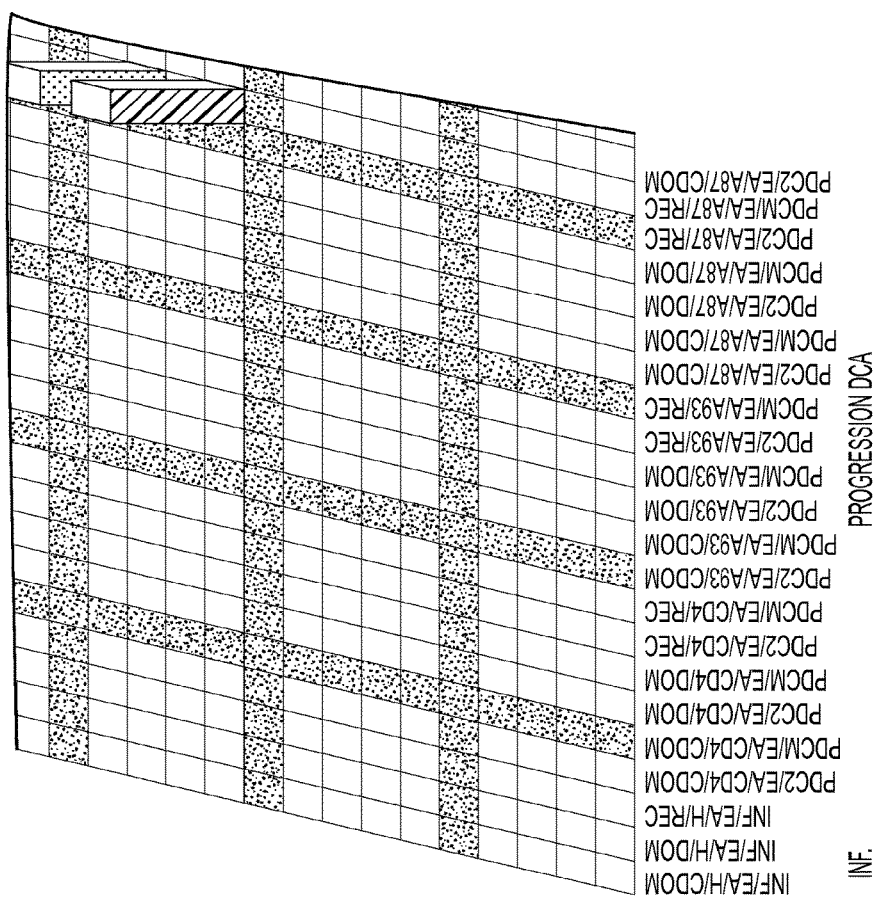
Figure 6N:
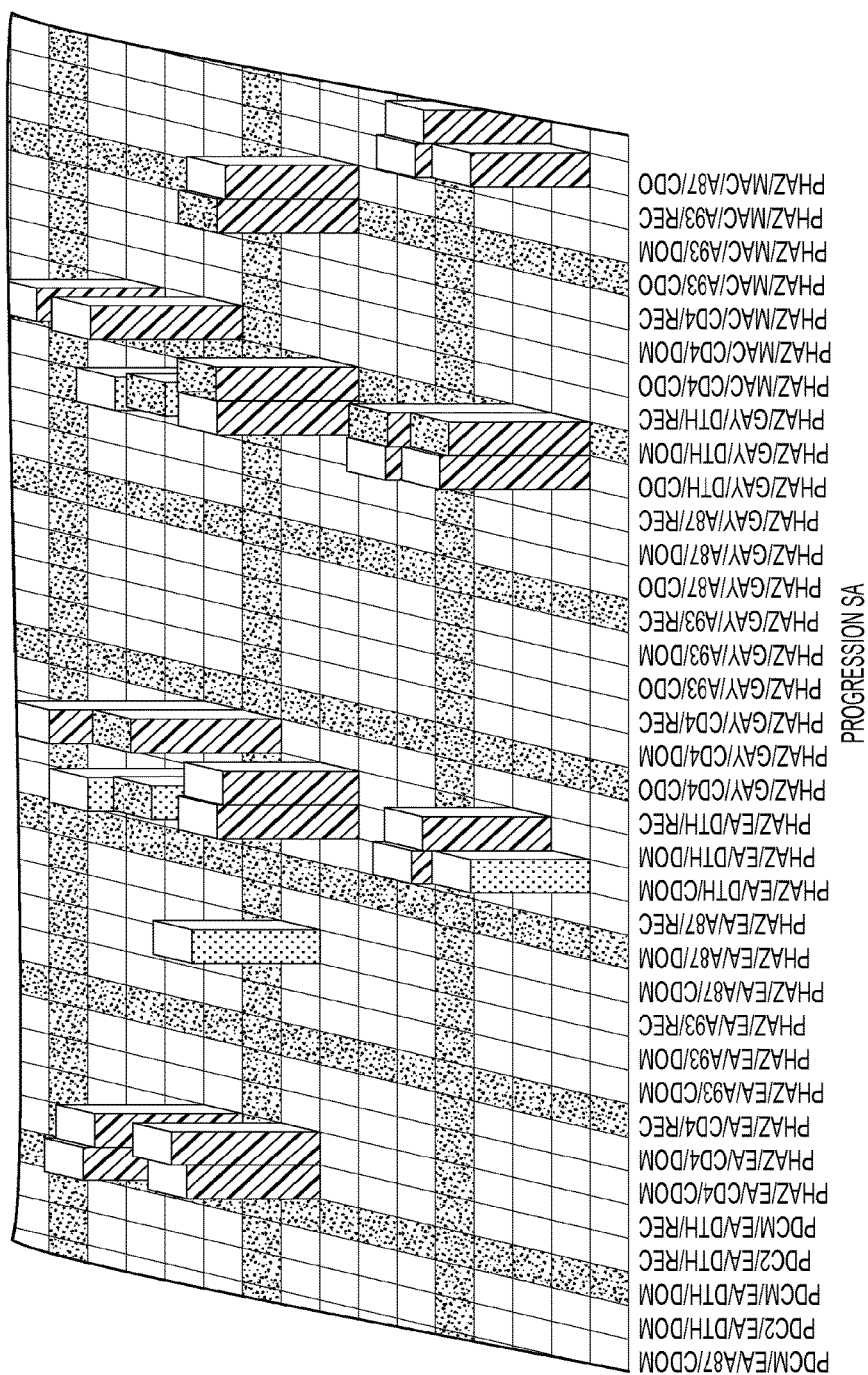
Figure 60:
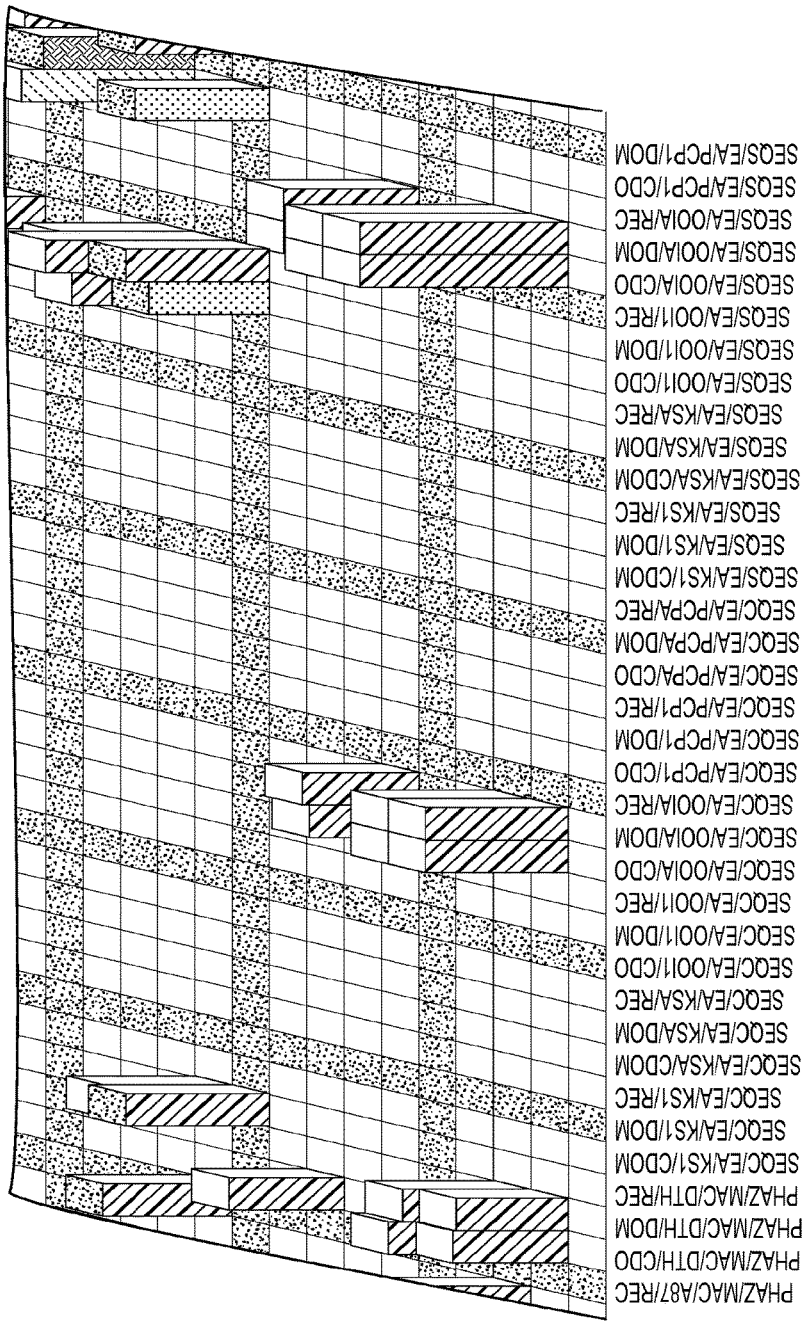
Figure 6P:
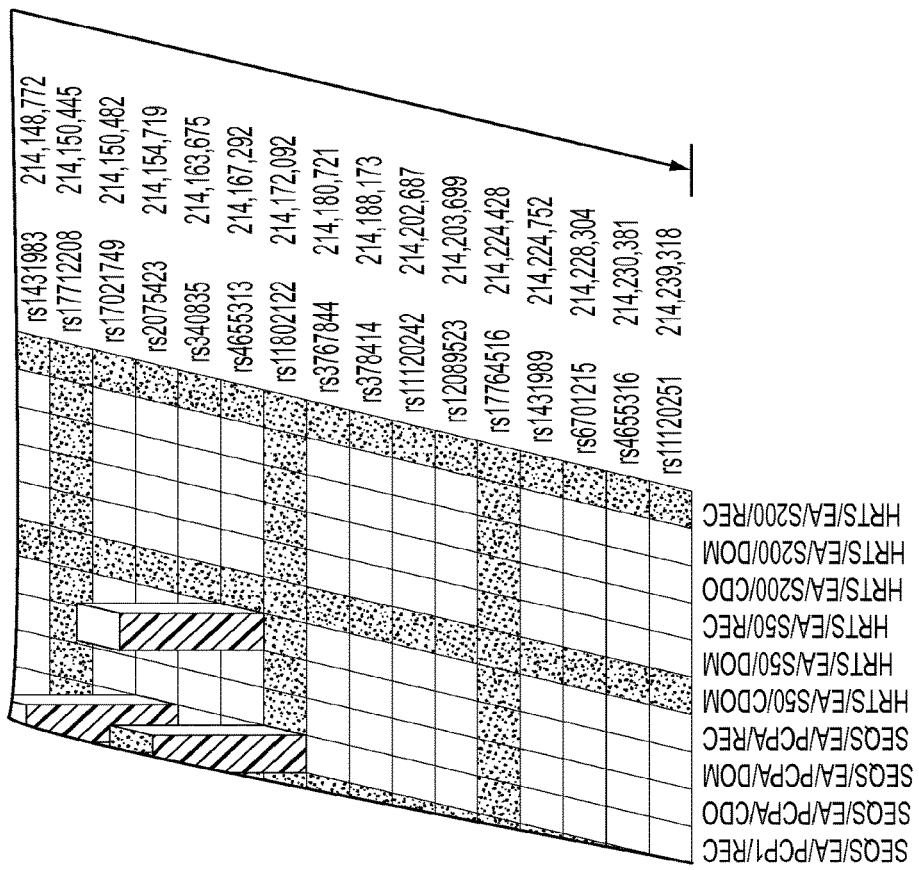

5.) GWATCH may also display 3-Dimensional Snapshot (3D-SNAPSHOT) of a selected region similar to the view in the dynamic HIGHWAY, but labeled with SNP rs-number, chromosome coordinates and MAF. FIGS. 6A-6P shows a 3D-SNAPSHOT of the region that includes described AIDS resistance gene PROX1.

6.) Since each SNP allele that is used to calculate individual QASs/p-values along the HIGHWAY browser is by default the minor allele in the study population, in some cases the colors (red and green) may be deceptive.

Figure 7A:
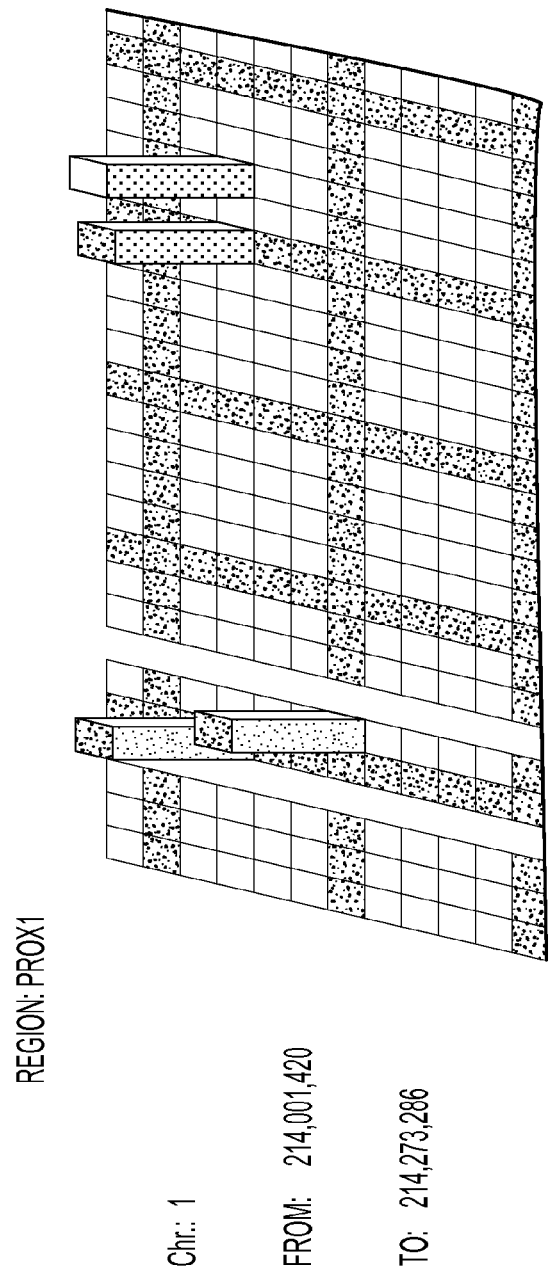
FIGS. 7A-7P shows an exemplary POLARIZED 3D-SNAPSHOT of associated gene data for selected region illustrating significant p-values (block height), QAS-based direction (color: green for QAS<1.0, red for QAS>1.0) and QAS-based strength (color intensity) of association for linked SNP alleles.
Figure 7B:
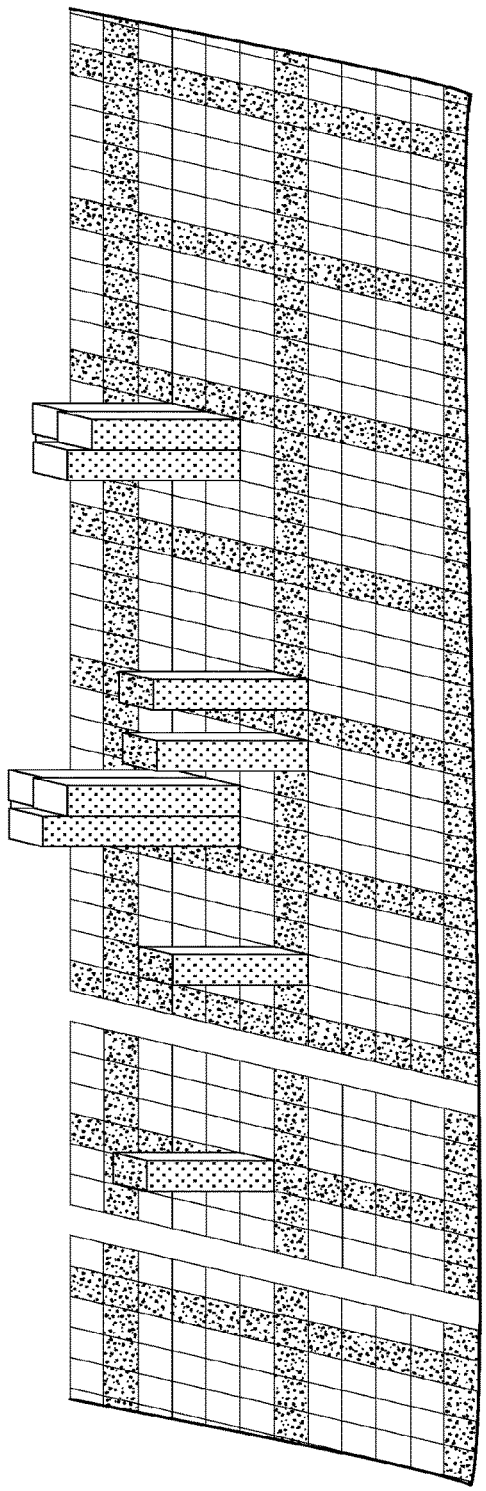
Figure 7C:
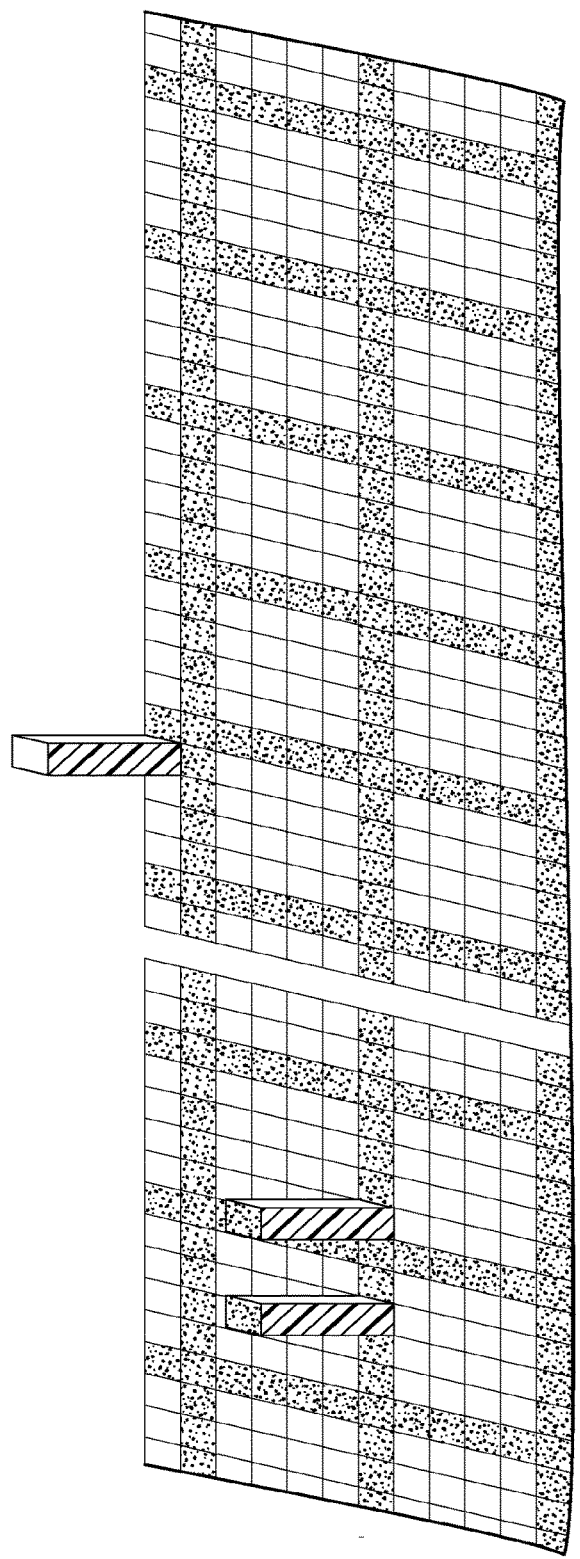
Figure 7D:
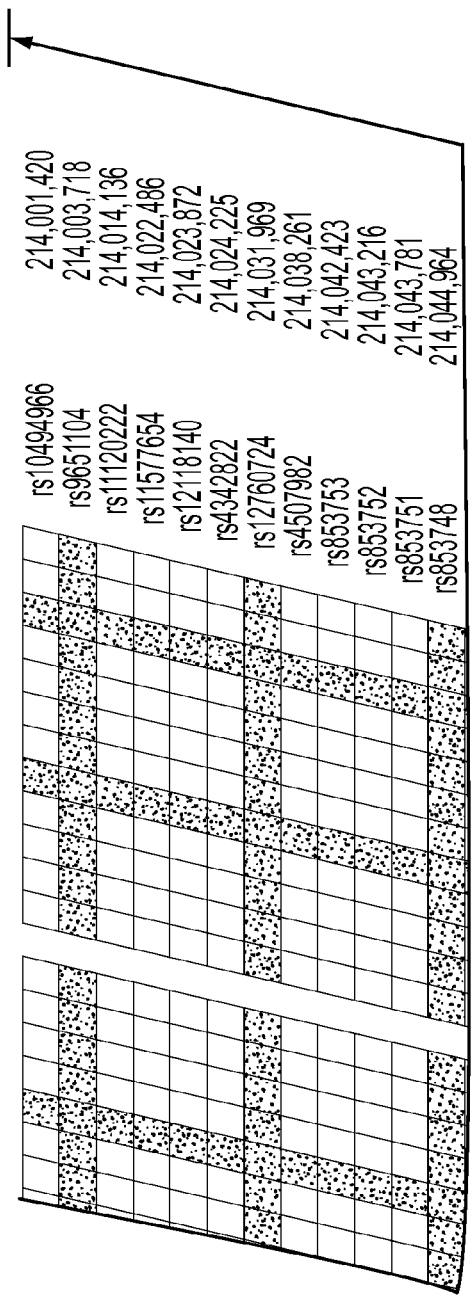
Figure 7E:
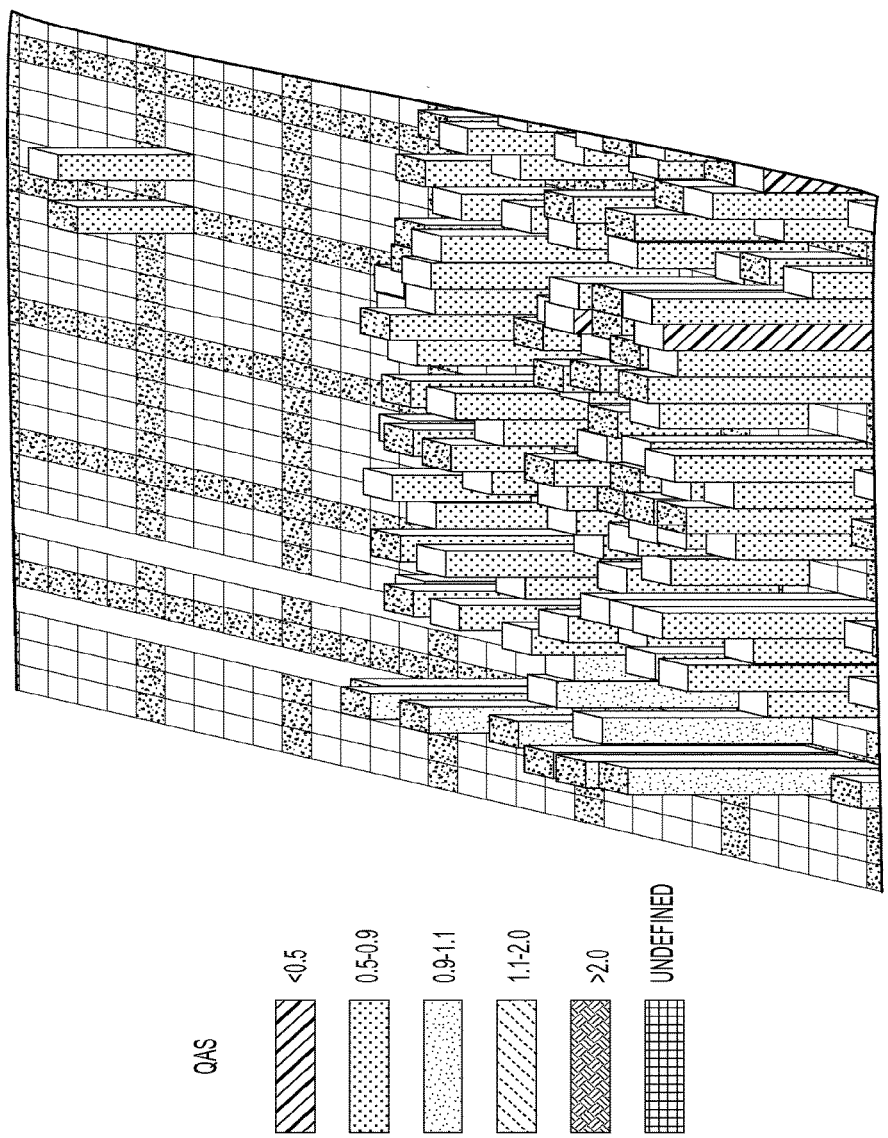
Figure 7F:
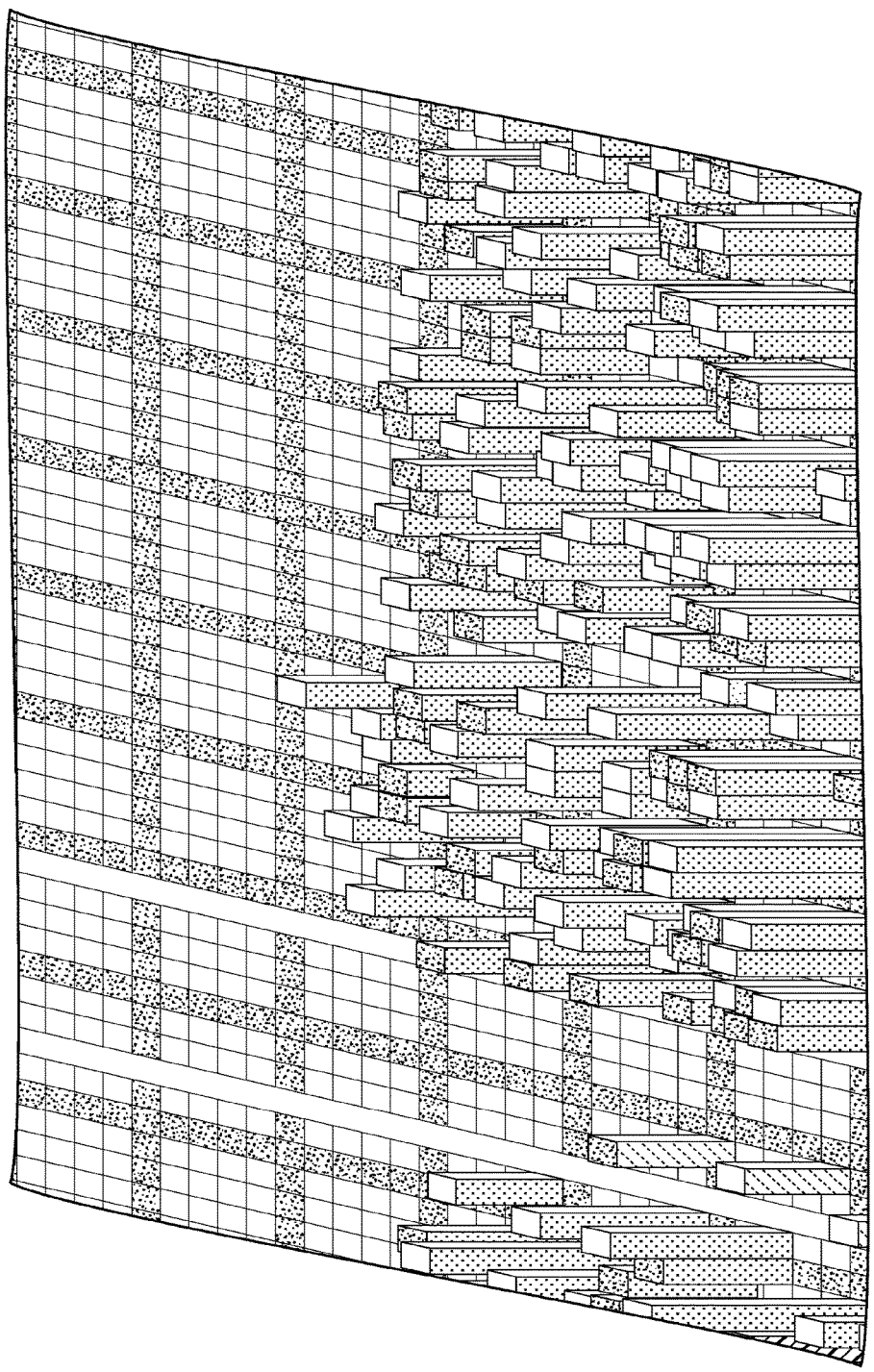
Figure 7G:
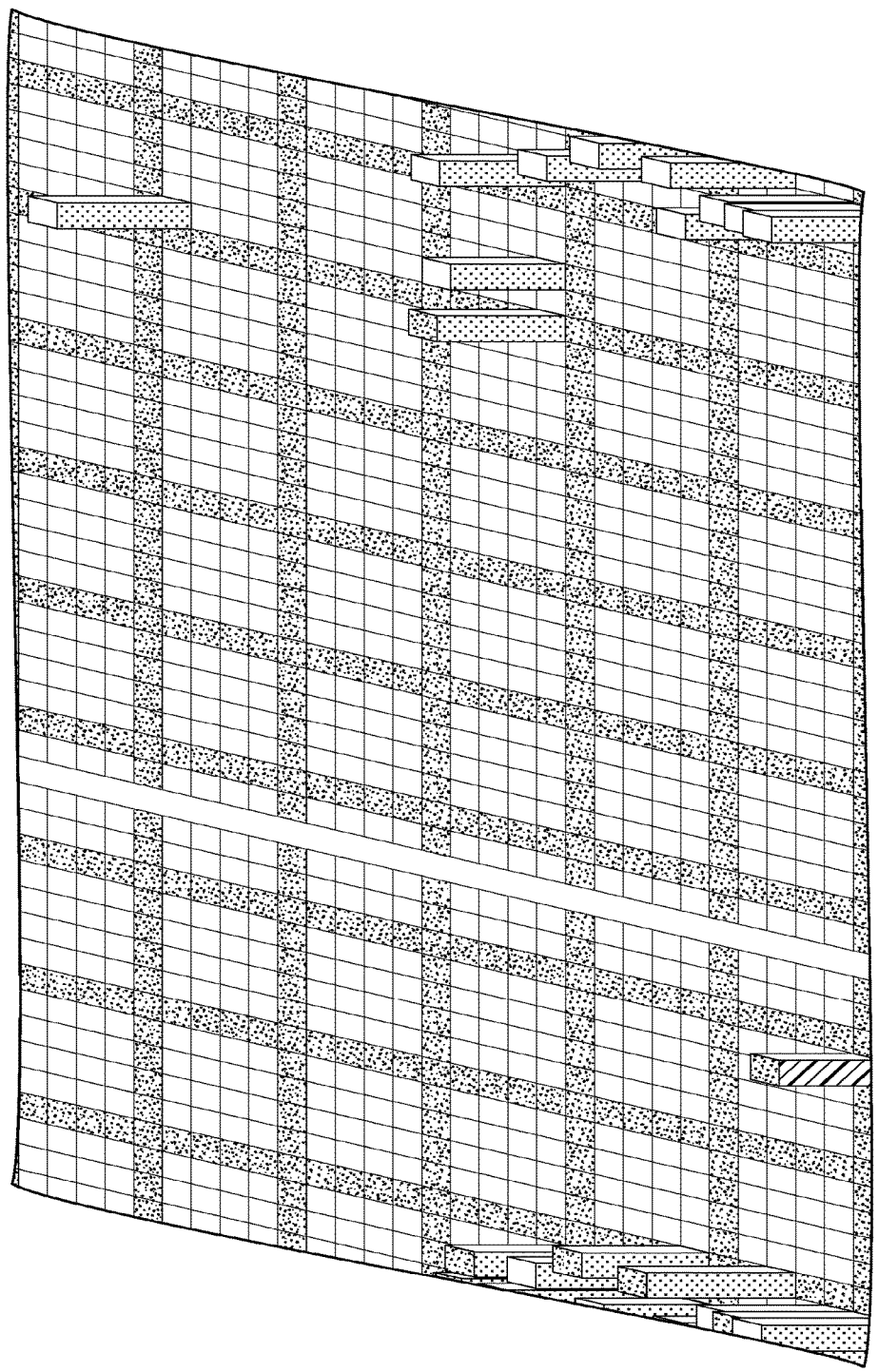
Figure 7H:
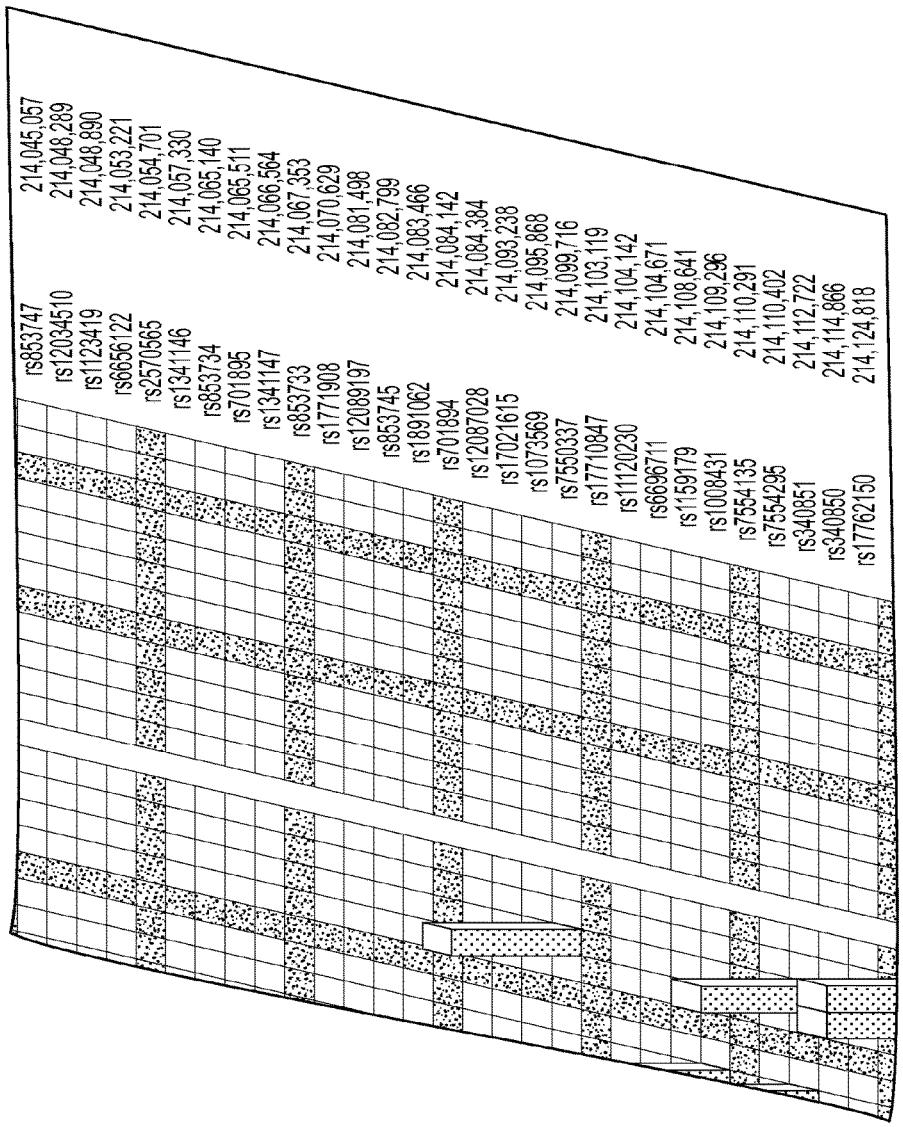
Figure 7I:
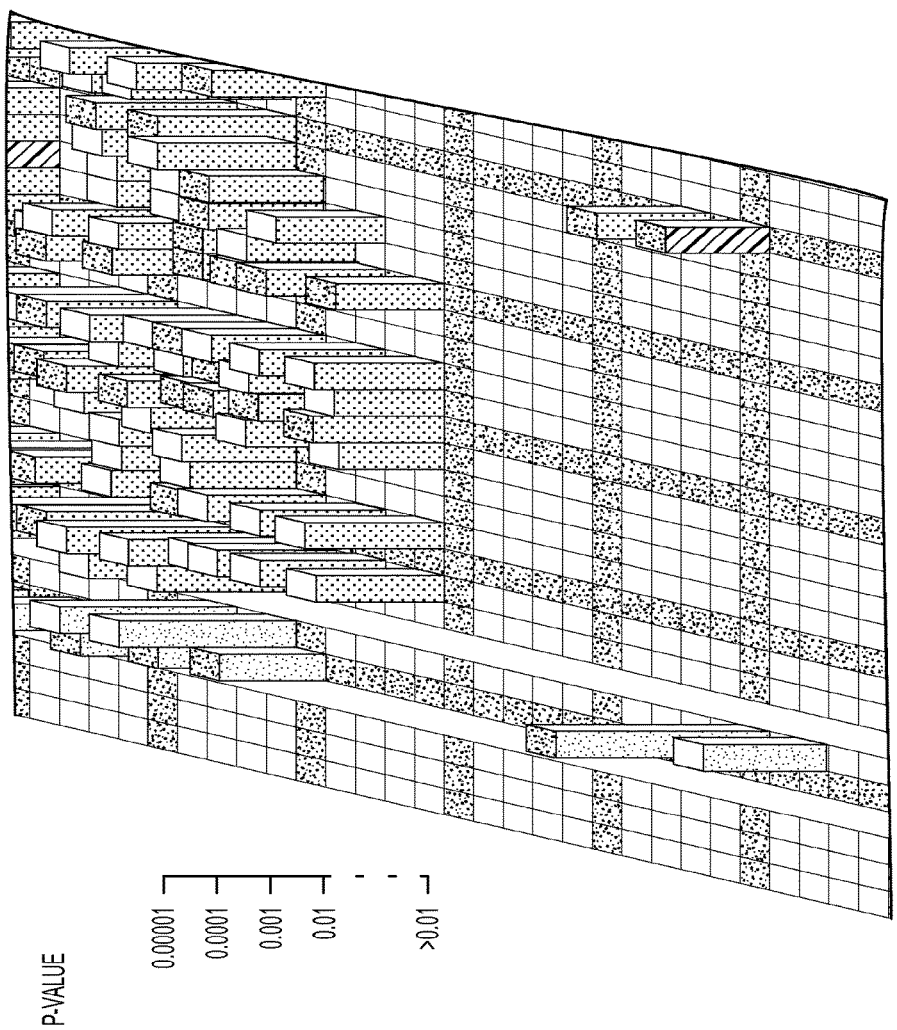
Figure 7J:
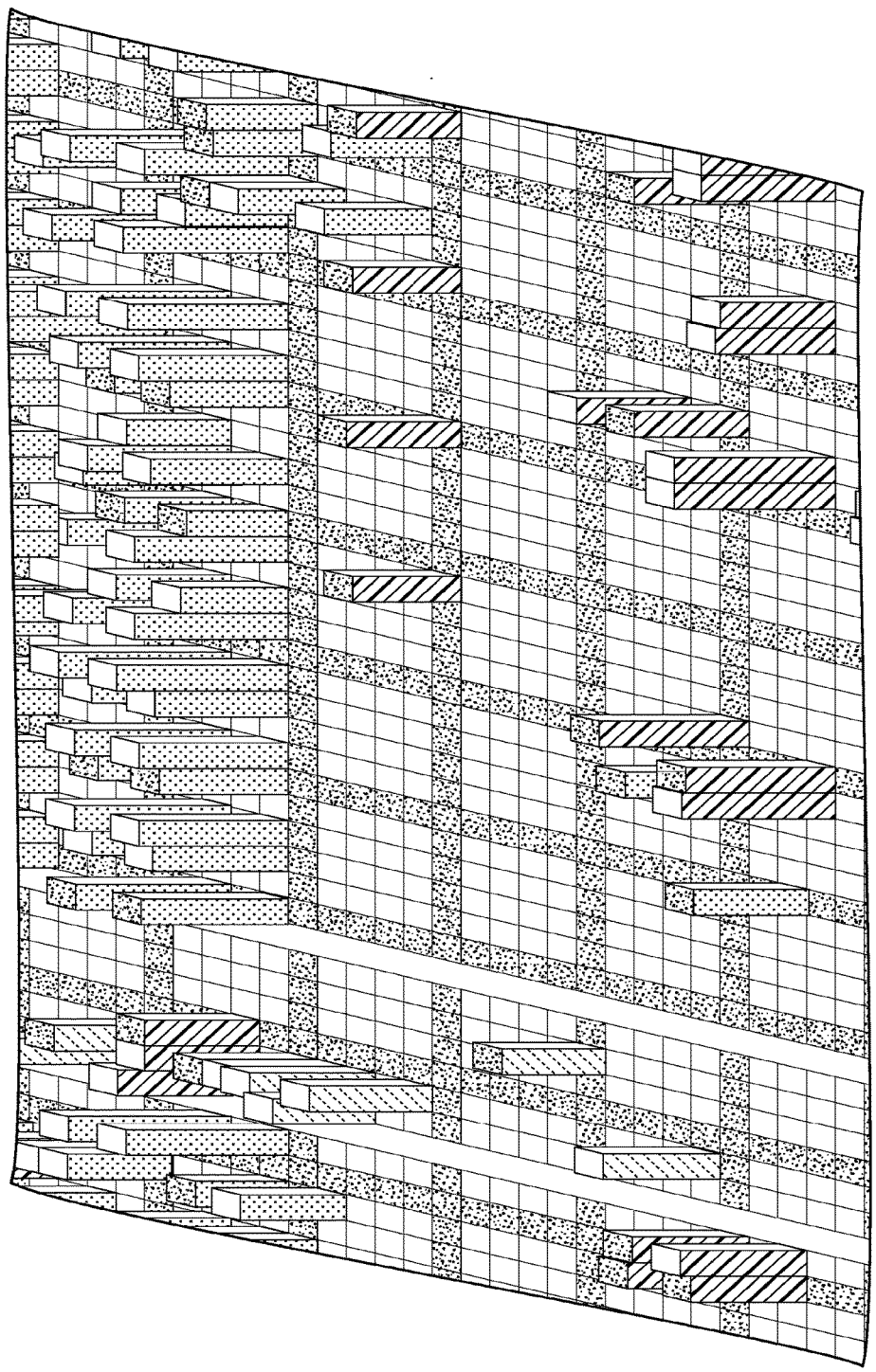
Figure 7K:
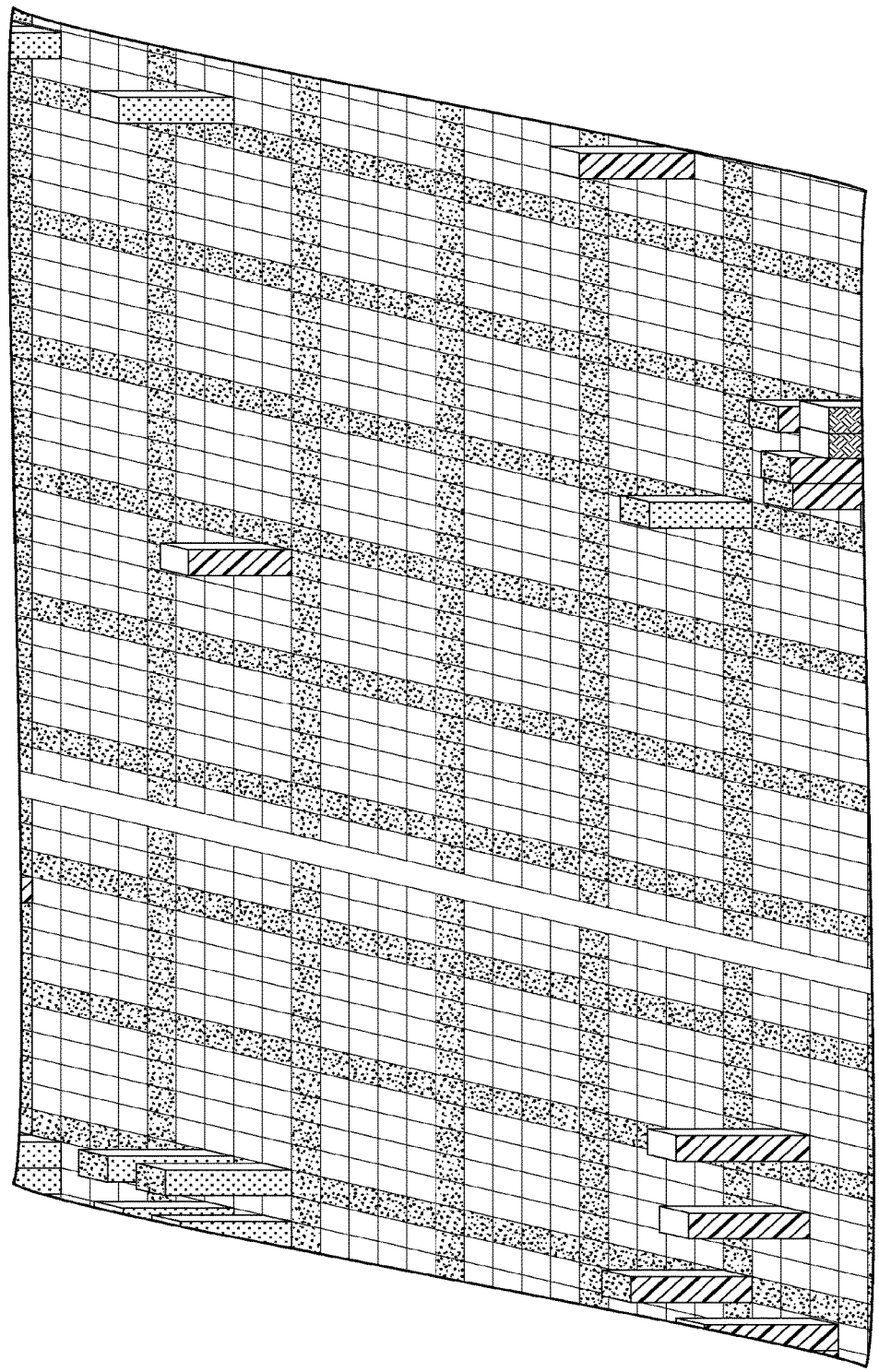
Figure 7L:
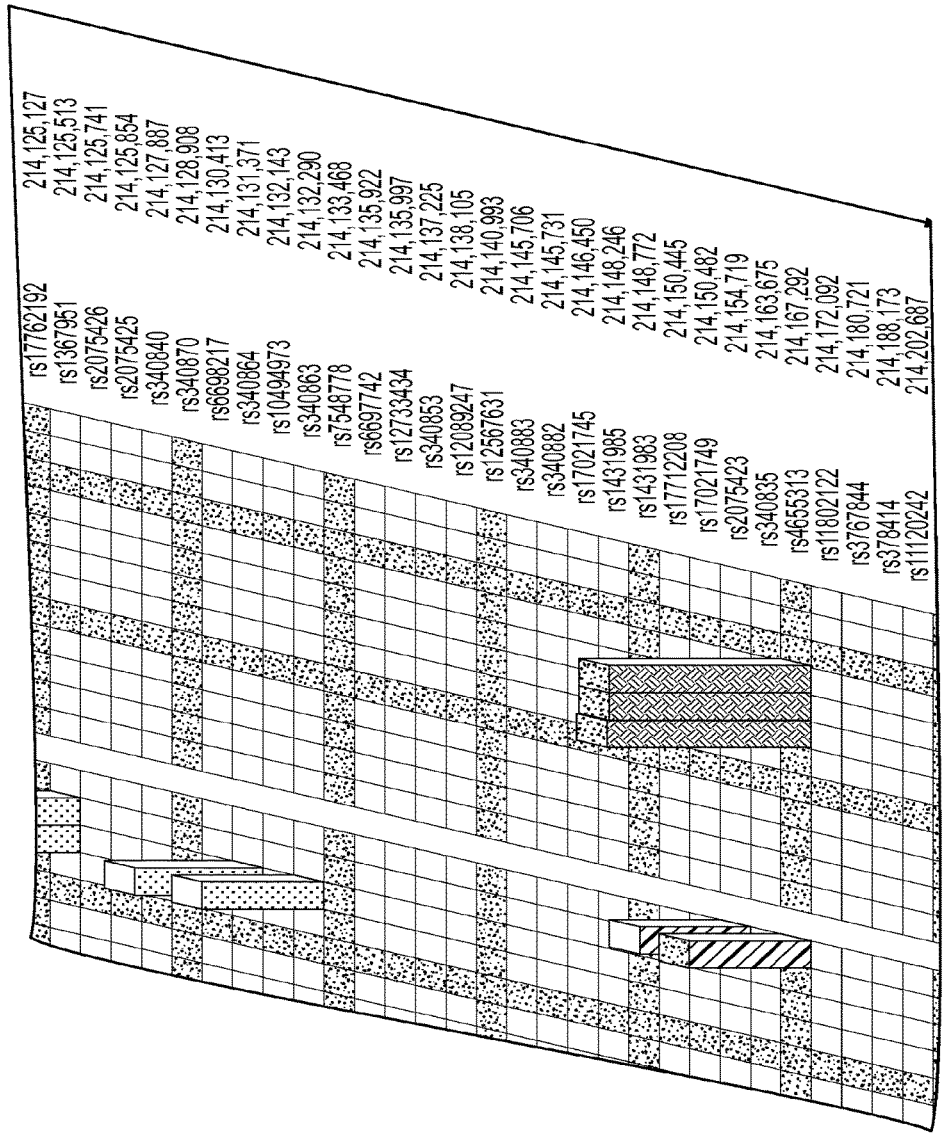
Figure 7M:
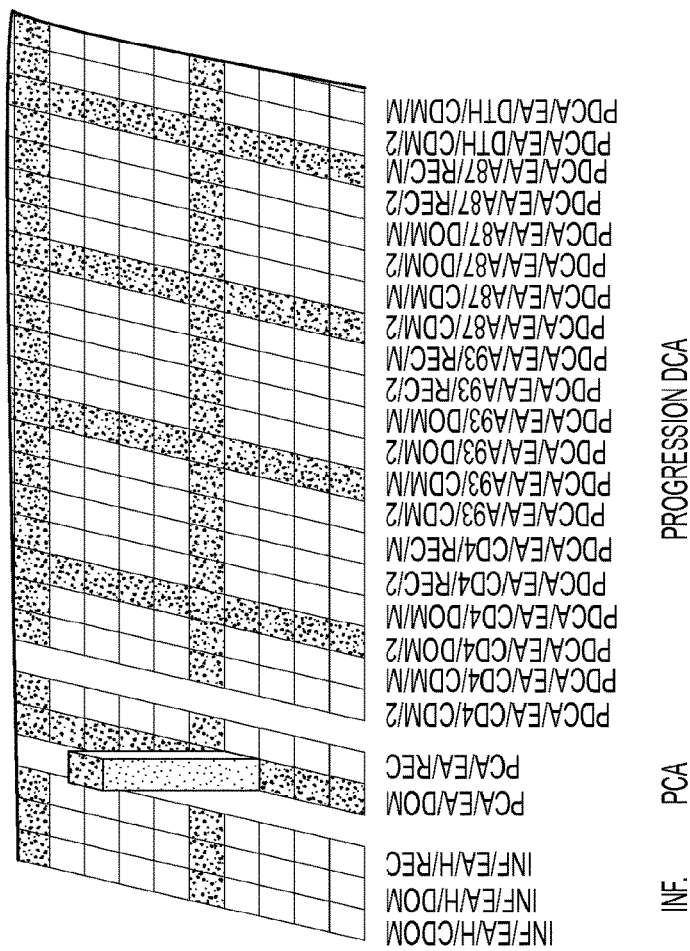
Figure 7N:
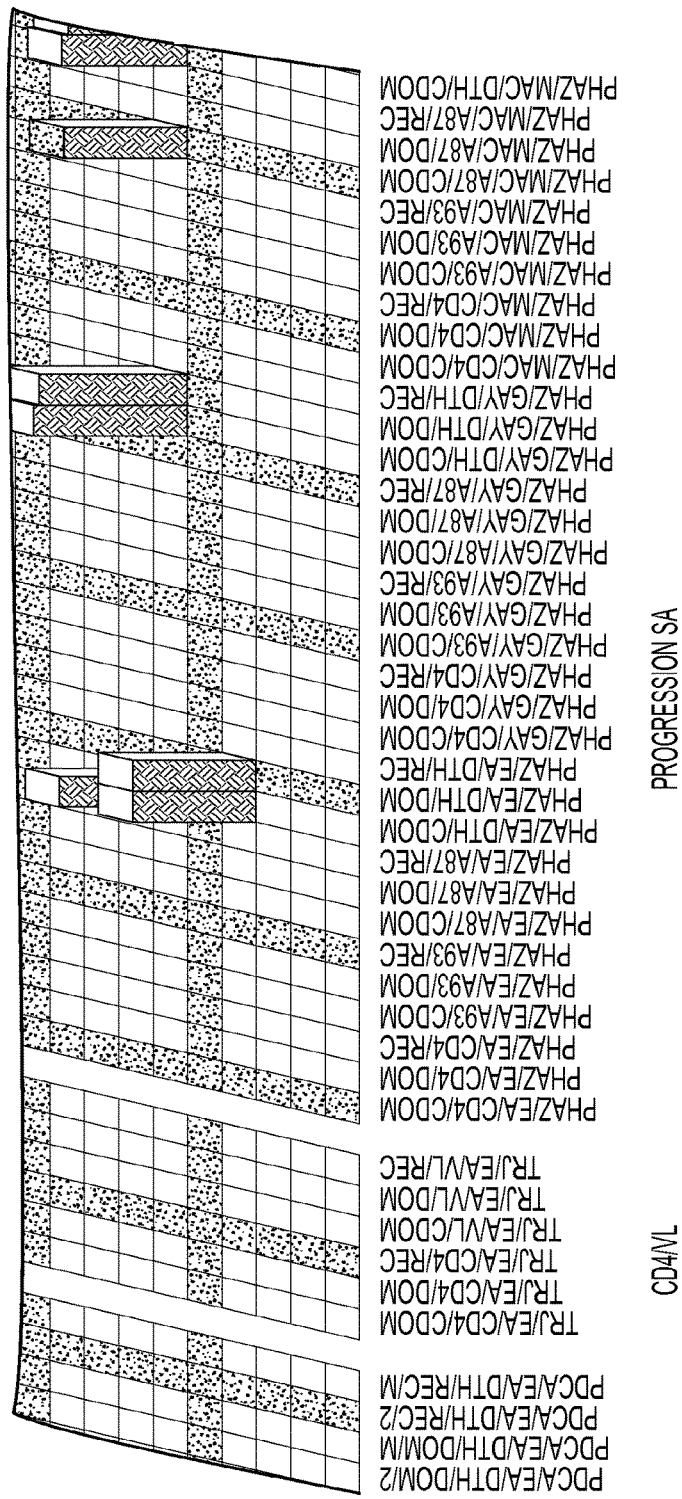
Figure 70:
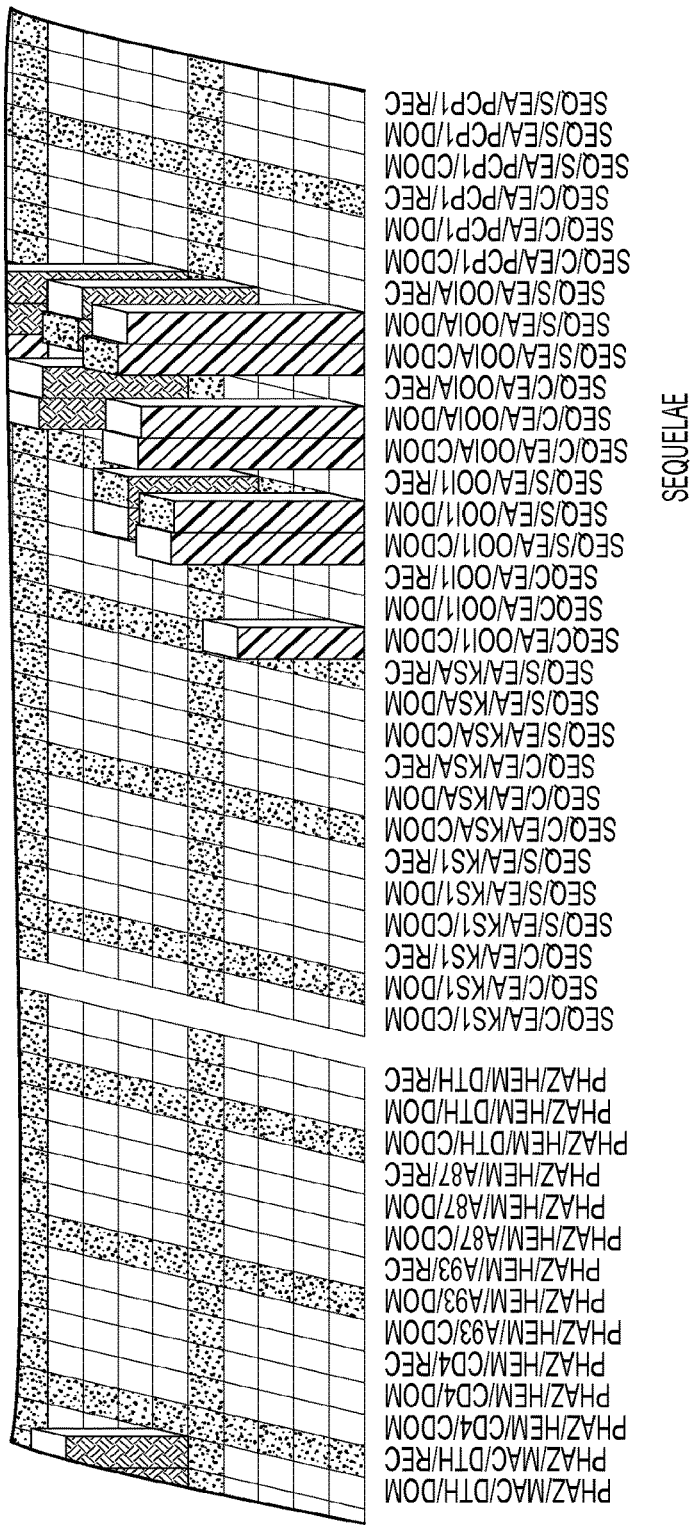
Figure 7P:
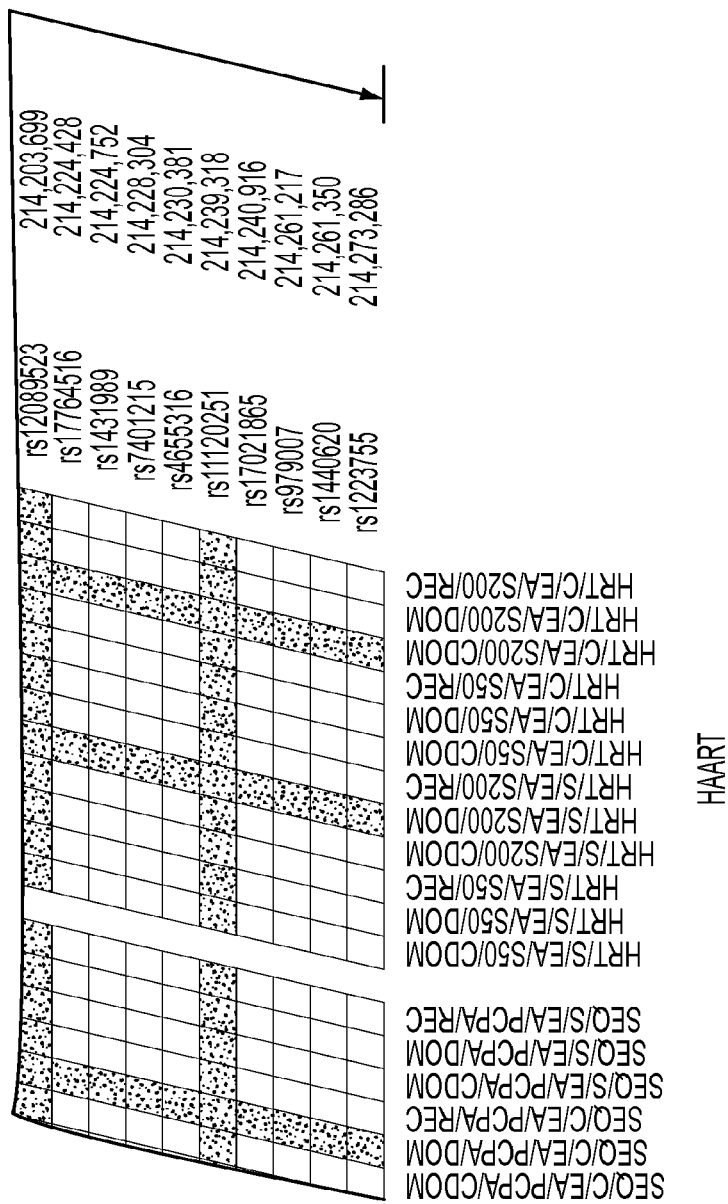

This is because an association of multiple linked SNPs may include LD between a minor (less common) allele at one locus and a common allele at an adjacent polymorphic site. Therefore, one minor allele may signal as susceptible (red) while the nearby minor allele may signal as resistant (green) although they are both tracking the same association effect. To assuage this computational artifact, GWATCH may include a "Polarize" option that, for any selected region, computes the direction of LD (+ or −LD) between the minor allele at the currently selected SNP (indexed SNP) and all minor alleles at adjacent SNPs. When there is a "discordant" LD relationship (i.e., the minor allele of the index locus tracks a common allele of the adjacent SNP variant), GWATCH may compute the multiplicative inverse (1/QAS) and color the HIGHWAY view and 3D-SNAPSHOT according to these inverted "polarized" QAS values. When the entire association signal for a region, driving the non-independent SNPs and non-independent tests, derives from a single causal allele within the region, the blocks of associated SNPs in the viewed region should be the same color after polarization (FIGS. 7A-7P). This exercise may help increase confidence that the association signal represents a true signal driven by a causal variant tracked by proxy SNPs and not a statistical or genotyping artifact. 2D- and 3D-SNAPSHOTs and POLARIZED 3D-SNAPSHOTs are presented from previously validated ARG regions (PARD3B and PROX1) in FIGS. 5A-5L, FIGS. 6A-6P, and FIGS. 7A-7P.

7.) The TRAX option may provide a more detailed report of tests performed for a single SNP. The p-values and QASs may be presented as a TRAX PAGE (FIGS. 8A-8B) which summarizes all test results for a single SNP (e.g., all the p-values and QASs for HIV infection, AIDS progression using categorical and survival analyses, AIDS sequelae, and HAART outcomes can be viewed in one track).

8.) GWATCH may produce in real time a detailed TRAX REPORT of derived statistics for all the tests accomplished including tables, bar graphs, survival curves and additional parameters for each test (FIGS. 9A-9B). TRAX REPORTs may be accessed by selecting the block of interest in HIGHWAY and clicking the "TRAX REPORT" option. GWATCH may compute and generate the report in real time (e.g., for 641 SNPs in 241 genes from exemplary dataset that were genotyped by PCR as replication of Affymetrix GWAS genotypes). The TRAX REPORT employs the underlying confidential genotype and clinical data but does not actually reveal any of this information publicly, thereby assuring protection of patient confidentiality. The primary confidential information on genotypes and clinical data may be securely stored on a server and not be accessible directly.

For any or all stages of disease (e.g., infection, progression, sequelae, or treatment; Table 3) GWATCH may compute a list of SNP-test combinations ranked according to p-values or QASs for the first pass at identifying association HITS thereby providing an association discovery tool. Further, GWATCH may identify chromosomal regions that show remarkably high density of significant p-values across closely linked SNPs and related tests for a disease stage (See below in "Statistical tools for the whole genome analysis").

GWATCH may enable investigators and users not connected to the original study to access the results of SNP association (from the whole genome sequencing or SNP array genotyping) to view and share their study design and results openly. It can be used for visualization of regions with significant p-values to inspect the pattern of variation across linked SNPs and also at different stages of disease (e.g., HIV infection, AIDS progression, AIDS sequelae and treatment outcome).

As a primary discovery approach, screening across unabridged test results poses large statistical penalties for multiple tests eroding confidence in associations that fail to achieve genome-wide significance. For this reason, one should use caution in inspection of putative regions of significance. Nonetheless, wholesale discarding of marginally significant "hits" may discount some true associations within the mix of statistical artifacts. GWATCH may offer an opportunity to screen the genome for disease-associated regions, which may contain causal SNP variants included (or not) in the SNP array used for genotyping, as well as proxy SNPs tracking the causal variant. Further, in complex diseases for which there are many different cohorts being studied (in HIV-AIDS there are at least twenty different groups conducting AIDS GWAS on small, well-defined cohorts that may differ in genetic background and clinical data available for association testing) GWATCH may offer rapid replication opportunities with an independent dataset.

To demonstrate GWATCH, three previously validated AIDS resistance gene regions, CCR5-Δ32, PROX1 and PARD3B, can be examined by simply entering rs-number, gene name or chromosome coordinates in the search option (see 2D image of PARD3B region in FIGS. 5A-5L and 3D images of PROX1 region in FIGS. 6A-6P and FIGS. 7A-7P). GWATCH moves HIGHWAY browser to the selected region so one can visualize the signal with the 2D and 3D-SNAPSHOTS plus the TRAX REPORTS that show the results clearly.

The GWATCH web browser may provide a dynamic visual journey, similar to driving in a video game along human chromosomes to view patterns of GWAS- or whole genome sequencing (WGS)-based variant association with any complex disease. It is meant to be appealing, intuitive, and accessible to non-experts and experts alike, including the various contributors to today's exciting gene association studies. The format and open web access may allow for importing new data from any disease-gene association study with multiple disease stages or genetic models of analysis. The wide breadth of test associations displayed is particularly suited to complex disease cohorts with detailed clinical parameters over distinct disease stages. Further, although GWATCH is potentially useful for initial gene discovery, an important corollary lies in providing rapid replication of gene discoveries from independent cohort studies by simply keying in the putative gene region and inspecting the many test results of the posted dataset. Since replication screens are hypothesis-driven, they avoid the stringent multiple test correction penalties of a GWAS/WGS ($p<10^{-8}$). Finally, different cohort studies can be compared directly or combined to build meta-analyses.

GWATCH is a generalizable web tool suitable for GWAS and/or WGS dataset for any complex disease. The "finished" or "processed" data (ones containing a final Data Table of p-values and QAS for completed association tests) can be uploaded directly. "Primary" or "unfinished" data (ones with genotypes and clinical data for which tests need to be constructed and calculated) may be uploaded for custom development of a disease-specific GWATCH-based analysis.

Should many cohort investigators release their unabridged results, then association discoveries may be replicated (or not) in a rapid, open and productive manner, allowing for large meta-analyses as have been proposed for HIV-AIDS and other complex diseases. Unlike other methods of data sharing, this results-based open data sharing/release approach may avoid any violation of patient privacy, IRB and HIPAA concerns, or informed consent constraints, since the primary clinical and genotype data remain confidential while the derivative results (p-values, QASs, plots) of multiple conceivable analytical approaches are openly released. In this approach, discovery and replication opportunities in important biomedical research may be expanded. This may ensure the maximum benefit of open access data sharing while protecting patients who prefer privacy but wish to see their volunteerism fulfilled.

Exemplary Implementation

GWATCH may be a web-based application that integrates several technologies and programming languages. Other types of applications such as server-based, hardware-based, etc. may be used. In web-based applications, the server-side may be represented by an Apache web server, which employs, for example, a PHP engine and a Java-based toolkit BATIK. R-PROJECT functions and modules may be used for performing statistical tests, polarization and density calculation. A database component of GWATCH may be implemented using MySQL and may allow access, retrieval and management of genotypes, clinical information and test results. On the front end, GWATCH may employ HTML5, Javascript, jQuery and WebGL for HIGHWAY browser interface, and Ajax and JSON technologies for data exchange between server and client.

Exemplary Statistical Methods

Different tests for analysis of associations in the various types of data are included in GWATCH. A user having clinical and genotype data for one or several populations can select an appropriate group of tests for screening statistical associations of infection or disease progression with genotypes. The results of all selected statistical tests may be visualized simultaneously in the HIGHWAY browser. Most of the statistical tests may be executed using R-project. In addition, a special option may enable display of detailed results of statistical analysis for any selected SNP via a TRAX REPORT.

Statistical Data

Input data for the analysis may consist of both clinical data and genotype data. The genotype data may contain information on all SNPs to be analyzed, and the corresponding genotype consists of two dummy (binary) variables specifying corresponding forms of two alleles or of one categorical variable with three levels specifying whole genotype information for the individual. In the former case, 0 may correspond to common SNP allele and 1 may correspond to minor SNP allele. In the latter case, common SNP homozygote may be coded by −1, minor SNP homozygote may be coded by 1 and heterozygote may be coded by 0. The required SNP information may be SNP identifier (SNP ID) and the corresponding coordinate. The input genotype data are expected to be sorted by SNP ID and/or by SNP coordinate sequentially. For further analysis, all individuals may be subjected to different types of genotype classification.

Genotype classification may be used as an explanatory factor for all statistical tests. Four types of genotype classification may be used: dominant (D) classification separates common homozygote from all other genotypes in two different groups; recessive (R) classification separates minor homozygote from all other genotypes; and co-dominant (CD) classification separates all individuals into three groups by their genotype; under allelic classification (A), two SNP alleles corresponding to any single individual are considered as two different observations with the same clinical data.

In certain embodiment, and for certain diseases, various types of clinical data may be acceptable for analysis, including, but not limited to: categorical and right-censored survival.

Categorical data may include the ID variable and numeric categorical variable having two or more levels specifying disease status. In the case of two levels, it is recommended to use code 1 for affected individuals (i.e., individuals which acquire infection, demonstrate symptoms of disease etc.) and code 0 for other individuals. In the case of more than two levels and ordinal categories it is recommended to use 0 for unaffected individuals (e.g., uninfected individuals or individuals with no disease symptoms etc.) and to choose positive numbers corresponding to other levels in the same order as the original categories.

Right-censored survival data may contain information on the exact time from baseline date (preferentially in days) to an event and type of the event that is given by the binary variable: 1 corresponding to failure (event occurred) and 0 corresponding to censoring (no event), for any individual. For the competing risks model it is possible to use several positive levels for different types of failures.

Statistical Tools for Associations

GWATCH software may allow analysis of disease associations with genotype for all available SNPs. Tests corresponding to different genotype classifications can be produced for any clinical data by the selected testing method. Stratified analysis may be available if the input clinical data contain a classification variable. In this case, any selected group of individuals may be analyzed separately and the results of these tests are displayed on different lanes of the Highway.

Categorical tests (CT) may be used for categorical statistical analysis of data organized as an mxk contingency table. The categorical data are required to perform categorical tests. Fisher's exact test (R-function "fisher.test( )") for 2×2 contingency tables and chi-square test (R-function "chisq.test( )") may be applied to produce p-value. The odds ratio for 2×2 contingency tables or the $(1-\rho)/(1+\rho)$ transformation of Pearson's correlation coefficient (designated as ez2-transformation for the square of the exponentiated Fisher's z-transformation) for the tables of other sizes define direction of the association, and therefore, color of the corresponding bar on the Highway.

Proportional hazards survival tests (PHST) may be used for the analysis of right-censored survival data. The Cox proportional hazards model may be used to produce p-value (R-function coxph( ), package survival). The direction of the associations is defined by the obtained relative hazard, which is calculated as hazard ratio (for binary genotype classifications A, D and R) or exponentiated slope of Cox's regression line (under CD genotype classification).

Categorical tests for survival data (CTSD) may be used to identify significant differences between categories of individuals grouped by failure times. The right-censored survival data are required to perform categorical survival tests. The baseline null hypothesis may be formulated in terms of the identity of cumulative distribution functions corresponding to different groups of individuals. Individuals involved in the analysis may be classified by observed failure or censoring times according to specified rules.

Hardy-Weinberg equilibrium (HWE) tests may be performed to evaluate significant deviation from Hardy-Weinberg equilibrium that is commonly used as an indicator of genotyping errors. Haldane's exact test on Hardy-Weinberg equilibrium may be used to produce p-values. Sign of Hardy-Weinberg disequilibrium statistic may be applied to specify direction of the disequilibrium. The R-function HWExact( ) of HardyWeingerg package may be used to perform HWE test.

For the convenience of test results representation, several different statistics, which describe the direction and strength of association between a SNP and disease characteristic in different tests (odds ratio, relative hazard and ez2-transformed correlation coefficient), may be combined under the general term of Quantitative Association Statistic (QAS). The QAS takes positive values. Values of QAS>1 and QAS<1 correspond to positive and negative associations, respectively.

TRAX REPORTs

A TRAX REPORT tool may provide for predetermined or variable display of information obtained from the systems and methods described herein. After screening for associations of clinical traits and genotypes one may be interested in closer review of certain SNPs. The TRAX REPORT tool may allow production of reports on extended statistical analysis for any single SNP if the corresponding genotype information available for all individuals. Important genotype information may be given in the header on the TRAX front page: SNP identifier, SNP coordinate, chromosome, alleles and their frequencies. A header may also list information on populations involved into analysis. In addition to the header, a front page may also contain summary for all tests with p-values and values of QAS represented for all tests in the bar plot form. Following pages of the TRAX REPORT may contain detailed information: contingency tables are produced in the form of corresponding bar plots for any categorical test (including progression categorical tests) and Kaplan-Meier survival curves are reported for all three genotypes for all survival tests.

Figure 8B:
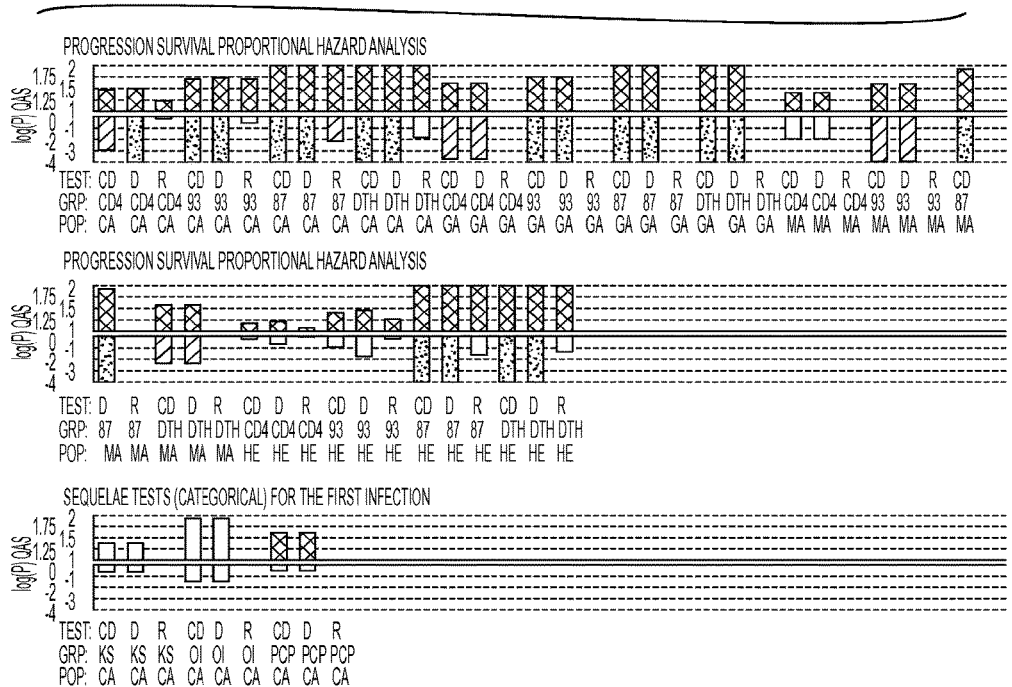

FIGS. 8A-8B shows an embodiment of a TRAX PAGE, which is a summary of all test results for a single SNP for a study group (e.g., p-values and QASs for HIV infection, AIDS progression using categorical and survival tests, AIDS sequelae, and HAART outcomes can be viewed and compared). TRAX PAGE can be generated de novo for any SNP of interest by placing mouse tip over a significant bar in the HIGHWAY browser and selecting the TRAX PAGE option from the data window that appears.

FIGS. 9A-9B shows an embodiment of a section of a detailed multi-page TRAX REPORT illustrating a section of line graphs. A TRAX REPORT may additionally be comprised of derived statistics for all the tests accomplished including tables, bar graphs, survival curves and additional parameters for each test, and the like. A TRAX PAGE can be generated de novo for any SNP of interest by placing mouse tip over a significant bar in HIGHWAY browser and selecting the TRAX PAGE option from the data window that appears.

Statistical Tools for the Whole Genome Analysis

Several statistical tools addressing SNP compositions may be available.

Polarization tool may allow adjustment of QAS results for minor and common SNP-alleles around some fixed SNP (called index SNP) for better approximations of true associations. A polarization table may be produced using linkage disequilibrium coefficients (D') between neighboring SNPs. Linkage disequilibrium coefficients may be calculated for 80 SNPs upstream and 80 SNPs downstream of the index SNP. This can similarly be calculated for 20, 40, 60, 100 or 120 or more upstream or downstream SNPs, with the choice generally depending on the density of the SNPs in the general location of interest. Other numbers may be used depending on particular applications. In case of sufficiently large positive value of linkage disequilibrium (D'>0.9), the polarization mark may be assigned to 1, whereas in case of sufficiently large negative linkage disequilibrium (D'<−0.9) the polarization mark may be assigned to −1. If linkage disequilibrium is sufficiently small, the polarization mark may be assigned to 0. In the process of polarization, QAS values for test results of neighboring SNPs may be inverted if the polarization mark is −1 implying the inversion of direction of disease association for such SNPs.

Manhattan plots of −log p-values may be produced for any single test for all available SNPs. A Manhattan plot may be a type of scatter plot, usually used to display data with a large number of data-points—many of non-zero amplitude—and with a distribution of higher-magnitude values. FIG. 3 shows an example of an embodiment of a Manhattan plot.

Significant regions (regions of concentration of small p-values for density top scoring) may be identified using density feature. Density top scoring that identifies regions of concentration of small p-values may be calculated for each SNP in two steps:

1) in the window of specified size (n SNPs upstream and downstream or n Kbp upstream and downstream) average −log p-value may be computed for each test (lane of the Highway)

2) these per-test (per-lane) averages are used for calculating density at this SNP either by averaging them or by finding the largest one (depending on the option chosen)

The second step can be performed for all the tests or for the group of tests by the disease stage (e.g., all tests for HIV infection, all tests for AIDS progression etc.).

Statistical Tests and Data Used for Complex AIDS Study

To illustrate GWATCH utility in the analysis of GWAS results, data from multicenter longitudinal studies of several cohorts of patients exposed to the risk of HIV infection and/or already infected with HIV were used: ALIVE, DCG, HGDS, HOMER, LSOCA, MACS, MHCS and SFCC. The total pool of patients was divided into three groups A, B and C based on ethnicity and timing of data development (see Table 2). A total of 5,922 patients were analyzed in all 3 groups.

All patient samples and genotypes may be subjected to quality control filtering. Once final genotypes may be obtained, population structure can be assessed using the Principal Components Analysis module of Eigensoft software in European and African American populations and structured SNP variants may be excluded.

Following statistical tests may be applied to the analysis of HIV-AIDS research data obtained from these patients. For each of the tests described below 3 genetic models may be used (D, R and CD, see above under "Genotype classification").

Infection Tests (INF).

Infection tests may be used to specify the association of any selected genotype with HIV infection. The original clinical data may be of categorical type based on the population of seronegatives (SN, individuals which stay HIV-negative throughout the whole study) at the baseline with the response variable indicating serostatus at the endpoint and having three levels: "high risk exposed uninfected" (HREU) seronegatives, "other seronegatives" (OSN) and "seroconverters" (SC, individuals which entered the study as HIV-negative, but became HIV-positive during the study). Three combinations of HIV status classifications can be used to perform the categorical tests: "SC" vs. "HREU", "SC" vs. "HREU" plus "OSN" and "SC" vs. "HREU" vs. "OSN". In addition to the three genotype classifications described above (D, R and CD), allelic model (A) was also used for this test. One more group of individuals based on infection status, "seroprevalents" (SP, individuals which entered the study already being HIV-positive), was not informative for this type of test and therefore was not included in it.

Disease Progression Tests.

The disease progression tests can be used for screening significant associations between AIDS progression and genotype. The original data were of right-censored survival type under four different criteria of AIDS disease: CD4<200 (level of CD4+ cells falling below 200 cells/mm$^3$), AIDS-1987 (patient meeting criteria of 1987 CDC definition of AIDS), AIDS-1993 (patient meeting criteria of 1993 CDC definition of AIDS) and Death from AIDS. Only seroconverter and seroprevalent individuals were included in this analysis. Seroconverter individuals may be included into analysis with HIV infection date (date of seroconvertion) as the baseline. Seroprevalent individuals may be included into categorical analysis with the date of the first visit as the baseline with some warnings.

Disease progression categorical analysis (PDCA) may use the categorical tests for survival data (CTSD) approach described above. The CTSD can be performed in dichotomous (PDCA2, two groups by the survival time or current status data) and multipoint (PDCAM, more than two groups by the survival time) forms. All individuals censored before the breakpoint may be removed from the PDCA dichotomous analysis, as well as the seroprevalent individuals who failed before the breakpoint. All remaining individuals censored or failed after the breakpoint may be classified into the group of long-term survivors (LTS, those who do not show AIDS symptoms before the breakpoint).

Proportional hazard (PHAZ) analysis of disease progression may use the proportional hazards survival tests (PHST) approach described above. These tests may be performed for all four criteria of AIDS. Only seroconverter individuals were included into PHAZ analysis.

Sequelae Tests.

Survival and categorical tests may be performed for survival data on Kaposi's sarcoma (KS), *Pneumocystis carnii* pneumonia (PCP), cytomegalovirus infection (CM), lymphoma (LY), mycobacterial infection (MYC) and other opportunistic infections (OOI). As in progression disease tests, survival sequelae tests may include seroconverters only, while categorical sequelae tests may include both seroconverters and seroprevalents.

Sequelae tests for any infection order may classify patients based on whether specific sequela occurred at all, irrespectively of its order (i.e., whether it was the first sequela to occur for patient). The survival tests (SEQSA) under proportional hazards model as well as the progression categorical tests (SEQCA) may be performed separately for each of the diseases described above.

Sequelae tests for the first infection may classify patients based on whether specific sequela occurred first or not. The survival tests (SEQS1) under proportional hazards model as well as the progression categorical tests (SEQC1) may be performed separately for each of the diseases described above.

Highly Active Antiretroviral Therapy (HAART).

HAART tests may be performed for the cohorts of patients who were subject to this type of treatment. Patients may be classified based on either the level of suppression of HIV viral load or on the rebound of viral load following its suppression. Both survival (HRTS) and progression categorical (HRTC) tests may be used for this analysis.

Hardy-Weinberg Equilibrium Tests (HWE).

The HWE tests may be performed to control for the quality of data used for the screening of associations. Large deviations from Hardy-Weinberg equilibrium are not typical for the large populations and thus signal the genotyping error or some other type of data quality breach.

TABLE 1

Potential Features of GWATCH.

| Features displayed | Representative FIG. |
|---|---|
| 1. Unabridged Data Table of SNP chromosome coordinates, MAF*, p-value and QAS** for each SNP for each test | — |
| 2. Association Tests List and Manhattan Plots for each test across all SNPs | FIG. 3 |
| 3. SNAPSHOTS of SNP-test results in a chromosome region: | |
| 1. 2D Heat Plot Snapshot illustrating p-values in any selected chromosome region | FIG. 5 |
| 2. 3D Checkerboard Plot Snapshot illustrating p-values and QAS** in any selected chromosome region | FIG. 6 |
| 3. LD-polarized 3D Checkerboard Snapshot illustrating p-values and QAS** in any selected chromosome region | FIG. 7 |
| 4. Dynamic Highway View by Chromosome Browser illustrating p-values and QAS** | FIG. 4 |
| 5. Top association hits: | |
| 1. Top hits based on ranked -log p-value | — |
| 2. Top hits based on ranked QAS** | — |
| 3. Top hits based on ranked Density of -log p-value within a SNP genomic region | — |
| 6. TRAX feature: | |
| 1. TRAX PAGE - two-page graphic summary illustrating p-values and QAS** for one selected SNP | FIG. 8 |
| 2. TRAX REPORT - eleven-page analysis summary with graphs, curves and tables for all association tests for one selected SNP | FIG. 9 |

Abbreviations:
*MAF—minor allele frequency;
**QAS—quantitative association statistic (OR, RH, ez2-transformed correlation coefficient).

TABLE 2

Patient categories and counts in Groups A-C.

| | | Number of patients for each group | | | |
|---|---|---|---|---|---|
| Abbreviation | Risk groups | Group A EA*-I | Group B EA*-Total | Group C AA** | Total B + C |
| HREU | High Risk Exposed HIV Uninfected | 254 | 300 | 148 | 448 |
| EU (except HREU) | Exposed HIV Uninfected (all risks) | 1 | 351 | 267 | 618 |
| SC | Sero-Convertor | 703 | 767 | 288 | 1 055 |
| SP-LTS | Sero-Prevalent-Long-Term-Survivor (no AIDS for >10 years) | 444 | 831 | 170 | 1 001 |
| Sequelae | AIDS sequelae diagnosis | 461 | 1 848 | 0 | 1 848 |
| HAART | Anti-retroviral treatment | 485 | 1 319 | 65 | 1 384 |
| Total study participants | | 1 527 | 4 462 | 1 460 | 5 922 |

Abbreviations:
*EA—European Americans;
**AA—African Americans.

TABLE 3

Tests per study group.

| Clinical stage | Test type | Number of tests for each group | | |
|---|---|---|---|---|
| | | Group A | Group B | Group C |
| I. HIV Infection | Ia. Infection - categorical | 3 | 12 | 12 |
| II. HIV Progression | IIa. Progression - categorical dichotomous | 12 | 12 | 12 |
| | IIb. Progression - categorical multipoint | 12 | 12 | 12 |
| | IIc. Progression - survival | 48 | 48 | 24 |
| III. AIDS defining Conditions | IIIa. Sequelae - categorical first sequela | 9 | 9 | — |
| | IIIb. Sequelae - survival first sequela | 9 | — | — |
| | IIIc. Sequelae - categorical any sequelae | 9 | 33 | — |
| | IIId. Sequelae - survival any sequelae | 9 | 6 | — |
| IV. Treatment with ARV | IVa. HAART - categorical | 6 | — | — |
| | IVb. HAART - survival | 6 | 12 | — |
| Total | | 123 | 144 | 60 |

Although not required, the systems and methods are described in the general context of computer program instructions executed by one or more computing devices that can take the form of a traditional server/desktop/laptop; mobile device such as a smartphone or tablet; etc. Computing devices typically include one or more processors coupled to data storage for computer program modules and data. Key technologies include, but are not limited to, the multi-industry standards of Microsoft and Linux/Unix based Operating Systems; databases such as SQL Server, Oracle, NOSQL, and DB2; Business Analytic/Intelligence tools such as SPSS, Cognos, SAS, etc.; development tools such as Java, .NET Framework (VB.NET, ASP.NET, AJAX.NET, etc.); and other e-Commerce products, computer languages, and development tools. Such program modules generally include computer program instructions such as routines, programs, objects, components, etc., for execution by the one or more processors to perform particular tasks, utilize data, data structures, and/or implement particular abstract data types. While the systems, methods, and apparatus are described in the foregoing context, acts and operations described hereinafter may also be implemented in hardware.

FIG. 1 shows an exemplary system 100 for visualization, sharing and analysis of large data sets according to one embodiment. In this exemplary implementation, system 100 may include one or more servers/computing devices 102 (e.g., server 1, server 2, . . . , server n) operatively coupled over network to one or more client computing devices 106-1 to 106-n, which may include one or more consumer computing devices, one or more provider computing devices, one or more remote access devices, etc. The one or more servers/computing devices 102 may also be operatively connected, such as over a network, to analytical software 104 and/or one or more databases 108 (e.g., database 1, database 2, . . . , database n). The one or more databases 108 may include data storing and/or data retrieval capabilities. The analytical software 104 may provide for data processing, such as format conversion and/or statistical analysis. Various devices may be connected to the system, including, but not limited to, client computing devices, consumer computing devices, provider computing devices, remote access devices, etc.

Server/computing device 102 may represent, for example, any one or more of a server, a general-purpose computing device such as a server, a personal computer (PC), a laptop, a smart phone, a tablet, and/or so on. The server/computing device 102 may provide one or more interfaces for data input and output. The server/computing device 102 may provide a 3D dynamic graphical engine. Networks may represent, for example, any combination of the Internet, local area network(s) such as an intranet, wide area network(s), cellular networks, WIFI networks, and/or so on. Such networking environments are commonplace in offices, enterprise-wide computer networks, etc. Client computing devices 106, which may include at least one processor, may represent a set of arbitrary computing devices executing application(s) that respectively send data inputs to server/computing device 102 and/or receive data outputs from server/computing device 102. Such computing devices include, for example, one or more of desktop computers, laptops, mobile computing devices (e.g., tablets, smart phones, human wearable device), server computers, and/or so on. In this implementation, the input data comprises, for example, genome data, clinical data, phenotypic data and/or so on, for processing with server/computing device 102. In one implementation, the data outputs include, for example, emails, templates, forms, and/or so on. Embodiments of the present invention may also be used for collaborative projects with multiple users logging in and performing various operations on a data project from various locations. Embodiments of the present invention may be web-based, smart phone-based and/or tablet-based or human wearable device-based. Each of the client computing devices 106 may upload research data, including raw or calculated data. One or more of the client computing devices 106 may view data through an interface and/or download data, tables, top hits, etc.

In this exemplary implementation, server/computing device 102 includes at least one processor coupled to a system memory. System memory may include computer program modules and program data.

Figure 2:
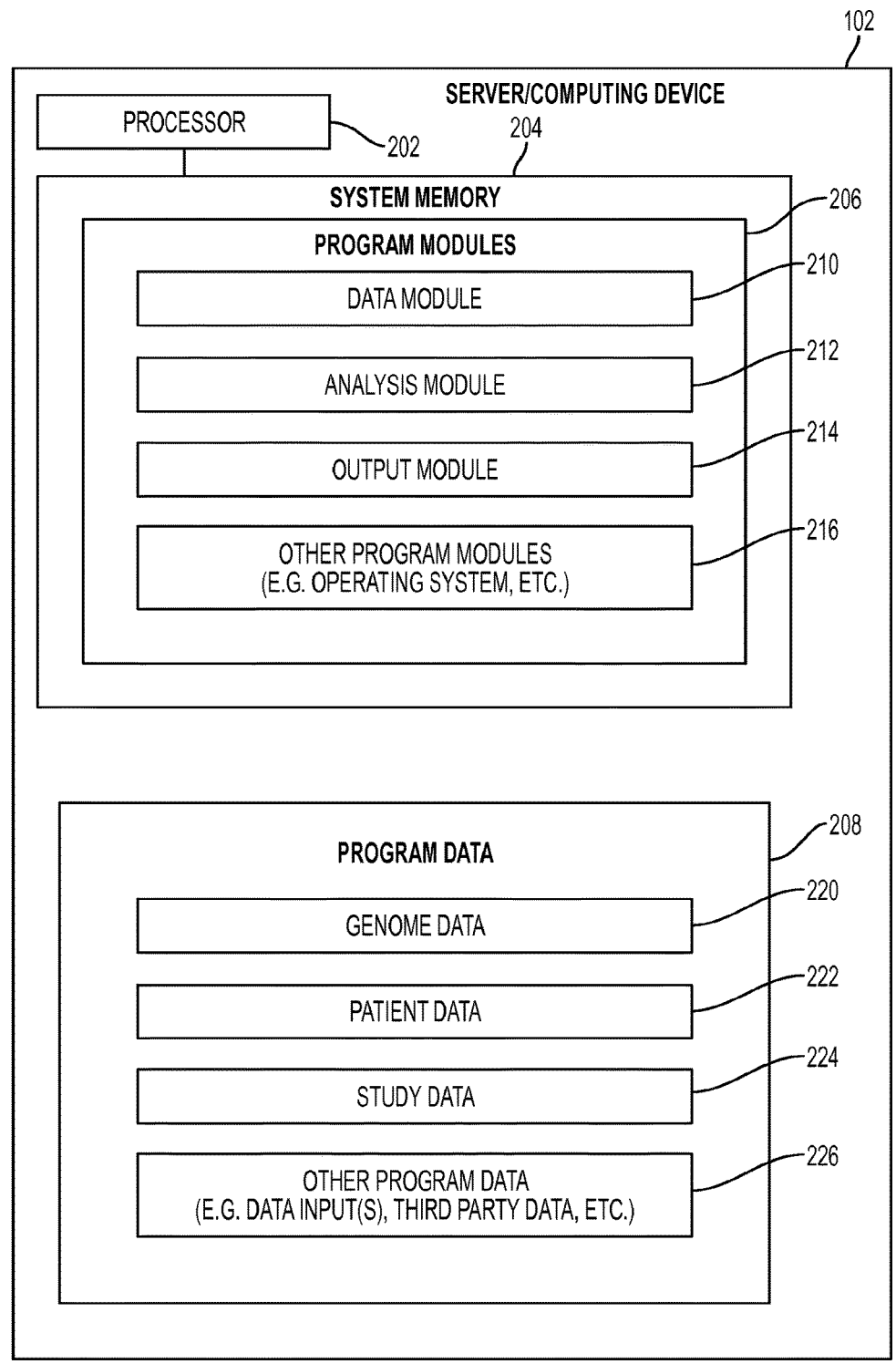
FIG. 2 shows an exemplary system for computational aspects of gene discovery and data sharing in disease association analyses across the genome.

In this exemplary implementation, server/computing device 102 includes at least one processor 202 coupled to a system memory 204, as shown in FIG. 2. System memory 204 may include computer program modules 206 and program data 208. In this implementation program modules 206 may include data module 210, analysis module 212, output module 214, and other program modules 216 such as an operating system, device drivers, etc. Each program module 210 through 216 may include a respective set of computer-program instructions executable by processor(s) 202. This is one example of a set of program modules and other numbers and arrangements of program modules are contemplated as a function of the particular arbitrary design and/or architecture of server/computing device 102 and/or system 100 (FIG. 1). Additionally, although shown on a single server/computing device 102, the operations associated with respective computer-program instructions in the program modules 206 could be distributed across multiple computing devices. Program data 208 may include genome data 220, patient data 222, study data 224, and other program data 226 such as data input(s), third party data, and/or others. Although it is contemplated that the computerized application of the embodiments described herein may be incorporated on a number of types of computing devices, the systems and methods necessarily require the use of some type of computing device. This is because the embodiments of the systems and methods described herein may be utilized to analyze and/or display large amounts of data that could not possibly be accomplished without the aid of some type of computing device.

In some embodiments, an exemplary system may include specialized genetic equipment. Specialized genetic equipment may include genetic sequencers, various polymerase chain reaction equipment and associated methods, and the like.

Embodiments described herein may permit individuals to scan very large data sets with a lower loss of attention to detail than presently used to review large data sets. This may permit those analyzing large amounts of data to more accurately visualize trends and minor differences. While not wishing to be constrained by a present theory, it is believed that this greater accuracy arises from a human ability to gauge three dimensional information more rapidly than the same information displayed in a two dimensional manner or tabular, non-graphical manner.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. An automated computerized method for analyzing, displaying, replicating, and releasing data, comprising the steps of:
    using a computer process to execute the computerized method comprising:
        anonymizing a genomic data set to produce an input dataset;
        releasing and sharing data;
        analyzing a genome-wide dataset;
        displaying an expanded visual display of gene associations for genome wide variants;
        providing a dynamic genome browser illustrating gene association chromosomal regions; and
        expanding a displayed result of the input dataset for genome-wide variants including real-time replication of candidate or putative genes to limit statistical penalties in a visual array wherein the visual array is depicted as a three-dimensional image that can be displayed as a moving video mode above a surface.

2. The method of claim 1, wherein the visual array comprises two axes in a horizontal plane representing a first classification dimension and a second classification dimension, and a block height rising from a third plane represents a third classification dimension.

3. The method of claim 2, wherein the visual array further comprises a fourth classification dimension that represents an additional component of a data point value.

4. The method of claim 3, further comprising representing the fourth classification dimension by color or shape of the blocks in the third classification dimension.

5. The method of claim 1, wherein the genome-wide variants are selected from the group consisting of single nucleotide polymorphisms (SNP), indels, and copy number variations (CNV).

6. The method of claim 2, wherein the first classification dimension comprises a linear ordering of data entries.

7. The method of claim 2, wherein the second classification dimension comprises analysis criteria.

8. The method of claim 1, further comprising reformatting the input dataset to create an unabridged data table.

9. The method of claim 1, wherein the input data set is a result of a genome-wide association study (GWAS).

10. The method of claim 1, wherein the input data set is a result of a whole genome sequence (WGS).

11. The method of claim 1, wherein a first axis of the visual array represents single nucleotide polymorphisms (SNPs) linearly ordered according to genome positions;
    a second axis represents different association tests performed;
    height of blocks rising above the surface represents reversed sign decimal logarithm of p-value;
    and color represents quantitative association statistics.

12. The method of claim 11, wherein the quantitative association statistics represent direction and strength of associations for association tests.

13. The method of claim 12, wherein the quantitative association statistics are selected from the group consisting of odds ratio, relative hazard, Pearson's correlation coefficient (ez-2-transformed) and combinations thereof.

14. The method of claim 1, further comprising isolating and sampling deoxyribonucleic acid (DNA) to produce the genome-wide set.

15. An automated computerized method for visualization, analysis, anonymization, sharing, and replication of large datasets corresponding to genomic data, the computerized method comprising the steps of:
    using a computer process to execute the computerized method comprising:
        isolating and sampling deoxyribonucleic acid (DNA) to produce a genomic data set;
        anonymizing the genomic dataset;
        analyzing the genomic dataset;
        displaying an expanded visual display of gene associations for genome-wide variants;
        providing a dynamic genome browser illustrating gene association chromosomal regions; and
        expanding a display of a result of an input dataset for genome-wide variants including real-time replication of candidate or putative genes to limit statistical penalties in a visual array wherein the visual array is depicted as a three-dimensional image that can be displayed as a moving video mode above a surface.

16. The method of claim 15, wherein the visual array comprises two axes in a horizontal plane represent a first classification dimension and a second classification dimension, and a block height rising from a third plane represents a third classification dimension.

17. The method of claim 16, wherein the visual array further comprises a fourth classification dimension that represents an additional component of a data point value.

18. The method of claim 17, further comprising representing the fourth classification dimension by color or shape of the blocks in the third classification dimension.

19. The method of claim 15, wherein the input data set is a result of a genome-wide association study (GWAS).

20. The method of claim 15, wherein the input data set is a result of a whole genome sequence (WGS).

* * * * *